US009657332B2

(12) United States Patent
Whitman et al.

(10) Patent No.: US 9,657,332 B2
(45) Date of Patent: May 23, 2017

(54) PROBES FOR IMPROVED MELT DISCRIMINATION AND MULTIPLEXING IN NUCLEIC ACID ASSAYS

(71) Applicant: LUMINEX CORPORATION, Austin, TX (US)

(72) Inventors: Doug Whitman, Round Rock, TX (US); Nicolas Arab, Austin, TX (US); Chuck Collins, Austin, TX (US)

(73) Assignee: LUMINEX CORPORATION, Austin, TX (US)

( * ) Notice: Subject to any disclaimer, the term of this patent is extended or adjusted under 35 U.S.C. 154(b) by 142 days.

(21) Appl. No.: 14/456,239

(22) Filed: Aug. 11, 2014

(65) Prior Publication Data

US 2015/0044680 A1 Feb. 12, 2015

Related U.S. Application Data

(60) Provisional application No. 61/864,128, filed on Aug. 9, 2013.

(51) Int. Cl.
*C12Q 1/68* (2006.01)
*C07H 21/00* (2006.01)

(52) U.S. Cl.
CPC ................ *C12Q 1/6818* (2013.01)

(58) Field of Classification Search
CPC ................ C12Q 1/68; C07H 21/00
See application file for complete search history.

(56) References Cited

U.S. PATENT DOCUMENTS

| 5,424,413 | A | * | 6/1995 | Hogan | C12N 15/1068 |
| | | | | | 435/6.1 |
| 6,251,639 | B1 | * | 6/2001 | Kurn | C12Q 1/6844 |
| | | | | | 435/6.1 |
| 6,350,580 | B1 | * | 2/2002 | Sorge | C12Q 1/686 |
| | | | | | 435/6.1 |
| 6,692,917 | B2 | * | 2/2004 | Neri | C12Q 1/6823 |
| | | | | | 435/6.1 |
| 7,189,508 | B2 | * | 3/2007 | Sorge | C12Q 1/6823 |
| | | | | | 435/6.1 |
| 7,309,573 | B2 | * | 12/2007 | Sorge | C12Q 1/6844 |
| | | | | | 435/6.1 |
| 7,351,557 | B2 | * | 4/2008 | Kurn | C12N 15/1096 |
| | | | | | 435/91.1 |
| 7,381,530 | B2 | * | 6/2008 | Hall | C12N 9/1252 |
| | | | | | 435/6.1 |
| 7,759,062 | B2 | | 7/2010 | Allawi et al. | 435/6.1 |
| 2002/0150900 | A1 | * | 10/2002 | Marshall | C12Q 1/6823 |
| | | | | | 435/6.12 |
| 2006/0078936 | A1 | | 4/2006 | Grenier et al. | 435/6.18 |
| 2006/0188902 | A1 | * | 8/2006 | Narayanan | C12Q 1/6816 |
| | | | | | 435/6.1 |
| 2007/0020656 | A1 | * | 1/2007 | Sorge | C12Q 1/6816 |
| | | | | | 435/6.11 |
| 2007/0117125 | A1 | * | 5/2007 | Chemeris | C12Q 1/686 |
| | | | | | 435/6.18 |
| 2011/0288148 | A1 | * | 11/2011 | Pierce | C12N 15/111 |
| | | | | | 514/44 A |

FOREIGN PATENT DOCUMENTS

| WO | WO 2007/045890 | | 4/2007 |
| WO | WO 2015/021460 | * | 2/2015 |
| WO | WO 2016/025452 | * | 2/2016 |

OTHER PUBLICATIONS

Fiandaca et al.,Self-Reporting PNA/DNA Primers for PCR Analysis. Genome Research 11 :609 (2001).*
Johnson et al., A third base pair for the polymerase chain reaction: inserting isoC and isoG. Nucleic Acids Research 32(6) : 1937 (2004).*
Li et al., A new class of homogeneous nucleic acid probes based on specific displacement hybridization. Nucleic Acids Research 30 (2) : e5 (2002).*
Lyamichev et al., Polymorphism identification and quantitative detection of genomic DNA by invasive cleavage of oligonucleotide probes. Nature Biotechnology 17 :292 (1999).*
Moser et al., Enzymatic repair of an expanded genetic information system. Nucleic Acids Research 31 (17) : 5048 (2003).*
Murakami et al.,Sensitive RNA detection by combining three-way junction formation and primer generation-rolling circle amplification. Nucleic Acids Research 40(3) : e22(2012).*
Nazarenko et al., A closed tube format for amplification and detection of DNA based on energy transfer. Nucleic Acids Research 25(12) : 2516 (1997).*
Nuovo et al., In Situ Amplification Using Universal Energy Transfer-labeled Primers. J. of Histochemistry & Cytochemistry 47 (3) : 273 (1999).*
Ranasinghe et al.,Fluorescence based strategies for genetic analysis. Chem. Commun. 2005, 5487-5502.*
Sherrill et al., Nucleic Acid Analysis Using an Expanded Genetic Alphabet to Quench Fluorescence. JACS126 :4550 (2004).*
El-Hajj, et al., "Use of sloppy molecular beacon probes for identification of mycobacterial species," *J. Clin. Microbiol.*, 47: 1190-8, 2009.
Faltin, et al., "Mediator Probe PCR: a novel approach for detection of real-time PCR based on label-free primary probes and standardized secondary universal fluorogenic reporters," *Clin. Chem.*, 58:1546-56, 2012.
International Search Report and Written Opinion issued in PCT/US2014/050514, dated Dec. 15, 2014.
Murakami, et al. "Sensitive RNA detection by combining three-way junction formation and primer generation-rolling circle amplification" *Nuc. Acids Res.*, 40:1-10, 2011.

* cited by examiner

Primary Examiner — Ethan C Whisenant
(74) Attorney, Agent, or Firm — Parker Highlander PLLC

(57) ABSTRACT

Methods and compositions for the detection and quantification of nucleic acids are provided. In certain embodiments, methods involve the use of primers or probes that comprise a non-natural nucleotide linked to a reporter. Target nucleic acids are detected by the polymerization of a complementary probe or primer that incorporated a cognate non-natural nucleotide linked to a quencher.

17 Claims, 17 Drawing Sheets

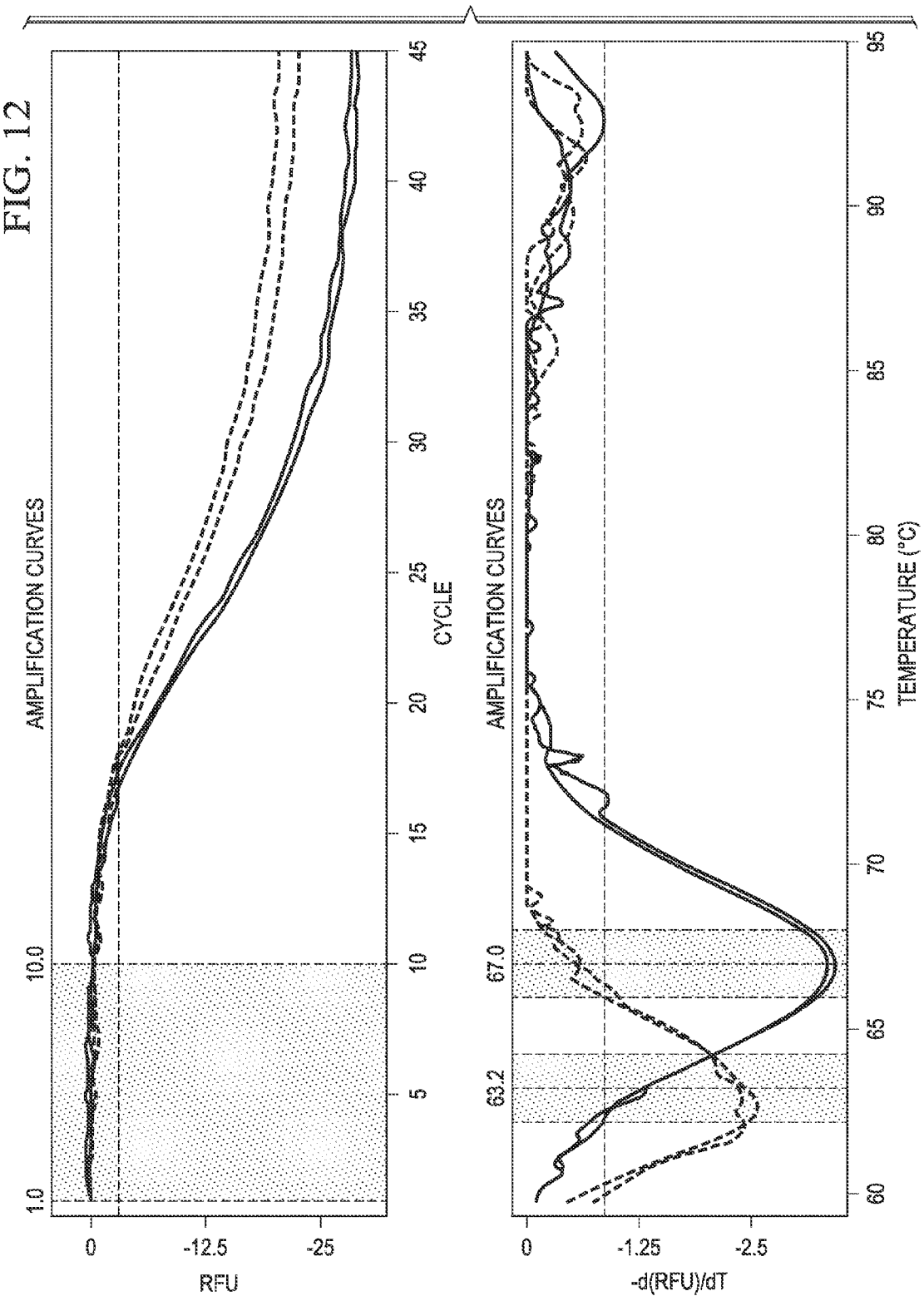

PROBES FOR IMPROVED MELT DISCRIMINATION AND MULTIPLEXING IN NUCLEIC ACID ASSAYS

This application claims benefit of priority to U.S. Provisional Application Ser. No. 61/864,128, filed Aug. 9, 2013, the entire contents of which are hereby incorporated by reference.

INCORPORATION OF SEQUENCE LISTING

The sequence listing that is contained in the file named "LUMNP0119US_ST25.txt", which is 5 KB (as measured in Microsoft Windows®) and was created on Jul. 31, 2014, is filed herewith by electronic submission and is incorporated by reference herein.

BACKGROUND OF THE INVENTION

1. Field of the Invention

The present invention relates generally to the field of molecular biology. More particularly, it concerns the detection of nucleic acids.

2. Description of Related Art

Polymerase chain reaction (PCR) is a molecular biology technique for enzymatically replicating DNA without using a living organism. PCR is commonly used in medical and biological research labs for a variety of tasks, such as the detection of hereditary diseases, the identification of genetic fingerprints, the diagnosis of infectious diseases, the cloning of genes, paternity testing, and DNA computing. PCR has been accepted by molecular biologists as the method of choice for nucleic acid detection because of its unparalleled amplification and precision capability. DNA detection is typically performed at the end-point, or plateau phase of the PCR reaction, making it difficult to quantify the starting template. Real-time PCR or kinetic PCR advances the capability of end-point PCR analysis by recording the amplicon concentration as the reaction progresses. Amplicon concentration is most often recorded via a fluorescent signal change associated with the amplified target. Real-time PCR is also advantageous over end-point detection in that contamination is limited because it can be performed in a closed system. Other advantages include greater sensitivity, dynamic range, speed, and fewer processes required.

Several assay chemistries have been used in real-time PCR detection methods. These assay chemistries include using double-stranded DNA binding dyes, dual-labeled oligonucleotides, such as hairpin primers, and hairpin probes. However, a drawback of current real-time PCR is its limited multiplexing capability. Current real-time PCR technologies use reporter fluorochromes that are free in solution. This design necessitates the use of spectrally distinct fluorochromes for each assay within a multiplex reaction. For example, a multiplex reaction designed to detect 4 target sequences would require an instrument capable of distinguishing 4 different free floating fluorochromes by spectral differentiation, not including controls. These requirements not only limit the practical multiplexing capability, but also increase costs since such instruments typically require multiple emission sources, detectors, and filters. Current real-time PCR technologies have multiplexing capabilities from about 1-6 plex.

SUMMARY OF THE INVENTION

The present invention relates to systems and methods for amplification and detection of DNA. In particular, the present invention provides systems and methods that greatly increase multiplexing capabilities of real-time nucleic acid amplification (e.g., via PCR).

In one embodiment, a method is provided for detecting the presence of a target nucleic acid in a sample comprising: (a) contacting the sample with a first set of primers comprising a first primer comprising, from 5' to 3', (i) a reporter, (ii) a hairpin with a known melt point, (iii) a polymerase extension-blocking modification, (iv) at least one non-natural nucleotide, and (v) a target-specific sequence, complementary to a first region on the first strand of a target nucleic acid; and a second primer comprising a sequence complementary to a region on a second strand of the target nucleic acid; (b) amplifying the target nucleic acid with the first set of primers, wherein said amplifying is performed in the presence of a quencher-labeled non-natural nucleotide that base-pairs with the non-natural nucleotide of the first primer; and (c) detecting the presence of the target nucleic acid by detecting a change in signal (e.g., a quenching of signal) from the reporter on the first primer.

Thus, in a more specific embodiment a method is provided for detecting the presence of one or both of a first and second target nucleic acid molecule in a sample comprising: (a) contacting the sample with at least a first and second set of primers, each set of primers comprising a first primer comprising, from 5' to 3', (i) a reporter, (ii) a hairpin with a known melt point, (iii) a polymerase extension-blocking modification, (iv) at least one non-natural nucleotide, and (v) a target-specific sequence, complementary to a first region on the first strand of a target nucleic acid; and a second primer comprising a sequence complementary to a region on a second strand of the target nucleic acid, wherein the reporters from the first and second set of primer are the same and wherein the first and second set of primers comprise hairpins with distinguishable melt points; (b) amplifying the target nucleic acids with the first and second set of primers (to obtain an amplification product), wherein said amplifying is performed in the presence of a quencher-labeled non-natural nucleotide that base-pairs with the non-natural nucleotide of the first primer of the first and second primer sets; (c) detecting the presence of a target nucleic acid molecule by detecting a change in signal from the reporter on the first primer from the first or second set of primers; and (d) determining whether the quenching of signal from the reporter resulted from the presence of the first target nucleic acid molecule, the second target nucleic acid molecule, or both by changing the temperature of the sample and determining the melt point or melt peaks corresponding to unquenching of the reporter, thereby detecting the presence of one or both of the first and second target nucleic acid molecules (e.g., based on the different melt points of the hairpins from the first and second primer sets).

In certain aspects, the reporter for use in the instant embodiments may be a fluorophore, such as a fluorophore attached at the 5' end of the first primer. Accordingly, in some cases, a change is the signal may be a decrease in a fluorescent signal. In a further aspect, detecting a change in signal from the reporter on the first primer may further comprise hybridizing the amplification products comprising the reporter and the quencher (e.g., a dark quencher).

In further aspects, detecting a change in signal from the reporter may comprise detecting the change (or rate of change) in signal, such as unquenching of a signal as the temperature of the sample is changed. In one aspect, the temperature of the sample may be increased above (or decreased below) the melt point of the hairpin of one more of the primers in the sample. In the case where two or more primer sets are present, changing the temperature of a sample may comprise increasing the temperature of the sample from a temperature that is below the melt point of the hairpins of both of the first primers in the first and second set of primers to a temperature that is above the melt point of both of the hairpins.

Certain aspects of the embodiments concern the use of at least one non-natural nucleotide. In some aspects, the non-natural nucleotide is an isobase, such as iso-guanine (isoG) or iso-cytosine (isoC). In this aspect, the quencher-labeled non-natural nucleotide is a cognate isoC (or isoG). In still further aspects, at least one of the first and/or second primers comprises at least one non-natural nucleotide in the target-specific sequence. For example, in some aspects, the non-natural nucleotide in the target-specific sequence regulates sequence-specific annealing thereby enhancing primer-template hybridization for sequence-specific amplification of nucleotides (see, e.g., PCT Publn. WO/2011/050278, incorporated herein by reference).

In a further aspect, a method of the embodiment further comprises: (a) contacting the sample with a second (or further) set of primers comprising a first primer comprising, from 5' to 3', (i) a reporter, (ii) a hairpin with a known melt point, (iii) a polymerase extension-blocking modification, (iv) at least one non-natural nucleotide, and (v) a target-specific sequence, complementary to a first region on the first strand of a second (or further) target nucleic acid; and a second primer comprising a sequence complementary to a region on a second strand of the second (or further) target nucleic acid; (b) amplifying the second target nucleic acid with the second set of primers (to obtain an amplification product), wherein said amplifying is performed in the presence of a quencher-labeled non-natural nucleotide, which base-pairs with the non-natural nucleotide of the first primer; and (c) detecting the presence of the second (or further) target nucleic acid by detecting a change in signal from the reporter on the first primer from the second (or further) set of primers. For example, detecting the presence of the first and/or second target nucleic acid may be performed sequentially or essentially simultaneously. In still a further aspect, the first and second set of primers may comprise distinguishable reporters. In another aspect, the first and second set of primers may comprise the same reporter and, in some cases, the first and second set of primers comprise hairpins with distinguishable melt points (e.g., melt points that differ by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C. from one another, or any range derivable therein).

In still a further aspect, the method is a multiplex method further comprising: (a) contacting the sample with a third, fourth, fifth, sixth, seventh, eighth, ninth, tenth, eleventh, twelfth, eighteenth, twenty-fourth, thirtieth, or thirty-sixth (or any range derivable therein) set of primers, each set of primers comprising a first primer comprising, from 5' to 3', (i) a reporter, (ii) a hairpin with a known melt point, (iii) a polymerase extension-blocking modification, (iv) at least one non-natural nucleotide, and (v) a target-specific sequence, complementary to a first region on the first strand of a third, fourth, fifth, sixth, seventh, eighth, ninth, tenth, eleventh, twelfth, eighteenth, twenty-fourth, thirtieth, or thirty-sixth (or any range derivable therein) target nucleic acid; and a second primer comprising a sequence complementary to a region on a second strand of the third, fourth, fifth or sixth target nucleic acid; (b) amplifying the third, fourth, fifth, sixth, seventh, eighth, ninth, tenth, eleventh, twelfth, eighteenth, twenty-fourth, thirtieth, or thirty-sixth (or any range derivable therein) target nucleic acid with the third, fourth, fifth, sixth, seventh, eighth, ninth, tenth, eleventh, twelfth, eighteenth, twenty-fourth, thirtieth, or thirty-sixth (or any range derivable therein) set of primers to obtain an amplification product, wherein said amplifying is performed in the presence of a quencher-labeled non-natural nucleotide, which base-pairs with the non-natural nucleotide of the first primer; and (c) detecting the presence of the third, fourth, fifth, sixth, seventh, eighth, ninth, tenth, eleventh, twelfth, eighteenth, twenty-fourth, thirtieth, or thirty-sixth (or any range derivable therein) target nucleic acid by detecting a change in signal from the reporter on the first primer from the third, fourth, fifth, sixth, seventh, eighth, ninth, tenth, eleventh, twelfth, eighteenth, twenty-fourth, thirtieth, or thirty-sixth (or any range derivable therein) set of primers. In one aspect, the first, second, third, fourth, fifth, sixth, seventh, eighth, ninth, tenth, eleventh, twelfth, eighteenth, twenty-fourth, thirtieth, and thirty-sixth (or any range derivable therein) set of primers each may comprise a distinguishable reporter or a hairpin with a distinguishable melt point. Thus, in some further aspects, a multiplex method according to the embodiments can comprise the use of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more distinct primer sets wherein each set of primers comprise either (1) a first primer having a hairpin with a distinguishable melt point or (2) a distinguishable reporter, such that the signal from each distinct set of primer may be individually discerned.

In still further aspects at least one set of primers for use according to the embodiments, comprises a second primer comprising at least one reporter-labeled non-natural nucleotide (e.g., to provide a second reporter signal for the primer set). For example, at least one the set of primers can comprise a first primer comprising, from 5' to 3', (i) a reporter, (ii) a hairpin with a known melt point, (iii) a polymerase extension-blocking modification, (iv) at least one non-natural nucleotide, and (v) a target-specific sequence, complementary to a first region on the first strand of a target nucleic acid; and a second primer comprising a sequence complementary to a region on a second strand of the target nucleic acid and at least one reporter-labeled non-natural nucleotide, wherein the melt point of an amplicon produced by the primers is distinguishable from the melt point of the hairpin of the first primer. Alternatively, or additionally, the second primer can comprise a sequence having at least one reporter-labeled non-natural nucleotide, wherein the reporter is different than the reporter of the first primer. Thus, such a primer set would produce a discernible change in signal as the temper is changes (1) over the melt point of the hair pin of the first primer and (2) over the melt point of the amplicon produced by the primers. Such an additional signal may be used to further confirm the presence of a target nucleic acid molecule.

Thus, in a further embodiment, a composition is provided comprising at least a first set of primers according to the embodiments. For example, a primer set may comprise a first primer comprising, from 5' to 3', (i) a reporter, (ii) a hairpin with a known melt point, (iii) a polymerase extension-blocking modification (which may form part of the hairpin), (iv) at least one non-natural nucleotide, and (v) a target-specific sequence, complementary to a first region on the first strand of a target nucleic acid; and a second primer comprising a sequence complementary to a region on a second strand of the target nucleic acid. In certain aspects, a second primer of a primer set according to the embodiments comprises and at least one reporter-labeled non-natural nucleotide. In some aspects, the composition further comprises a quencher-labeled non-natural nucleotide, a polymerase, a reference probe, a reference sample, and/or free nucleotides.

In still a further aspect, a composition further comprises a second (or further) set of primers comprising a first primer comprising, from 5' to 3', (i) a reporter, (ii) a hairpin with a known melt point, (iii) a polymerase extension-blocking modification, (iv) at least one non-natural nucleotide, and (v) a target-specific sequence, complementary to a first region on the first strand of a second target nucleic acid; and a second primer comprising a sequence complementary to a region on a second strand of the second target nucleic acid. In certain aspects, the first and second set of primers comprise distinguishable reporters and/or hairpins with distinguishable melt points. In some aspects, the composition comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more distinguishable sets of primers.

In a further embodiment, a kit is provided comprising (a) a first set of primers comprising a first primer comprising, from 5' to 3', (i) a reporter, (ii) a hairpin with a known melt point, (iii) a polymerase extension-blocking modification, (iv) at least one non-natural nucleotide, and (v) a target-specific sequence, complementary to a first region on the first strand of a target nucleic acid; and a second primer comprising a sequence complementary to a region on a second strand of the target nucleic acid; and (b) a quencher-labeled non-natural nucleotide. In a further aspect, the kit comprises at least two, three, four, five or six distinguishable sets of primers. In certain aspects, the sets of primers comprise distinguishable reporters or hairpins with distinguishable melt points. In some aspects, the kit further comprises a polymerase, a reference probe, free nucleotides, or instructions for use of the kit.

In a further embodiment, a method is provided for detecting the presence of a target nucleic acid in a sample comprising: (a) contacting the sample with a first set of probes, said set of probes comprising an upstream probe comprising, from 5' to 3', (i) at least one non-natural nucleotide labeled with a first member of a reporter-quencher pair (e.g., a reporter); (ii) a tag sequence; and (iii) a sequence complimentary to a first region on a first strand of the target nucleic acid; and a downstream probe comprising, from 5' to 3', (i) a mirrored tag sequence having the same sequence as the tag sequence of the upstream probe; and (ii) a sequence complimentary to a second region on a first strand of the target nucleic acid downstream of the first region, wherein the upstream probe comprises a 3' sequence of 3 or more bases complementary to the downstream probe such that when hybridized to the target nucleic acid the set of probes form a T-junction; (b) extending the upstream probe to synthesize sequences complementary to the mirrored tag sequence on the downstream probe to form an extended upstream probe; (c) allowing the extended upstream probe to hybridize to itself to form a hairpin probe; (d) extending the hairpin probe in the presence of a non-natural nucleotide labeled with a second member of a reporter-quencher pair (e.g., a quencher) that is capable of base-pairing with the at least one non-natural nucleotide in the upstream probe; and (e) detecting the target nucleic acid by detecting a change in signal from the label on the upstream probe and the hairpin probe. For example, in some aspects, the upstream probe comprises a 3' sequence of 3 to 10 bases (e.g., at least 3, 4, 5, 6, 7, 8 or 9 bases) complementary to the downstream probe, such as complementary the tag sequence of the downstream probe. In further aspects, the downstream probe further comprises (iii) a isoprimer complement sequence including one or more non-natural bases between the mirrored tag sequence having the same sequence as the tag sequence of the upstream probe and the sequence complimentary to a second region on a first strand of the target nucleic acid downstream of the first region. Thus, in some aspects, the upstream probe comprises a 3' sequence of 3 to 10 bases (e.g., at least 3, 4, 5, 6, 7, 8 or 9 bases) complementary to the isoprimer complement sequence of the downstream probe. In certain aspects, before being extended the upstream and downstream probes have a melt point of less than 60, 59, 58, 57, 56, 55, 54, 53, 52, 51 or 50° C. in the absence of the target nucleic acid.

Thus, in a more specific embodiment a method is provided for detecting the presence of one or both of a first and second target nucleic acid molecule in a sample comprising: (a) contacting the sample with a second set of probes comprising an upstream probe comprising, from 5' to 3', (i) at least one non-natural nucleotide labeled with a first member of a reporter-quencher pair; (ii) a tag sequence; and (iii) a sequence complimentary to a first region on a first strand of a second target nucleic acid; and a downstream probe comprising, from 5' to 3', (i) a mirrored tag sequence having the same sequence as the tag sequence of the upstream probe; and (ii) a sequence complimentary to a second region on a first strand of the second target nucleic acid downstream of the first region, wherein the upstream probe comprises a 3' sequence of 3 or more bases complementary to the downstream probe such that when hybridized to the target nucleic acid the set of probes form a T-junction; (b) extending the upstream probe to synthesize sequences complementary to the mirrored tag sequence on the downstream probe to form an extended upstream probe; (c) allowing the extended upstream probe to hybridize to itself to form a hairpin probe; (d) extending the hairpin probe in the presence of a non-natural nucleotide labeled with a second member of a reporter-quencher pair that is capable of base-pairing with the at least one non-natural nucleotide in the upstream probe; and (e) detecting the second target nucleic acid by detecting a change in signal from the label on the upstream probe and the hairpin probe. (e.g., based on the different melt points of the hairpin probes from the first and second probe sets). For example, detecting the presence of the first and/or second target nucleic acid may be performed sequentially or essentially simultaneously. In still a further aspect, the first and second set of probes may comprise distinguishable reporters. In another aspect, the first and second set of probes may comprise the same reporter and, in some cases, the first and second set of probes form hairpin probes with distinguishable melt points (e.g., melt points that differ by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C. from one another, or any range derivable therein).

In still a further aspect, the method is a multiplex method further comprising: (a) contacting the sample with a third, fourth, fifth, sixth, seventh, eighth, ninth, tenth, eleventh, twelfth, eighteenth, twenty-fourth, thirtieth, or thirty-sixth (or any range derivable therein) set of probes, each set of probes comprising an upstream probe comprising, from 5' to 3', (i) at least one non-natural nucleotide labeled with a first member of a reporter-quencher pair; (ii) a tag sequence; and (iii) a sequence complimentary to a first region on a first strand of a third, fourth, fifth, sixth, seventh, eighth, ninth, tenth, eleventh, twelfth, eighteenth, twenty-fourth, thirtieth, or thirty-sixth (or any range derivable therein) target nucleic acid; and a downstream probe comprising, from 5' to 3', (i) a mirrored tag sequence having the same sequence as the tag sequence of the upstream probe; and (ii) a sequence complimentary to a second region on a first strand of the third, fourth, fifth, sixth, seventh, eighth, ninth, tenth, eleventh, twelfth, eighteenth, twenty-fourth, thirtieth, or thirty-sixth (or any range derivable therein) target nucleic acid downstream of the first region, wherein the upstream probe comprises a 3' sequence of 3 or more bases complementary to the downstream probe such that when hybridized to the target nucleic acid the set of probes form a T-junction; (b) extending the upstream probe to synthesize sequences complementary to the mirrored tag sequence on the downstream probe to form an extended upstream probe; (c) allowing the extended upstream probe to hybridize to itself to form a hairpin probe; (d) extending the hairpin probe in the presence of a non-natural nucleotide labeled with a second member of a reporter-quencher pair that is capable of base-pairing with the at least one non-natural nucleotide in the upstream probe; and (e) detecting the a third, fourth, fifth, sixth, seventh, eighth, ninth, tenth, eleventh, twelfth, eighteenth, twenty-fourth, thirtieth, or thirty-sixth (or any range derivable therein) target nucleic acid by detecting a change in signal from the label on the upstream probe and the hairpin probe. In some aspects, a multiplex method of the embodiments comprises probes sets having one, two, three, four, five or six distinguishable reports and/or probe sets that form hairpin probes having one, two, three, four, five or six distinguishable melt temperatures. Thus, in some aspects, a multiplex method of the embodiments can be used to detect (e.g., in the same reaction) 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 different target nucleic acid sequences.

In certain aspects, the reporter for use in the instant embodiments may be a fluorophore, such as a fluorophore attached (e.g., at the 5' end) to the first probe. Accordingly, in some cases, a change is the signal may be a decrease in a fluorescent signal In further aspects, detecting a change in signal from the reporter may comprise detecting the change (or rate of change) in signal, such as unquenching of a signal as the temperature of the sample is changed. In one aspect, the temperature of the sample may be increased above (or decreased below) the melt point of the hairpin of one more of the probes in the sample. In the case where two or more probe sets are present, changing the temperature of a sample may comprise increasing the temperature of the sample from a temperature that is below the melt point of the hairpins of both of the first probe and the second probe to a temperature that is above the melt point of both of the hairpin probes.

Thus, in a further embodiment, a composition is provided comprising a first set of probes, said set of probes comprising an upstream probe comprising, from 5' to 3', (i) at least one non-natural nucleotide labeled with a first member of a reporter-quencher pair; (ii) a tag sequence; and (iii) a sequence complimentary to a first region on a first strand of the target nucleic acid; and a downstream probe comprising, from 5' to 3', (i) a mirrored tag sequence having the same sequence as the tag sequence of the upstream probe; and (ii) a sequence complimentary to a second region on a first strand of the target nucleic acid downstream of the first region, wherein the upstream probe comprises a 3' sequence of 3 or more bases complementary to the downstream probe such that when hybridized to the target nucleic acid the set of probes form a T-junction.

In still a further aspect, a composition further comprises a second (or further) set of probes comprising an upstream probe comprising, from 5' to 3', (i) at least one non-natural nucleotide labeled with a first member of a reporter-quencher pair; (ii) a tag sequence; and (iii) a sequence complimentary to a first region on a first strand of a second target nucleic acid; and a downstream probe comprising, from 5' to 3', (i) a mirrored tag sequence having the same sequence as the tag sequence of the upstream probe; and (ii) a sequence complimentary to a second region on a first strand of the second target nucleic acid downstream of the first region, wherein the upstream probe comprises a 3' sequence of 3 or more bases complementary to the downstream probe such that when hybridized to the target nucleic acid the set of probes form a T-junction. In certain aspects, the first and second set of probes comprise distinguishable reporters and/or form hairpins probes with distinguishable melt points. In some aspects, the composition comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more distinguishable sets of probes.

In a further embodiment, a kit is provided comprising (a) a first set of probes, said set of probes comprising an upstream probe comprising, from 5' to 3', (i) at least one non-natural nucleotide labeled with a first member of a reporter-quencher pair; (ii) a tag sequence; and (iii) a sequence complimentary to a first region on a first strand of the target nucleic acid; and a downstream probe comprising, from 5' to 3', (i) a mirrored tag sequence having the same sequence as the tag sequence of the upstream probe; and (ii) a sequence complimentary to a second region on a first strand of the target nucleic acid downstream of the first region, wherein the upstream probe comprises a 3' sequence of 3 or more bases complementary to the downstream probe such that when hybridized to the target nucleic acid the set of probes form a T-junction; and (b) a reporter-labeled or quencher-labeled non-natural nucleotide. In a further aspect, the kit comprises at least two, three, four, five or six distinguishable sets of probes. In certain aspects, the sets of probes comprise distinguishable reporters or form hairpin probes with distinguishable melt points. In some aspects, the kit further comprises a polymerase, a reference probe, free nucleotides, or instructions for use of the kit.

In still a further embodiment, a method is provided for detecting the presence of a target nucleic acid in a sample comprising: (a) contacting the sample with a first set of probes, said set of probes comprising an upstream probe comprising, from 5' to 3', (i) a tag sequence comprising at least one non-natural nucleotide labeled with a first member of a reporter-quencher pair; and (ii) a sequence complimentary to a first region on a first strand of the target nucleic acid; and a downstream probe comprising, from 5' to 3', (i) a mirrored tag sequence having the same sequence as the tag sequence of the upstream probe and including at least a first un-labeled non-natural nucleotide; and (ii) a sequence complimentary to a second region on a first strand of the target nucleic acid downstream of the first region, wherein the upstream probe comprises a 3' sequence of 3 or more bases complementary to the downstream probe such that when hybridized to the target nucleic acid the set of probes form a T-junction; (b) extending the upstream probe in the presence of a non-natural nucleotide labeled with a second member of a reporter-quencher pair that is capable of base-pairing with the at least one non-natural nucleotide in the upstream probe to synthesize sequences complementary to the mirrored tag sequence on the downstream probe to form an extended upstream probe; (c) allowing the extended upstream probe to hybridize to itself to form a hairpin probe; and (d) detecting the target nucleic acid by detecting a change in signal from the label on the upstream probe and the hairpin probe. In some aspects, the upstream probe comprises a 3' sequence of 3 to 10 bases (e.g., at least 3, 4, 5, 6, 7, 8 or 9 bases) complementary to the downstream probe, such as complementary the tag sequence of the downstream probe. In further aspects, the downstream probe further comprises (iii) a isoprimer complement sequence including one or more non-natural bases, located between the mirrored tag sequence having the same sequence as the tag sequence of the upstream probe and including at least a first un-labeled non-natural nucleotide and the sequence complimentary to a second region on a first strand of the target nucleic acid downstream of the first region. Thus, in some aspects, the upstream probe comprises a 3' sequence of 3 to 10 bases (e.g., at least 3, 4, 5, 6, 7, 8 or 9 bases) complementary to the isoprimer complement sequence of the downstream probe. In certain aspects, before being extended the upstream and downstream probes have a melt point of less than 60, 59, 58, 57, 56, 55, 54, 53, 52, 51 or 50° C. in the absence of the target nucleic acid.

Thus, in further embodiment a method is provided for detecting the presence of one or both of a first and second target nucleic acid molecule in a sample further comprising: (a) contacting the sample with a second set of probes, said set of probes comprising an upstream probe comprising, from 5' to 3', (i) a tag sequence comprising at least one non-natural nucleotide labeled with a first member of a reporter-quencher pair; and (ii) a sequence complimentary to a first region on a first strand of a second target nucleic acid; and a downstream probe comprising, from 5' to 3', (i) a mirrored tag sequence having the same sequence as the tag sequence of the upstream probe and including at least a first un-labeled non-natural nucleotide; and (ii) a sequence complimentary to a second region on a first strand of the second target nucleic acid downstream of the first region, wherein the upstream probe comprises a 3' sequence of 3 or more bases complementary to the downstream probe such that when hybridized to the target nucleic acid the set of probes form a T-junction; (b) extending the upstream probe in the presence of a non-natural nucleotide labeled with a second member of a reporter-quencher pair that is capable of base-pairing with the at least one non-natural nucleotide in the upstream probe to synthesize sequences complementary to the mirrored tag sequence on the downstream probe and form an extended upstream probe; (c) allowing the extended upstream probe to hybridize to itself to form a hairpin probe; and (d) detecting the second target nucleic acid by detecting a change in signal from the label on the upstream probe and the hairpin probe (e.g., based on the different melt points of the hairpin probes from the first and second probe sets). For example, detecting the presence of the first and/or second target nucleic acid may be performed sequentially or essentially simultaneously. In still a further aspect, the first and second set of probes may comprise distinguishable reporters. In another aspect, the first and second set of probes may comprise the same reporter and, in some cases, the first and second set of probes form hairpin probes with distinguishable melt points (e.g., melt points that differ by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C. from one another, or any range derivable therein).

In still a further aspect, the method is a multiplex method further comprising: (a) contacting the sample with a third, fourth, fifth, sixth, seventh, eighth, ninth, tenth, eleventh, twelfth, eighteenth, twenty-fourth, thirtieth, or thirty-sixth (or any range derivable therein) set of probes set of probes, said set of probes comprising an upstream probe comprising, from 5' to 3', (i) a tag sequence comprising at least a first reporter-labeled non-natural nucleotide; and (ii) a sequence complimentary to a first region on a first strand of a third, fourth, fifth, sixth, seventh, eighth, ninth, tenth, eleventh, twelfth, eighteenth, twenty-fourth, thirtieth, or thirty-sixth (or any range derivable therein) target nucleic acid; and a downstream probe comprising, from 5' to 3', (i) a mirrored tag sequence having the same sequence as the tag sequence of the upstream probe and including at least a first un-labeled non-natural nucleotide; and (ii) a sequence complimentary to a second region on a first strand of the third, fourth, fifth, sixth, seventh, eighth, ninth, tenth, eleventh, twelfth, eighteenth, twenty-fourth, thirtieth, or thirty-sixth (or any range derivable therein) target nucleic acid downstream of the first region, wherein the upstream probe comprises a 3' sequence of 3 or more bases complementary to the downstream probe such that when hybridized to the target nucleic acid the set of probes form a T-junction; (b) extending the upstream probe in the presence of a non-natural nucleotide labeled with a second member of a reporter-quencher pair that is capable of base-pairing with the at least one non-natural nucleotide in the upstream probe to synthesize sequences complementary to the mirrored tag sequence on the downstream probe and form an extended upstream probe; (c) allowing the extended upstream probe to hybridize to itself to form a hairpin probe; and (d) detecting the third, fourth, fifth, sixth, seventh, eighth, ninth, tenth, eleventh, twelfth, eighteenth, twenty-fourth, thirtieth, or thirty-sixth (or any range derivable therein) target nucleic acid by detecting a change in signal from the label on the upstream probe and the hairpin probe. In some aspects, a multiplex method of the embodiments comprises probes sets having one, two, three, four, five or six distinguishable reports and/or probe sets that form hairpin probes having one, two, three, four, five or six distinguishable melt temperatures. Thus, in some aspects, a multiplex method of the embodiments can be used to detect (e.g., in the same reaction) 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 different target nucleic acid sequences.

In certain aspects, the reporter for use in the instant embodiments may be a fluorophore, such as a fluorophore attached (e.g., at the 5' end) to the first probe. Accordingly, in some cases, a change is the signal may be a decrease in a fluorescent signal.

In further aspects, detecting a change in signal from the reporter may comprise detecting the change (or rate of change) in signal, such as unquenching of a signal as the temperature of the sample is changed. In one aspect, the temperature of the sample may be increased above (or decreased below) the melt point of the hairpin of one more of the probes in the sample. In the case where two or more probe sets are present, changing the temperature of a sample may comprise increasing the temperature of the sample from a temperature that is below the melt point of the hairpins of both of the first probe and the second probe to a temperature that is above the melt point of both of the hairpin probes.

Thus, in a further embodiment, a composition is provided comprising an upstream probe comprising, from 5' to 3', (i) a tag sequence comprising at least one non-natural nucleotide labeled with a first member of a reporter-quencher pair; and (ii) a sequence complimentary to a first region on a first strand of the target nucleic acid; and a downstream probe comprising, from 5' to 3', (i) a mirrored tag sequence having the same sequence as the tag sequence of the upstream probe and including at least a first un-labeled non-natural nucleotide; and (ii) a sequence complimentary to a second region on a first strand of the target nucleic acid downstream of the first region, wherein the upstream probe comprises a 3' sequence of 3 or more bases complementary to the downstream probe such that when hybridized to the target nucleic acid the set of probes form a T-junction.

In still a further aspect, a composition further comprises a second (or further) set of probes comprising an upstream probe comprising, from 5' to 3', (i) a tag sequence comprising at least one non-natural nucleotide labeled with a first member of a reporter-quencher pair; and (ii) a sequence complimentary to a first region on a first strand of a second target nucleic acid; and a downstream probe comprising, from 5' to 3', (i) a mirrored tag sequence having the same sequence as the tag sequence of the upstream probe and including at least a first un-labeled non-natural nucleotide; and (ii) a sequence complimentary to a second region on a first strand of the second target nucleic acid downstream of the first region, wherein the upstream probe comprises a 3' sequence of 3 or more bases complementary to the downstream probe such that when hybridized to the target nucleic acid the set of probes form a T-junction. In certain aspects, the first and second set of probes comprise distinguishable reporters and/or form hairpins probes with distinguishable melt points. In some aspects, the composition comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more distinguishable sets of probes.

In a further embodiment, a kit is provided comprising (a) a first set of probes, said set of probes comprising an upstream probe comprising, from 5' to 3', (i) a tag sequence comprising at least one non-natural nucleotide labeled with a first member of a reporter-quencher pair; and (ii) a sequence complimentary to a first region on a first strand of the target nucleic acid; and a downstream probe comprising, from 5' to 3', (i) a mirrored tag sequence having the same sequence as the tag sequence of the upstream probe and including at least a first un-labeled non-natural nucleotide; and (ii) a sequence complimentary to a second region on a first strand of the target nucleic acid downstream of the first region, wherein the upstream probe comprises a 3' sequence of 3 or more bases complementary to the downstream probe such that when hybridized to the target nucleic acid the set of probes form a T-junction; and (b) a reporter-labeled or quencher-labeled non-natural nucleotide. In a further aspect, the kit comprises at least two, three, four, five or six distinguishable sets of probes. In certain aspects, the sets of probes comprise distinguishable reporters or form hairpin probes with distinguishable melt points. In some aspects, the kit further comprises a polymerase, a reference probe, free nucleotides, or instructions for use of the kit.

In still a further embodiment, a method is provided for detecting the presence of a target nucleic acid in a sample comprising: (a) contacting the sample with a first set of probes, said set of probes comprising an upstream probe comprising, from 5' to 3', (i) at least a first non-natural nucleotide labeled with a first member of a reporter-quencher pair; and (ii) a sequence complimentary to a first region on a first strand of the target nucleic acid; and a downstream probe comprising, from 5' to 3', (i) a hairpin tag comprising a tag sequence and the reverse complement of the tag sequence, such that the sequence form a hairpin; and (ii) a sequence complimentary to a second region on a first strand of the target nucleic acid downstream of the first region, wherein the upstream probe comprises a 3' sequence of 3 or more bases complementary to the downstream probe such that when hybridized to the target nucleic acid the set of probes form a T-junction; (b) extending the upstream probe to synthesize sequences complementary to the hairpin tag sequence on the downstream probe and form an extended upstream probe; (c) allowing the upstream probe to hybridize to itself to form a hairpin probe; (d) extending the hairpin probe in the presence of non-natural nucleotide labeled with a second member of a reporter-quencher pair that is capable of base-pairing with the at least one non-natural nucleotide in the upstream probe; and (e) detecting the target nucleic acid by detecting a change in signal from the label on the upstream probe and the hairpin probe. In some aspects, the upstream probe comprises a 3' sequence of 3 to 10 bases (e.g., at least 3, 4, 5, 6, 7, 8 or 9 bases) complementary to the downstream probe, such as complementary the tag sequence of the downstream probe. In further aspects, the downstream probe further comprises (iii) a isoprimer complement sequence including one or more non-natural bases, located between the mirrored tag sequence having the same sequence as the tag sequence of the upstream probe and including at least a first un-labeled non-natural nucleotide and the sequence complimentary to a second region on a first strand of the target nucleic acid downstream of the first region. Thus, in some aspects, the upstream probe comprises a 3' sequence of 3 to 10 bases (e.g., at least 3, 4, 5, 6, 7, 8 or 9 bases) complementary to the isoprimer complement sequence of the downstream probe. In certain aspects, before being extended the upstream and downstream probes have a melt point of less than 60, 59, 58, 57, 56, 55, 54, 53, 52, 51 or 50° C. in the absence of the target nucleic acid.

Thus, in further embodiment a method is provided for detecting the presence of one or both of a first and second target nucleic acid molecule in a sample further comprising: (a) contacting the sample with a second set of probes comprising an upstream probe comprising, from 5' to 3', (i) at least a first non-natural nucleotide labeled with a first member of a reporter-quencher pair; and (ii) a sequence complimentary to a first region on a first strand of a second target nucleic acid; and a downstream probe comprising, from 5' to 3', (i) a hairpin tag comprising a tag sequence and the reverse complement of the tag sequence, such that the sequence form a hairpin; and (ii) a sequence complimentary to a second region on a first strand of the second target nucleic acid downstream of the first region, wherein the upstream probe comprises a 3' sequence of 3 or more bases complementary to the downstream probe such that when hybridized to the target nucleic acid the set of probes form a T-junction; (b) extending the upstream probe to synthesize sequences complementary to the hairpin tag sequence on the downstream probe and form an extended upstream probe; (c) allowing the extended upstream probe to hybridize to itself to form a hairpin probe; (d) extending the hairpin probe in the presence of a non-natural nucleotide labeled with a first member of a reporter-quencher pair that is capable of base-pairing with the at least one non-natural nucleotide in the upstream probe; and (e) detecting the second target nucleic acid by detecting a change in signal from the label on the upstream probe and the hairpin probe. (e.g., based on the different melt points of the hairpin probes from the first and second probe sets). For example, detecting the presence of the first and/or second target nucleic acid may be performed sequentially or essentially simultaneously. In still a further aspect, the first and second set of probes may comprise distinguishable reporters. In another aspect, the first and second set of probes may comprise the same reporter and, in some cases, the first and second set of probes form hairpin probes with distinguishable melt points (e.g., melt points that differ by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C. from one another, or any range derivable therein).

In still a further aspect, the method is a multiplex method further comprising: (a) contacting the sample with a third, fourth, fifth, sixth, seventh, eighth, ninth, tenth, eleventh, twelfth, eighteenth, twenty-fourth, thirtieth, or thirty-sixth (or any range derivable therein) set of probes, each set of probes comprising an upstream probe comprising, from 5' to 3', (i) at least a first non-natural nucleotide labeled with a first member of a reporter-quencher pair; and (ii) a sequence complimentary to a first region on a first strand of a third, fourth, fifth, sixth, seventh, eighth, ninth, tenth, eleventh, twelfth, eighteenth, twenty-fourth, thirtieth, or thirty-sixth (or any range derivable therein) target nucleic acid; and a downstream probe comprising, from 5' to 3', (i) a hairpin tag comprising a tag sequence and the reverse complement of the tag sequence, such that the sequence form a hairpin; and (ii) a sequence complimentary to a second region on a first strand of the third, fourth, fifth, sixth, seventh, eighth, ninth, tenth, eleventh, twelfth, eighteenth, twenty-fourth, thirtieth, or thirty-sixth (or any range derivable therein) target nucleic acid downstream of the first region, wherein the upstream probe comprises a 3' sequence of 3 or more bases complementary to the downstream probe such that when hybridized to the target nucleic acid the set of probes form a T-junction; (b) extending the upstream probe to synthesize sequences complementary to the hairpin tag sequence on the downstream probe and form an extended upstream probe; (c) allowing the extended upstream probe to hybridize to itself to form a hairpin probe; (d) extending the hairpin probe in the presence of a non-natural nucleotide labeled with a first member of a reporter-quencher pair that is capable of base-pairing with the at least one non-natural nucleotide in the upstream probe; and (e) detecting the third, fourth, fifth, sixth, seventh, eighth, ninth, tenth, eleventh, twelfth, eighteenth, twenty-fourth, thirtieth, or thirty-sixth (or any range derivable therein) target nucleic acid by detecting a change in signal from the label on the upstream probe and the hairpin probe. In some aspects, a multiplex method of the embodiments comprises probes sets having one, two, three, four, five or six distinguishable reports and/or probe sets that form hairpin probes having one, two, three, four, five or six distinguishable melt temperatures. Thus, in some aspects, a multiplex method of the embodiments can be used to detect (e.g., in the same reaction) 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 different target nucleic acid sequences.

In certain aspects, the reporter for use in the instant embodiments may be a fluorophore, such as a fluorophore attached (e.g., at the 5' end) to the first probe. Accordingly, in some cases, a change is the signal may be a decrease in a fluorescent signal.

In further aspects, detecting a change in signal from the reporter may comprise detecting the change (or rate of change) in signal, such as unquenching of a signal as the temperature of the sample is changed. In one aspect, the temperature of the sample may be increased above (or decreased below) the melt point of the hairpin of one more of the probes in the sample. In the case where two or more probe sets are present, changing the temperature of a sample may comprise increasing the temperature of the sample from a temperature that is below the melt point of the hairpins of both of the first probe and the second probe to a temperature that is above the melt point of both of the hairpin probes.

Thus, in a further embodiment, a composition is provided comprising a first set of probes, said set of probes comprising an upstream probe comprising, from 5' to 3', (i) at least a first non-natural nucleotide labeled with a first member of a reporter-quencher pair; and (ii) a sequence complimentary to a first region on a first strand of the target nucleic acid; and a downstream probe comprising, from 5' to 3', (i) a hairpin tag comprising a tag sequence and the reverse complement of the tag sequence, such that the sequence form a hairpin; and (ii) a sequence complimentary to a second region on a first strand of the target nucleic acid downstream of the first region, wherein the upstream probe comprises a 3' sequence of 3 or more bases complementary to the downstream probe such that when hybridized to the target nucleic acid the set of probes form a T-junction.

In still a further aspect, a composition further comprises a second (or further) set of probes comprising an upstream probe comprising, from 5' to 3', (i) at least a first non-natural nucleotide labeled with a first member of a reporter-quencher pair; and (ii) a sequence complimentary to a first region on a first strand of a second target nucleic acid; and a downstream probe comprising, from 5' to 3', (i) a hairpin tag comprising a tag sequence and the reverse complement of the tag sequence, such that the sequence form a hairpin; and (ii) a sequence complimentary to a second region on a first strand of the second target nucleic acid downstream of the first region, wherein the upstream probe comprises a 3' sequence of 3 or more bases complementary to the downstream probe such that when hybridized to the target nucleic acid the set of probes form a T-junction. In certain aspects, the first and second set of probes comprise distinguishable reporters and/or form hairpins probes with distinguishable melt points. In some aspects, the composition comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more distinguishable sets of probes.

In a further embodiment, a kit is provided comprising (a) a first set of probes, said set of probes comprising an upstream probe comprising, from 5' to 3', (i) at least a first non-natural nucleotide labeled with a first member of a reporter-quencher pair; and (ii) a sequence complimentary to a first region on a first strand of the target nucleic acid; and a downstream probe comprising, from 5' to 3', (i) a hairpin tag comprising a tag sequence and the reverse complement of the tag sequence, such that the sequence form a hairpin; and (ii) a sequence complimentary to a second region on a first strand of the target nucleic acid downstream of the first region, wherein the upstream probe comprises a 3' sequence of 3 or more bases complementary to the downstream probe such that when hybridized to the target nucleic acid the set of probes form a T-junction; and (b) a reporter-labeled or quencher-labeled non-natural nucleotide. In a further aspect, the kit comprises at least two, three, four, five or six distinguishable sets of probes. In certain aspects, the sets of probes comprise distinguishable reporters or form hairpin probes with distinguishable melt points. In some aspects, the kit further comprises a polymerase, a reference probe, free nucleotides, or instructions for use of the kit.

In still a further embodiment, a method is provided for detecting the presence of a target nucleic acid in a sample comprising: (a) contacting the sample with at least a first set of primers, comprising a first primer comprising, from 5' to 3', (i) a tag sequence comprising at least one un-labeled non-natural nucleotide; and (ii) a target-specific sequence, complementary to a first region on the second strand of a target nucleic acid; and a second primer comprising a sequence complementary to a region on a first strand of the target nucleic acid; (b) amplifying the target nucleic acid with the primers to produce an amplified sample; (c) contacting the amplified sample with a probe comprising, from 5' to 3', (i) a tag sequence identical to the tag sequence of the first primer and comprising at least one non-natural nucleotide labeled with a first member of a reporter-quencher pair; and (ii) a sequence that is complimentary to a first region on a first strand of the target nucleic acid; (d) extending the probe in the presence of a non-natural nucleotide labeled with a second member of a reporter-quencher pair that is capable of base-pairing with the at least one un-labeled non-natural nucleotide in the in the first primer to form an extended probe; and (e) allowing the extended probe to hybridize to itself to form a hairpin probe; (f) detecting the target nucleic acid by detecting a change in signal from the label on the probe and the hairpin probe. In certain aspects, the probe further comprises (iii) a polymerase extension blocking modification between the tag sequence and the sequence that is complimentary to a first region on a first strand of the target nucleic acid.

Thus, in further embodiment a method is provided for detecting the presence of one or both of a first and second target nucleic acid molecule in a sample further comprising: (a) contacting the sample with at least a second set of primers, comprising a first primer comprising, from 5' to 3', (i) a tag sequence comprising at least one un-labeled non-natural nucleotide; and (ii) a target-specific sequence, complementary to a first region on the second strand of a second target nucleic acid; and a second primer comprising a sequence complementary to a region on a first strand of the second target nucleic acid; (b) amplifying the target nucleic acid with the primers to produce an amplified sample; (c) contacting the amplified sample with a second probe comprising, from 5' to 3', (i) a tag sequence identical to the tag sequence of the first primer and comprising at least one non-natural nucleotide labeled with a first member of a reporter-quencher pair; and (ii) a sequence that is complimentary to a first region on a first strand of the second target nucleic acid; (d) extending the probe in the presence of a non-natural nucleotide labeled with a second member of a reporter-quencher pair that is capable of base-pairing with the at least one un-labeled non-natural nucleotide in the in the first primer to form an extended probe; and (e) allowing the extended probe to hybridize to itself to form a hairpin probe; (f) detecting the second target nucleic acid by detecting a change in signal from the label on the probe and the hairpin probe (e.g., based on the different melt points of the hairpin probes from the first and second probes). For example, detecting the presence of the first and/or second target nucleic acid may be performed sequentially or essentially simultaneously. In still a further aspect, the first and second probes may comprise distinguishable reporters. In another aspect, the first and second probes may comprise the same reporter and, in some cases, the first and second set of probes form hairpin probes with distinguishable melt points (e.g., melt points that differ by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C. from one another, or any range derivable therein).

a third, fourth, fifth, sixth, seventh, eighth, ninth, tenth, eleventh, twelfth, eighteenth, twenty-fourth, thirtieth, or thirty-sixth (or any range derivable therein)

In still a further aspect, the method is a multiplex method further comprising: (a) contacting the sample with a third, fourth, fifth, sixth, seventh, eighth, ninth, tenth, eleventh, twelfth, eighteenth, twenty-fourth, thirtieth, or thirty-sixth (or any range derivable therein) set of primers, comprising a first primer comprising, from 5' to 3', (i) a tag sequence comprising at least one un-labeled non-natural nucleotide; and (ii) a target-specific sequence, complementary to a first region on the second strand of a third, fourth, fifth, sixth, seventh, eighth, ninth, tenth, eleventh, twelfth, eighteenth, twenty-fourth, thirtieth, or thirty-sixth (or any range derivable therein) target nucleic acid; and a second primer comprising a sequence complementary to a region on a first strand of the third, fourth, fifth, sixth, seventh, eighth, ninth, tenth, eleventh, twelfth, eighteenth, twenty-fourth, thirtieth, or thirty-sixth (or any range derivable therein) target nucleic acid; (b) amplifying the target nucleic acid with the primers to produce an amplified sample; (c) contacting the amplified sample with a third, fourth, fifth, sixth, seventh, eighth, ninth, tenth, eleventh, twelfth, eighteenth, twenty-fourth, thirtieth, or thirty-sixth (or any range derivable therein) probe comprising, from 5' to 3', (i) a tag sequence identical to the tag sequence of the first primer and comprising at least one non-natural nucleotide labeled with a first member of a reporter-quencher pair; and (ii) a sequence that is complimentary to a first region on a first strand of the third, fourth, fifth, sixth, seventh, eighth, ninth, tenth, eleventh, twelfth, eighteenth, twenty-fourth, thirtieth, or thirty-sixth (or any range derivable therein) target nucleic acid; (d) extending the probe in the presence of a non-natural nucleotide labeled with a second member of a reporter-quencher pair that is capable of base-pairing with the at least one un-labeled non-natural nucleotide in the in the first primer to form an extended probe; and (e) allowing the extended probe to hybridize to itself to form a hairpin probe; (f) detecting the third, fourth, fifth, sixth, seventh, eighth, ninth, tenth, eleventh, twelfth, eighteenth, twenty-fourth, thirtieth, or thirty-sixth (or any range derivable therein) target nucleic acid by detecting a change in signal from the label on the probe and the hairpin probe. In some aspects, a multiplex method of the embodiments comprises probes having one, two, three, four, five or six distinguishable reports and/or probes that form hairpin probes having one, two, three, four, five or six distinguishable melt temperatures. Thus, in some aspects, a multiplex method of the embodiments can be used to detect (e.g., in the same reaction) 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 different target nucleic acid sequences.

In certain aspects, the reporter for use in the instant embodiments may be a fluorophore, such as a fluorophore attached (e.g., at the 5' end) to the probe. Accordingly, in some cases, a change is the signal may be a decrease in a fluorescent signal.

In further aspects, detecting a change in signal from the reporter may comprise detecting the change (or rate of change) in signal, such as unquenching of a signal as the temperature of the sample is changed. In one aspect, the temperature of the sample may be increased above (or decreased below) the melt point of the hairpin of one more of the probes in the sample. In the case where two or more probe sets are present, changing the temperature of a sample may comprise increasing the temperature of the sample from a temperature that is below the melt point of the hairpins of both of the first probe and the second probe to a temperature that is above the melt point of both of the hairpin probes.

Thus, in a further embodiment, a composition is provided comprising a first primers comprising, from 5' to 3', (i) a tag sequence comprising at least one un-labeled non-natural nucleotide; and (ii) a target-specific sequence, complementary to a first region on the second strand of a target nucleic acid; and a second primer comprising a sequence complementary to a region on a first strand of the target nucleic acid; and a probe comprising, from 5' to 3', (i) a tag sequence identical to the tag sequence of the first primer and comprising at least one non-natural nucleotide labeled with a first member of a reporter-quencher pair; and (ii) a sequence that is complimentary to a first region on a first strand of the target nucleic acid.

In still a further aspect, a composition further comprises a second (or further) set of primers and probes comprising a first primer comprising, from 5' to 3', (i) a tag sequence comprising at least one un-labeled non-natural nucleotide; and (ii) a target-specific sequence, complementary to a first region on the second strand of a second target nucleic acid; and a second primer comprising a sequence complementary to a region on a first strand of the second target nucleic acid; and a second probe comprising, from 5' to 3', (i) a tag sequence identical to the tag sequence of the first primer and comprising at least one non-natural nucleotide labeled with a first member of a reporter-quencher pair; and (ii) a sequence that is complimentary to a first region on a first strand of the second target nucleic acid. In certain aspects, the first and second (or further) probes comprise distinguishable reporters and/or form hairpins probes with distinguishable melt points. In some aspects, the composition comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more distinguishable probes.

In a further embodiment, a kit is provided comprising (a) a first set of primers, comprising a first primer comprising, from 5' to 3', (i) a tag sequence comprising at least one un-labeled non-natural nucleotide; and (ii) a target-specific sequence, complementary to a first region on the second strand of a target nucleic acid; and a second primer comprising a sequence complementary to a region on a first strand of the target nucleic acid; (b) a probe comprising, from 5' to 3', (i) a tag sequence identical to the tag sequence of the first primer and comprising at least one non-natural nucleotide labeled with a first member of a reporter-quencher pair; and (ii) a sequence that is complimentary to a first region on a first strand of the target nucleic acid; and (c) a reporter-labeled or quencher-labeled non-natural nucleotide. In certain aspects, the probes comprise distinguishable reporters or form hairpin probes with distinguishable melt points. In some aspects, the kit further comprises a polymerase, a reference probe, free nucleotides, or instructions for use of the kit.

In still a further embodiment, a method is provided for detecting the presence of at least a first target nucleic acid comprising: (a) contacting the sample with a first target-specific primer-probe set, the primer-probe set comprising (i) a primer complementary to a first region on a first strand of the target nucleic acid; (ii) a target-specific probe complementary to a second region on the first strand of the target nucleic acid downstream of the first region and comprising a 5' tag sequence, which is not complementary to the target nucleic acid; (iii) a first assay probe comprising a first region which is complementary to the tag sequence from the target-specific probe and second region, downstream of the first region; and (iv) a second assay probe complimentary to the second region of the first assay probe, wherein one of the first and second assay probes is labeled with a reporter and the other is labeled with a quencher; (b) incubating the sample under conditions suitable for hybridization of the target nucleic acid with the target-specific primer and the target-specific probe; (c) cleaving the hybridized target-specific probe with a nucleic acid polymerase having exonuclease activity to release the tag sequence from the target-specific probe; (d) hybridizing the released tag sequence with the first assay probe; (e) extending the hybridized tag sequence along the first assay probe and cleaving the second assay probe hybridized to the first assay probe; and (f) detecting at least a first target nucleic acid by detecting a change of signal (e.g., unquenching) from the reporter on the first or second assay probe. In certain aspects, detecting a change in signal from the reporter comprises detecting a reduction or elimination of a melt peak corresponding to the assay probe indicating that the second assay probe was cleaved and indicating the presence of the target nucleic acid. In further aspects, one or more of the components (i)-(iv) of the primer-probe set is separately contacted with the sample. For example, the first or second assay probes may be added after the target-specific primer and/or probe. In certain aspects, the reporter may be a fluorophore and the change in the signal may be an unquenching of fluorescent signal. In some aspects, first and/or second assay probes comprise at least a first non-natural nucleotide such as isoG and/or isoC. In certain aspects, the second region of the first assay probe comprises 2 to 5 non-natural nucleotides and the second assay probe comprises 2 to 5 non-natural nucleotides that base-pair with the 2 to 5 non-natural nucleotides from the first assay probe. In still further aspects, at least a first non-natural nucleotide from the first assay probe is labeled with a reporter and at least a first non-natural nucleotide from the second assay probe is labeled with a quencher (or visa versa). In preferred aspects, each of the non-natural nucleotide from the first assay probe is labeled with a reporter and each of the non-natural nucleotide from the second assay probe is labeled with a quencher (or visa versa).

In certain aspects, the first and second assay probes have a known melt point and detecting a change in signal from the reporter comprises detecting the change in signal from the reporter as the temperature of the sample is changed. In certain aspects, the temperature of the sample may be increased above (or decreased below) the melt point of the first and second assay probes to observe a change in signal from the reporter.

In a further aspect, the first target-specific probe comprises a sequence complementary to the second region on the first strand of the target nucleic acid which is between 5, 10, 15, 20, 25, 30 and 40, 50, 75, 100, 125, 150, 175 or 200 nucleotides in length. In one aspect, the 5' tag sequence is between 6 and 50 nucleotides in length.

In still further aspects, the second region of first assay probe of a target-specific primer-probe set according to the embodiments comprises a polymerase extension-blocking modification. Accordingly, when the tag sequence from the target-specific probe is extended only a portion of the second assay probe is cleaved resulting in a change in the melt point between the first and second assay probes. Such a change in the observed melt point or melt peak can be used to detect the presence of a target nucleic acid molecule. Thus, in some aspects, detecting at least a first target nucleic acid sequence comprises detecting the change in signal from the reporter (on a first or second assay probe) as the temperature of the sample is changed.

In a specific aspect, a method of the embodiments comprises detecting the presence of one or both of a first and second target nucleic acid comprising (a) contacting the sample with at least a first and second target-specific primer-probe set, each primer-probe set comprising: (i) a primer complementary to a first region on a first strand of the target nucleic acid; (ii) a target-specific probe complementary to a second region on the first strand of the target nucleic acid downstream of the first region and comprising a 5' tag sequence that is not complementary to the target nucleic acid; (iii) a first assay probe comprising a first region which is complementary to the tag sequence from the target-specific probe and second region, downstream of the first region; and (iv) a second assay probe complimentary to the second region of the first assay probe, wherein one of the first and second assay probes is labeled with a reporter and the other is labeled with a quencher; and wherein the first and second assay probes have a known melt point and wherein the melt point of the first and second assay probes of the first primer-probe set is distinguishable from the melt point of the first and second assay probes of the second primer-probe set; (b) incubating the sample under conditions suitable for hybridization of the target nucleic acid with the target-specific primer and the target-specific probe of the primer-probe sets; (c) cleaving the hybridized target-specific probe with a nucleic acid polymerase having exonuclease activity to release the tag sequence from the target-specific probe; (d) hybridizing the released tag sequence with the first assay probe; (e) extending the hybridized tag sequence along the first assay probe and cleaving the second assay probe hybridized to the first assay probe; (f) detecting a target nucleic acid by detecting unquenching of the signal from the reporter on the first or second assay probe of the first and/or second primer-probe set; and (g) determining whether the second assay probe of the first target-specific primer-probe set, the second target-specific primer-probe set, or both, was cleaved by performing melt curve analysis on the first and second assay probes, wherein a reduction or elimination of a melt peak corresponding to a particular first and second assay probe set indicates that the second assay probe was cleaved and indicates the presence of the first or second target nucleic acid. Thus, in some aspects, detecting the presence of the first and second (or further) target nucleic acid is performed sequentially or essentially simultaneously. In a further aspect, the reporter of the first primer-probe set is the same as the reporter of the second primer-probe set. In certain aspect, the melt point of the first 5' tag and the first anti-tag reporter probe is distinguishable from the melt point of the second 5' tag and the second anti-tag reporter probe. Thus, in some aspects a method of the embodiments is a multiplex method comprising the use of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more primer-probe sets for detecting target nucleic acid molecules wherein each primer-probe set comprises either (1) a distinguishable reporter or (2) a first and second assay probe with a distinguishable melt point. In further aspects, the second region of the first assay probe comprises at least a first non-natural nucleotide (such as between 2 and 5 non-natural nucleotides) and the second assay probe comprises at least a first non-natural nucleotide that base-pairs with at least a first non-natural nucleotide from the first assay probe (e.g., 2 to 5 non-natural nucleotides that base pair with non-natural nucleotides of the first assay probe).

In certain aspects, a first assay probe of the embodiments comprises a polymerase extension blocking sequence, such as one or more non-natural nucleotide position(s). Thus, in certain aspects, a method if provided for detecting the presence of one or both of a first and second target nucleic acid comprising (a) contacting the sample with at least a first and second target-specific primer-probe set, each primer-probe set comprising: (i) a primer complementary to a first region on a first strand of the target nucleic acid; (ii) a target-specific probe complementary to a second region on the first strand of the target nucleic acid downstream of the first region and comprising a 5' tag sequence that is not complementary to the target nucleic acid; (iii) a first assay probe comprising a first region which is complementary to the tag sequence from the target-specific probe and second region, downstream of the first region comprising a polymerase extension-blocking modification; and (iv) a second assay probe complimentary to the second region of the first assay probe, said second region comprising the extension-blocking modification, wherein one of the first and second assay probes is labeled with a reporter and the other is labeled with a quencher; (b) incubating the sample under conditions suitable for hybridization of the target nucleic acid with the target-specific primer and the target-specific probe of the primer-probe sets; (c) cleaving the hybridized target-specific probe with a nucleic acid polymerase having exonuclease activity to release the tag sequence from the target-specific probe; (d) hybridizing the released tag sequence with the first assay probe; (e) extending the hybridized tag sequence along the first assay probe to the extension blocking sequence thereby cleaving a portion of the second assay probe hybridized to the first assay probe, wherein the first and second assay probes have a known melt point after said cleaving and wherein the melt point of the first and second assay probes of the first primer-probe set is distinguishable from the melt point of the first and second assay probes of the second primer-probe after said cleaving; (f) detecting a target nucleic acid by determining whether the second assay probe of the first target-specific primer-probe set, the second target-specific primer-probe set, or both, was cleaved by performing melt curve analysis on the first and second assay probes, wherein a temperature shift of a melt peak corresponding to a particular first and second assay probe set indicates that the second assay probe was cleaved and the indicates the presence of the first or second target nucleic acid. Thus, a distinguishable melt point for the assay probes is achieved after cleavage of a portion of the second assay probe (5' of sequence complementary to the extension blocking sequence). In some aspects, the melt point of the first and second assay probes of the first target-specific primer-probe set is between 2° C. and 10° C. different from the melt point of the first and second assay probes of the second target-specific primer-probe set, after the cleaving of (a portion of) the second assay probes. In still further aspects, the melt point of the first and second assay probes of the first target-specific primer-probe set is identical to the melt point of the first and second assay probes of the second target-specific primer-probe set before said cleaving of the second assay probes. For example, the second region of the first assay probes of the first and second target-specific primer-probe sets can be identical except for the position of the polymerase extension-blocking modification. In further aspects, the second region of the first assay probe comprises at least a first non-natural nucleotide (such as between 2 and 5 non-natural nucleotides) and the second assay probe comprises at least a first non-natural nucleotide that base-pairs with at least a first non-natural nucleotide from the first assay probe (e.g., 2 to 5 non-natural nucleotides that base pair with non-natural nucleotides of the first assay probe).

In a further aspect, the method further comprises contacting the sample with a target-specific primer complementary to a region on a second strand of the target nucleic acid. In some aspects, a method may further comprise performing multiple polymerase chain reaction cycles. In some aspects, detecting the change in signal from the reporter comprises detecting the signal before, during, or after performing the multiple polymerase chain reaction cycles (or during the cycles). In another aspect, detecting the change in signal from the reporter comprises detecting the signal only after performing the multiple polymerase chain reaction cycles. In this aspect, the method may further comprise comparing the detected signal from the reporter to a predetermined ratio of the signal of the reporter to a reference signal from a reporter on a non-hybridizing probe.

In some aspects, a method of the embodiments may further comprise quantifying the amount of the target nucleic acid in the sample. For example, quantifying the amount of the target nucleic acid in the sample comprises: using a standard curve; determining a relative amount of the nucleic acid target; using end-point quantitation; or determining an amount of the nucleic acid target by relating the PCR cycle number at which the signal is detectable over background to the amount of target present.

In a further embodiment, a composition is provided comprising a one or more primer-probe sets of the embodiments. For example, a composition can comprise (i) a primer complementary to a first region on a first strand of the target nucleic acid; (ii) a target-specific probe complementary to a second region on the first strand of the target nucleic acid downstream of the first region and comprising a 5' tag sequence, which is not complementary to the target nucleic acid; (iii) a first assay probe comprising a first region which is complementary to the tag sequence from the target specific probe and second region, downstream of the first region; and (iv) a second assay probe complimentary to the second region of the first assay probe, wherein the first assay probe or the second assay probe is labeled with a reporter and the other is labeled with a quencher. In still further aspects, the first assay probe comprises a first region which is complementary to the tag sequence from the target specific probe and second region, downstream of the first region, that comprises at least a first non-natural nucleotide; and the second assay probe (iv) comprises a sequence complimentary to the second region of the first assay probe and at least a first non-natural nucleotide which base-pairs with the non-natural nucleotide from the first assay probe, wherein the non-natural nucleotide from the first assay probe or the non-natural nucleotide from the second assay probe is labeled with a reporter and the other is labeled with a quencher. In certain aspects, the composition further comprises a (unlabeled) non-natural nucleotide that is capable of base-pairing with the non-natural nucleotide in the assay probe. In still further aspects, assay probes of the embodiments comprise between 2 and 5 non-natural nucleotides. In some aspects, a composition further comprises a target-specific primer complementary to a region on a second strand of the target nucleic acid, a polymerase having an exonuclease activity, a reference probe, a reference sample and/or a free nucleotide. In some aspects, the composition comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more distinguishable sets of primer-probe sets.

In a further embodiment, a kit is provided comprising one or more primer-probe sets of the embodiments. In a further aspect, the kit further comprises a polymerase with exonuclease activity, a reference probe, free nucleotides, free non-natural nucleotide, a reference sample or instructions for use of the kit.

In yet a further embodiment a method for detecting the presence of a target nucleic acid is provided comprising: (a) contacting the sample with a first set of probes, said set of probes comprising an upstream probe comprising a sequence complimentary to a first region on a first strand of the target nucleic acid and a downstream probe comprising, from 5' to 3', (i) a tag sequence comprising a non-natural nucleotide comprising a reporter; and (ii) a sequence complimentary to a second region on a first strand of the target nucleic acid downstream of the first region, such that when hybridized to the target nucleic acid the set of probes form a T-junction; (b) extending the upstream probe in the presence of a quencher-labeled non-natural nucleotide that is capable of base-pairing with the non-natural nucleotide in the downstream probe; and (c) detecting the target nucleic acid by detecting a change in signal from the label on the downstream probe. For example, in some aspects, the upstream probe comprises a 3' sequence of 2, 3, 4, 5, 6, 7, 8, 9, 10 or more bases complementary to the tag sequence of the downstream probe (e.g., a 3' sequence of 3 to 10 bases complementary to the tag sequence of the downstream probe). In some aspects, the 3' sequence of the upstream probe is defined as having complementary to the tag sequence of the downstream probe, over less than the full length of the tag sequence. In certain aspects, however, the upstream and the downstream probes have essentially no specific hybridization in the absence of a target sequence. In certain aspects, before being extended, the upstream and downstream probes have a melt point of less than 55, 50, 45, 40 or 35° C. in the absence of the target nucleic acid. In a further aspect of the method, extending the upstream probe comprises synthesis of a 3' extension complementary to the tag sequence of the down stream probe and including the quencher-labeled non-natural nucleotide.

As used herein a T-junction refers to a structure that is formed by an upstream and down stream probe when hybridized to a target sequence. Specifically, the upstream and down stream probes hybridize essentially to adjacent sequence of the target nucleic acid, such that the 5' tag of the downstream probe is free and not base-paired with the target. In some aspects, however, the 5' tag of the downstream probe base pairs with a 3' portion of the upstream probe (see, e.g., FIG. 4A, central panel).

In some aspects, the downstream probe (and/or upstream probe) may be attached to a solid support, such as a bead (e.g., an encoded bead) or a surface. In one aspect, the 5' non-natural nucleotide of the downstream probe is an isoG (or an isoC). In this aspect, the quencher-labeled non-natural nucleotide is a cognate isoC (isoG). Thus, in some aspects, extending the upstream probe comprises synthesis of a 3' extension complementary to the tag sequence of the down stream probe and including the quencher-labeled non-natural nucleotide. In further aspects, detecting a change in signal from the reporter on the downstream probe, further comprises hybridizing the extended upstream probe and the downstream probe.

As further detailed herein, in certain aspects, the reporter is a fluorophore and detecting a change in the signal of the reporter comprises detecting a decrease in a fluorescent signal. In certain aspects, detecting a change in signal from the reporter comprises detecting the change in signal from the reporter as the temperature of the sample is changed. For example, detecting a change in signal from the reporter comprises detecting the change in signal from the reporter as the temperature of the sample is increased above (or decreased below) the melt point of extended upstream probe and the downstream probe.

In still a further aspect a method comprises: (a) contacting the sample with a second set of probes comprising an upstream probe comprising a sequence complimentary to a first region on a first strand of a second target nucleic acid and a downstream probe comprising, from 5' to 3', (i) a tag sequence, comprising a reporter-labeled non-natural nucleotide; and (ii) a sequence complimentary to a second region on a first strand of the second target nucleic acid downstream of the first region, such that when hybridized to the target nucleic acid, the set of probes form a T-junction; (b) extending the upstream probe in the presence of a quencher-labeled non-natural nucleotide that is capable of base-pairing with the non-natural nucleotide in the downstream probe; and (c) detecting the second target nucleic acid by detecting a change in signal from the label on the downstream probe. For example, detecting the presence of the first and second target nucleic acid can be performed sequentially or essentially simultaneously. In certain aspects, the first and second set of probes comprise the same reporter or distinguishable reporters. In further aspects, the first and second set of probes comprise distinguishable melt points between the upstream and downstream probes.

In yet a further aspect a method of the embodiments is a multiplex method and comprises: (a) contacting the sample with a third, fourth, fifth or sixth set of probes, each set of probes comprising a sequence complimentary to a first region on a first strand of a third, fourth, fifth or sixth target nucleic acid and a downstream probe comprising, from 5' to 3', (i) a 5' non-natural nucleotide comprising a reporter; (ii) a tag sequence and (iii) a sequence complimentary to a second region on a first strand of the third, fourth, fifth or sixth target nucleic acid downstream of the first region, such that when hybridized to the target nucleic acid, the set of probes form a T-junction; (b) extending the upstream probe in the presence of a quencher-labeled non-natural nucleotide that is capable of base-pairing with the non-natural nucleotide in the downstream probe; and (c) detecting the third, fourth, fifth or sixth target nucleic acid by detecting a change in signal from the label on the downstream probe. Preferably, the first, second, third, fourth, fifth and/or sixth set of probes each comprise distinguishable reporters or distinguishable melt points between the upstream and downstream probes.

In still further aspects, a method of the embodiments can comprise performing multiple polymerase chain reaction cycles, such as multiple PCR cycles without a wash step to remove free-floating quencher between cycles. In certain aspects, detecting a change in signal from the reporter comprises detecting the signal before, after and/or during the multiple polymerase chain reaction cycles. In some aspects, detecting the change in signal from the reporter comprises detecting the signal only after performing the multiple polymerase chain reaction cycles. In certain aspects, a method further comprises comparing the detected signal from the reporter to a predetermined ratio of the signal of the reporter to a reference signal from a reporter on a non-hybridizing probe. Thus, in some aspects, a method of the embodiments comprises quantifying the amount of the target nucleic acid in the sample. For example, quantifying the amount of the target nucleic acid in the sample can comprise: using a standard curve; determining a relative amount of the nucleic acid target; using end-point quantitation; and/or determining an amount of the nucleic acid target by relating the PCR cycle number at which the signal is detectable over background to the amount of target present.

In yet a further embodiment a composition is provided comprising a first set of probes, said set of probes comprising an upstream probe comprising a sequence complimentary to a first region on a first strand of the target nucleic acid and a downstream probe comprising, from 5' to 3', (i) a tag sequence, comprising non-natural nucleotide comprising a reporter and (ii) a sequence complimentary to a second region on a first strand of the target nucleic acid downstream of the first region, such that when hybridized to the target nucleic acid the set of probes form a T-junction. In some aspects, the composition further comprises a second set of probes comprising an upstream probe comprising a sequence complimentary to a first region on a first strand of a second target nucleic acid and a downstream probe comprising, from 5' to 3', (i) a tag sequence, comprising a reporter-labeled non-natural nucleotide and (ii) a sequence complimentary to a second region on a first strand of the second target nucleic acid downstream of the first region, such that when hybridized to the target nucleic acid, the set of probes form a T-junction. In certain aspects, the composition comprises at least two, three, four, five or six sets of probes. Preferably, each set of probes comprises distinguishable reporters or distinguishable melt points between the upstream and downstream probes. In further aspects the composition additionally comprises a quencher-labeled non-natural nucleotide, a polymerase, a reference probe and/or free nucleotides.

In a related embodiment there is provided a kit comprising (a) a first set of probes comprising an upstream probe comprising a sequence complimentary to a first region on a first strand of the target nucleic acid and a downstream probe comprising, from 5' to 3', (i) a tag sequence, comprising a reporter-labeled non-natural nucleotide and (ii) a sequence complimentary to a second region on a first strand of the target nucleic acid downstream of the first region, such that when hybridized to the target nucleic acid the set of probes form a T-junction; and (b) a quencher-labeled non-natural nucleotide. In certain aspects, the kit comprises at least two, three, four, five or six sets of probes. Preferably, each set of probes comprises distinguishable reporters and/or distinguishable melt points between the upstream and downstream probes. In further aspects the kit additionally comprises a polymerase, a reference probe, free nucleotides, and/or instructions for use of the kit.

As used herein a solid support may be beads with magnetic properties and/or beads with a density that allows them to rest upon a two dimensional surface in solution. The particles may in one way or another rest upon a two dimensional surface by magnetic, gravitational, or ionic forces, or by chemical bonding, or by any other means known to those skilled in the art. Particles may consist of glass, polystyrene, latex, metal, quantum dot, polymers, silica, metal oxides, ceramics, or any other substance suitable for binding to nucleic acids, or chemicals or proteins which can then attach to nucleic acids. The particles may be rod shaped or spherical or disc shaped, or comprise any other shape. The particles may also be distinguishable by their shape or size or physical location. The particles may be spectrally distinct by virtue of having a composition containing dyes or ratios or concentrations of one or more dyes or fluorochromes, or may be distinguishable by barcode or holographic images or other imprinted forms of particle coding. Where the particles are magnetic particles, they may be attracted to the surface of the chamber by application of a magnetic field. Likewise, magnetic particles may be dispersed from the surface of the chamber by removal of the magnetic field. The magnetic particles are preferably paramagnetic or superparamagnetic. Paramagnetic and superparamagnetic particles have negligible magnetism in the absence of a magnetic field, but application of a magnetic field induces alignment of the magnetic domains in the particles, resulting in attraction of the particles to the field source. When the field is removed, the magnetic domains return to a random orientation so there is no interparticle magnetic attraction or repulsion. In the case of superparamagnetism, this return to random orientation of the domains is nearly instantaneous, while paramagnetic materials will retain domain alignment for some period of time after removal of the magnetic field. Where the particles have a sufficient density they may be attracted to the bottom surface of the chamber by gravity, and dispersed from the bottom surface of the chamber by agitation of the chamber, such as by vortexing, sonication, or fluidic movement. Agitation of the chamber may also be used to further assist in dispersing particles in methods and systems in which the particles were attracted to a surface of the chamber by other forces, such as magnetic or ionic forces, or suction forces, or vacuum filtration, or affinity, or hydrophilicity or hydrophobicity, or any combination thereof.

A labeling agent, which may also be referred to as a reporter, is a molecule that facilitates the detection of a molecule (e.g., a nucleic acid sequence) to which it is attached. Numerous reporter molecules that may be used to label nucleic acids are known. Direct reporter molecules include fluorophores, chromophores, and radiophores. Non-limiting examples of fluorophores include, a red fluorescent squarine dye such as 2,4-Bis[1,3,3-trimethyl-2-indolinylidenemethyl]cyclobutenediylium-1,3-dio-xolate, an infrared dye such as 2,4 Bis[3,3-dimethyl-2-(1H-benz[e]indolinylidenemethyl)]cyclobutenediylium-1,-3-dioxolate, or an orange fluorescent squarine dye such as 2,4-Bis[3,5-dimethyl-2-pyrrolyl]cyclobutenediylium-1,3-diololate. Additional non-limiting examples of fluorophores include quantum dots, Alexa Fluor™ dyes, AMCA, BODIPY™ 630/650, BODIPY™ 650/665, BODIPY™-FL, BODIPY™-R6G, BODIPY™-TMR, BODIPY™-TRX, Cascade Blue™, CyDye™, including but not limited to Cy2™, Cy3™, and Cy5™, a DNA intercalating dye, 6-FAM™, Fluorescein, HEX™, 6-JOE, Oregon Green™ 488, Oregon Green™ 500, Oregon Green™ 514, Pacific Blue™, REG, phycobilliproteins including, but not limited to, phycoerythrin and allophycocyanin, Rhodamine Green™, Rhodamine Red™, ROX™, TAMRA™, TET™, Tetramethylrhodamine, or Texas Red™. A signal amplification reagent, such as tyramide (PerkinElmer), may be used to enhance the fluorescence signal. Indirect reporter molecules include biotin, which must be bound to another molecule such as streptavidin-phycoerythrin for detection. Pairs of labels, such as fluorescence resonance energy transfer pairs or dye-quencher pairs, may also be employed.

Labeled amplification products may be labeled directly or indirectly. Direct labeling may be achieved by, for example, using labeled primers, using labeled dNTPs, using labeled nucleic acid intercalating agents, or combinations of the above. Indirect labeling may be achieved by, for example, hybridizing a labeled probe to the amplification product.

The methods disclosed herein may further comprise quantifying the initial amount of the nucleic acid target(s) in the sample. The quantification may comprise, for example, determining the relative concentrations of DNA present during the exponential phase of the real-time PCR by plotting fluorescence against cycle number on a logarithmic scale. The amounts of DNA may then be determined by comparing the results to a standard curve produced by real-time PCR of serial dilutions of a known amount of DNA. Additionally, real-time PCR may be combined with reverse transcription polymerase chain reaction to quantify RNAs in a sample, including low abundance RNAs.

The methods disclosed herein provide multiplexing capabilities such that a plurality of primer pairs (and/or probe sets) may amplify a plurality of target nucleic acids in a single amplification reaction. In certain embodiments there are at least 6, 7, 8, 9, 10, 11, or 1° different primer pairs (or probes) in an amplification reaction. In some embodiments there are between 8 to 100, 8 to 80, 8 to 60, 8 to 40, 8 to 20, 8 to 18, 8 to 16, 8 to 12, 10 to 100, 10 to 80, to 60, 10 to 40, 10 to 20, 10 to 18, 10 to 16, 10 to 12, 12 to 100, 12 to 80, 12 to 60, 12 to 40, 12 to 20, 12 to 18, or 12 to 16 different primer pairs (or probes) in an amplification reaction. In certain embodiments there are at least 6, 7, 8, 9, 10, 11, or 12 different target nucleic acids in a an amplification reaction. In some embodiments there are between 8 to 100, 8 to 80, 8 to 60, 8 to 40, 8 to 20, 8 to 18, 8 to 16, 8 to 12, 10 to 100, 10 to 80, 10 to 60, 10 to 40, 10 to 20, 10 to 18, 10 to 16, 10 to 12, 12 to 100, 12 to 80, 12 to 60, 12 to 40, 12 to 20, 12 to 18, or 12 to 16 different target nucleic acids in an amplification reaction. Probes present in the amplification reaction may, in some aspects, comprise a blocked 3' hydroxyl group to prevent extension of the probes by the polymerase. The 3' hydroxyl group may be blocked with, for example, a phosphate group or a 3' inverted dT. Nucleic acid amplification methods for use according to the embodiments include, but are not limited to PCR and isothermal amplification methods.

The target nucleic acid sequence may be any sequence of interest. The sample containing the target nucleic acid sequence may be any sample that contains nucleic acids. In certain aspects of the invention the sample is, for example, a subject who is being screened for the presence or absence of one or more genetic mutations or polymorphisms. In another aspect of the invention the sample may be from a subject who is being tested for the presence or absence of a pathogen. Where the sample is obtained from a subject, it may be obtained by methods known to those in the art such as aspiration, biopsy, swabbing, venipuncture, spinal tap, fecal sample, or urine sample. In some aspects of the invention, the sample is an environmental sample such as a water, soil, or air sample. In other aspects of the invention, the sample is from a plant, bacteria, virus, fungi, protozoan, or metazoan.

Each amplification cycle has three phases: a denaturing phase, a primer annealing phase, and a primer extension phase. The amplification cycle can be repeated until the desired amount of amplification product is produced. Typically, the amplification cycle is repeated between about 10 to 40 times. For real-time PCR, detection of the amplification products will typically be done after each amplification cycle. Although in certain aspects of the invention, detection of the amplification products may be done after every second, third, fourth, or fifth amplification cycle. Detection may also be done such that as few as 2 or more amplification cycles are analyzed or detected. The amplification cycle may be performed in the same chamber in which the detection of the amplification occurs, in which case this chamber would need to comprise a heating element so the temperature in the chamber can be adjusted for the denaturing phase, primer annealing phase, and a primer extension phase of the amplification cycle. The heating element would typically be under the control of a processor. The amplification cycle may, however, be performed in a different chamber from the chamber in which detection of the amplification occurs, in which case the "amplification" chamber would need to comprise a heating element but the "detection" or "imaging" chamber would not be required to have a heating element. Where amplification and detection occur in separate chambers, the fluid in which the amplification reaction occurs may be transferred between the chambers by, for example, a pump or piston. The pump or piston may be under the control of a processor. Alternatively, the fluid may be transferred between the chambers manually using, for example, a pipette.

Amplification may be performed in a reaction mixture that includes at least one non-natural nucleotide having a non-natural nucleotide. The at least one non-natural nucleotide of the reaction mixture may base pair with the at least one non-natural nucleotide present in the primer of the first and/or second primer set. Optionally, the non-natural nucleotide is coupled to a label which may include fluorophores and quenchers. The quencher may quench a fluorophore present in the primer of the first and/or second primer set.

Detecting may include amplifying one or more polynucleotides of the population. For example, detecting may include amplifying one or more polynucleotides of the population in the presence of at least one non-natural nucleotide. The non-natural nucleotide may have a non-natural nucleotide (e.g., isoC and isoG), which, optionally, is capable of base-pairing with the non-natural nucleotide of the mixture of oligonucleotides (e.g., a non-natural nucleotide present in the degenerate oligonucleotides). The non-natural nucleotide may be coupled to a label. Suitable labels include fluorophores and quenchers.

The method may be used to detect the target continuously during amplification or in real-time. The method may be used quantitatively.

In some embodiments, at least one of the first primer and the second primer includes at least one non-natural nucleotide (e.g., isoC and isoG), which may be present at the one or more positions. At least one of the first primer and the second primer may include a label. Where both the first primer and second primer include a label, the label may be the same or different, preferably different. Suitable labels include fluorophores and quenchers. Optionally, the label may be coupled to the non-natural nucleotide. Amplification may be performed using a reaction mixture that includes at least one non-natural nucleotide having a non-natural nucleotide, which optionally may base-pair with the non-natural nucleotide present in the first primer, the second primer, or both primers. The non-natural nucleotide of the reaction mixture may include a label. Suitable labels may include a fluorophore and a quencher, which optionally is capable of quenching a fluorophore, if present, in at least one of the first primer and second primer, preferably both.

Amplification may be performed in the presence of one or more non-natural nucleotides and/or in the presence of at least one quencher coupled to a non-natural nucleotide. In some embodiments, the non-natural nucleotide coupled to the at least one quencher may be isoCTP or isoGTP.

In some methods, the first and second labels may be different. In some methods the first and second quencher may be different and may be capable of quenching two different fluorophores. In other methods, the first and second quenchers may be the same and may be capable of quenching two different fluorophores.

The methods described herein may include determining a melting temperature for an amplicon (e.g., amplified nucleic acid of at least one of amplified nucleic acid of HIV and amplified control nucleic acid). The methods may include determining a melting temperature for a nucleic acid complex that includes a labeled probe hybridized to a target nucleic acid (which may include amplified target nucleic acid). The melting temperature may be determined by exposing the amplicon or nucleic acid complex to a gradient of temperatures and observing a signal from a label. Optionally, the melting temperature may be determined by (a) reacting an amplicon with an intercalating agent at a gradient of temperatures and (b) observing a detectable signal from the intercalating agent. The melting temperature of a nucleic acid complex may be determined by (1) hybridizing a probe to a target nucleic acid to form a nucleic acid complex, where at least one of the probe and the target nucleic acid includes a label; (2) exposing the nucleic acid complex to a gradient of temperatures; and (3) observing a signal from the label.

The methods may be performed in any suitable reaction chamber under any suitable conditions. For example, the methods may be performed in a reaction chamber without opening the reaction chamber. The reaction chamber may be part of an array of reaction chambers. In some embodiments, the steps of the methods may be performed separately in different reaction chambers.

In some embodiments, the methods may be capable of detecting no more than about 100 copies of the target nucleic acid in a sample (e.g., in a sample having a volume of about 25 microliters). In other embodiments, the methods may be capable of detecting no more than about 500 copies, 1000 copies, 5000 copies, or 10,000 copies in a sample (e.g., in a sample having a volume of about 25 microliters).

In other embodiments, the methods may be capable of detecting no more than about 100 copies of target nucleic acid in a sample (e.g., in a sample having a volume of about 25 microliters) using real-time detection in no more than about 150 cycles of the PCR, no more than about 100 cycles, no more than about 90 cycles, no more than about 80 cycles, no more than about 70 cycles, no more than about 60 cycles, no more than about 50 cycles, no more than about 40 cycles, or no more than about 30 cycles of the PCR.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

FIG. 1A—A hairpin extendable probe is designed comprising a reporter (asterisk) at its 5' end followed by a hairpin sequence, followed by a modification designed to block extension (e.g., C3 spacer; solid circle), followed by an isoC nucleotide, followed by a target specific sequence. FIG. 1B—During the PCR reaction, the probe is used as a primer for first-strand synthesis by the polymerase. FIG. 1C—Next, the polymerase extends the opposite strand using a downstream reverse primer for second strand synthesis. In some aspects, such a second primer may also comprise a labeled non-natural nucleotide. FIG. 1D—During the PCR reaction, an isoC-Quencher ("Q") will incorporate opposite the isoG nucleotide when the opposite strand extends back. FIG. 1E—Hairpin extendable probes are designed to have unique melting temperatures ($T_m$), such as, for example, 55, 60, 65, 70, 75, and 80° C., allowing for a 6-plex reaction for each color channel used for detection. This allows, for example, for a 36-plex reaction using six color detection channels. FIG. 1F—Melt profile showing an exemplary case where the target sequence detected by the $C_2$ probe was present in the sample and therefore produces an increased melt peak height or area under the curve at 60° C. upon separation of the reporter and the quencher. The melt peaks shown in FIG. 1F are determined by taking the first derivative of the melt curve.

FIG. 2A—Sequence A (tag sequence) is a melt-discrimination template-specific hybridization sequence. Sequence B is a target-specific hybridization sequence. Sequence A hybridizes to and can be extended when hybridized to a melt-discrimination template (see, Sequence C in FIG. 2C). Sequence B hybridizes to and can be optionally extended when hybridized to a target sequence. Together, Sequence A and Sequence B comprise a target-specific probe. FIG. 2B—Sequence B is degraded when an upstream primer is extended by an endonuclease-competent polymerase resulting in the cleavage and release of Sequence A from Sequence B. FIG. 2C—Sequence A of the cleaved probe hybridizes to the melt-discrimination template, also referred to as the "first assay probe" (Sequence C) upstream of a predesigned melt-discrimination probe, also referred to as the "second assay probe" (Sequence D). Sequence C has a position at its 5' end, which is labeled with a reporter (asterisk). In some cases sequence may included a non-natural nucleotide, such as isoG. Sequence D has a nucleotide, in this case isoC, at its 3' end, which base pairs with the nucleotide at the 3' end of Sequence C and is labeled with a quencher (Q). The labeled nucleotides are used to form a reporter-quencher pair. FIG. 2D—Sequence A is extended resulting in the degradation of Sequence D. This disrupts the reporter-quencher pair resulting in an increase in signal from the reporter during the course of a PCR reaction. FIG. 2E—Melt discrimination template-probe pairs are designed to have unique melting temperatures ($T_m$), such as, for example, 55, 60, 65, 70, 75, and 80° C., allowing for a 6-plex reaction for each color channel used for detection. This allows, for example, for a 36-plex reaction using six color detection channels. FIG. 2F—Presence of the target sequence, in this embodiment, leads to a decrease in the melt peak height or area under the curve for a specific predetermined melt discrimination template-probe pair. The melt peaks shown in FIG. 2F are determined by taking the first derivative of the melt curve.

FIG. 3A—After degradation of Sequence B (see, FIGS. 2A-B), Sequence A hybridizes to a melt-discrimination template (Sequence C) upstream of a predesigned melt-discrimination probe (Sequence D). The portion of Sequence C that hybridizes to Sequence D comprises a modification designed to block extension (e.g., C3 spacer or one or more non-natural nucleotides; indicated by the solid circle). Sequence C has a nucleotide (in this case isoG) at its 3' end, which is labeled with a reporter (asterisk). Sequence D has a nucleotide (in this case isoC) at its 3' end, which base pairs with nucleotide at the 5' end of Sequence C and is labeled with a quencher (Q). The labeled nucleotides are used to form a reporter-quencher pair. FIG. 3B—Sequence A is extended resulting in the degradation of a portion of Sequence D corresponding to the portion 5' of the extension blocker. FIG. 3C—Melt discrimination template-probe pairs are designed such that each intact melt discrimination template-probe pair has an identical $T_m$, such as, for example, 80° C. However, they are designed such that the portion that remains after degradation has a unique melting temperature ($T_m$), such as, for example, 50, 55, 60, 65, 70, and 75° C. This allows for a 6-plex reaction for each color channel used for detection. This allows, for example, for a 36-plex reaction using six color detection channels. FIG. 3D—Presence of a target sequence, in this embodiment, leads to a shift in the melt peak temperature for a specific predetermined melt discrimination template-probe pair corresponding to the target sequence present in the sample. The melt peaks shown in FIG. 3D are determined by taking the first derivative of the melt curve.

FIG. 4A—Two probes are designed to form a T-junction on a strand of an amplicon. The longer, downstream probe comprises a reporter-labeled isoG (asterisk) nucleotide at its 5' end and, optionally, a modification to block extension at its 3' end (solid circle). Extension of the upstream probe will incorporate a quencher-labeled isoC nucleotide (Q), which will quench the reporter and decrease the signal in the reaction. FIG. 4B—T-junction probes are designed to have unique melt temperatures ($T_m$), such as, for example, 55, 60, 65, 70, 75, and 80° C., allowing for a 6-plex reaction for each color channel used for detection. This allows, for example, for a 36-plex reaction using six color detection channels. A melt analysis can be performed and the target amplicon revealed.

FIG. 5A—Two probes are designed to form a T-junction on a strand of an amplicon. The upstream probe comprises a reporter-labeled isoC nucleotide ("isoC*") at its 5' end, a tag sequence, a sequence complementary to the amplicon (indicated as "A") and, optionally, one or more nucleotides that can base-pair with the "isoprimer complement" of the downstream probe. The downstream probe comprises a 5' isoC (which is unlabeled); a sequence that is the mirror of the tag sequence from the upstream probe ("mirrored tag"); optionally, a sequence that includes isoG and/or isoC positions (the "isoprimer complement") and a sequence that complementary to the amplicon (marked as "B"). Extension of the upstream probe will synthesize sequences complementary to the "isoprimer complement" and the "mirrored tag" on the downstream probe (i.e., the "isoprimer" and "tag complement" sequences) and will incorporate a quencher-labeled isoG nucleotide (isoG$^Q$). FIG. 5B—depicts an alternative embodiment of the T-junction probes described in FIG. 5A. In this case, the down stream probe does not include the 5' isoC position. Extension of the upstream probe will synthesize sequences complementary to the "isoprimer complement" and the "mirrored tag" on the downstream probe (i.e., the "isoprimer" and "tag complement" sequences). The upstream probe can then form a hairpin by base pairing of the "tag" and "tag complement" sequence, which allows the probe to incorporate a quencher-labeled isoG nucleotide (isoG$^Q$). FIG. 5C—A schematic of multiplex signal detection using the exemplary T-junction probes (e.g., those depicted in FIGS. 5A-5B). The probes can be designed to have unique melt temperatures ($T_m$), such as, for example, 55, 60, 65, 70, 75, and 80° C., allowing for a 6-plex reaction for each color channel used for detection. This allows, for example, for a 36-plex reaction using six color detection channels. A melt analysis can be performed to differentiation probes having different melt temperatures and the target amplicon revealed.

FIG. 9 shows the results with the original probes of Table 3 and FIG. 10 shows the results with shortened probes of Table 3.

FIG. 12—Asymmetric PCR results with full length T-SNAP probes. Graphs show amplification (upper panel) and melt (lower panel) curves for the probes of Table 5. Asymmetric PCR was performed with primer concentrations of Fwd/Rev=80/40 nM and 500 fM of the template. The amplitude of the melt curve was greater when the arm is part of the hairpin stem (indicated by the solid lines).

DESCRIPTION OF ILLUSTRATIVE EMBODIMENTS

Figure 1A:
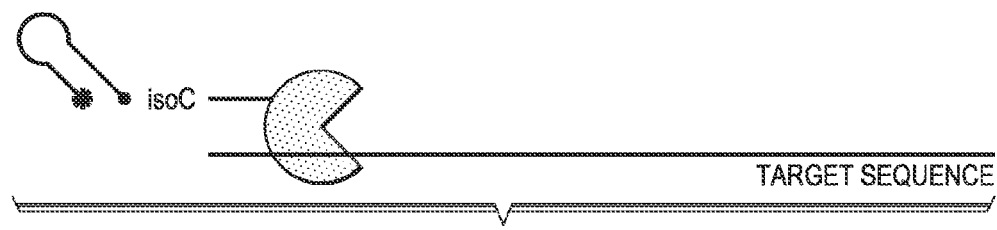
FIGS. 1A-F—A non-limiting exemplary schematic showing use of a hairpin extendable probe.

Melt analysis assays utilize melt or anneal peaks to discriminate amplicon identity, but these melt peaks are not easily distinguishable in amplicons that melt near the same temperature and are subject to the natural sequence composition of the target. By creating hairpin sequences with unique melt profiles, multiplexing can be achieved in a single color channel, thus allowing even more multiplexing with multiple color channels.

Disclosed are methods and kits for detecting nucleic acids in a sample. Typically, the methods include detecting signals, such as a signal emitted from a fluorophore. Also disclosed are oligonucleotides, especially primers and probes, which may be used for the detection of target nucleic acids.

I. Definitions

As used herein "nucleic acid" means either DNA or RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, and unusual base-pairing combinations, such as the isobases. Accordingly, the nucleic acids described herein include not only the standard bases adenine (A), cytosine (C), guanine (G), thymine (T), and uracil (U) but also non-standard or non-natural nucleotides. Non-standard or non-natural nucleotides, which form hydrogen-bonding base pairs, are described, for example, in U.S. Pat. Nos. 5,432, 272, 5,965,364, 6,001,983, 6,037,120, and 6,140,496, all of which are incorporated herein by reference. By "non-standard nucleotide" or "non-natural nucleotide" it is meant a base other than A, G, C, T, or U that is susceptible to incorporation into an oligonucleotide and that is capable of base-pairing by hydrogen bonding, or by hydrophobic, entropic, or van der Waals interactions, with a complementary non-standard or non-natural nucleotide to form a base pair. Some examples include the base pair combinations of iso-C/iso-G, K/X, K/P, H/J, and M/N, as illustrated in U.S. Pat. No. 6,037,120, incorporated herein by reference.

The hydrogen bonding of these non-standard or non-natural nucleotide pairs is similar to those of the natural bases where two or three hydrogen bonds are formed between hydrogen bond acceptors and hydrogen bond donors of the pairing non-standard or non-natural nucleotides. One of the differences between the natural bases and these non-standard or non-natural nucleotides is the number and position of hydrogen bond acceptors and hydrogen bond donors. For example, cytosine can be considered a donor/acceptor/acceptor base with guanine being the complementary acceptor/donor/donor base. Iso-C is an acceptor/acceptor/donor base and iso-G is the complementary donor/donor/acceptor base, as illustrated in U.S. Pat. No. 6,037,120, incorporated herein by reference.

Other non-natural nucleotides for use in oligonucleotides include, for example, naphthalene, phenanthrene, and pyrene derivatives as discussed, for example, in Ren, et al., J. Am. Chem. Soc. 1996, 118:1671 and McMinn et al., J. Am. Chem. Soc. 1999, 121:11585, both of which are incorporated herein by reference. These bases do not utilize hydrogen bonding for stabilization, but instead rely on hydrophobic or van der Waals interactions to form base pairs.

As used herein, the term "sample" is used in its broadest sense. A sample may include a bodily tissue or a bodily fluid including but not limited to blood (or a fraction of blood, such as plasma or serum), lymph, mucus, tears, urine, and saliva. A sample may include an extract from a cell, a chromosome, organelle, or a virus. A sample may comprise DNA (e.g., genomic DNA), RNA (e.g., mRNA), and/or cDNA, any of which may be amplified to provide an amplified nucleic acid. A sample may include nucleic acid in solution or bound to a substrate (e.g., as part of a microarray). A sample may comprise material obtained from an environmental locus (e.g., a body of water, soil, and the like) or material obtained from a fomite (i.e., an inanimate object that serves to transfer pathogens from one host to another).

The term "source of nucleic acid" refers to any sample that contains nucleic acids (RNA or DNA). Particularly preferred sources of target nucleic acids are biological samples including, but not limited to, blood, plasma, serum, saliva, cerebral spinal fluid, pleural fluid, milk, lymph, sputum, and semen.

As used herein, the term "limit of detection" refers to the lowest level or amount of an analyte, such as a nucleic acid, that can be detected and quantified. Limits of detection can be represented as molar values (e.g., 2.0 nM limit of detection), as gram measured values (e.g., 2.0 microgram limit of detection under, for example, specified reaction conditions), copy number (e.g., $1 \times 10^5$ copy number limit of detection), or other representations known in the art.

As used herein the term "isolated" in reference to a nucleic acid molecule refers to a nucleic acid molecule that is separated from the organisms and biological materials (e.g., blood, cells, serum, plasma, saliva, urine, stool, sputum, nasopharyngeal aspirates and so forth) that are present in the natural source of the nucleic acid molecule. An isolated nucleic acid molecule, such as a cDNA molecule, can be substantially free of other cellular material or culture medium when produced by recombinant techniques, or substantially free of chemical precursors or other chemicals when chemically synthesized. In some embodiments, nucleic acid molecules encoding polypeptides/proteins may also be isolated or purified. Methods of nucleic acid isolation are well known in the art and may include total nucleic acid isolation/purification methods, RNA-specific isolation/purification methods, or DNA-specific isolation/purification methods.

As used herein, the term "microarray" refers to an arrangement of a plurality of polynucleotides, polypeptides, or other chemical compounds on a substrate. The terms "element" and "array element" refer to a polynucleotide, polypeptide, or other chemical compound having a unique and defined position on a microarray.

As used herein, an oligonucleotide is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction may be made between oligodeoxyribonucleotides, made up of "dNTPs," which do not have a hydroxyl group at the 2' position, and oligoribonucleotides, made up of "NTPs," which have a hydroxyl group in the 2' position. Oligonucleotides also may include derivatives, in which the hydrogen of the hydroxyl group is replaced with an organic group, e.g., an allyl group.

An oligonucleotide is a nucleic acid that includes at least two nucleotides. Oligonucleotides used in the methods disclosed herein typically include at least about ten (10) nucleotides and more typically at least about fifteen (15) nucleotides. Preferred oligonucleotides for the methods disclosed herein include about 10-25 nucleotides. An oligonucleotide may be designed to function as a "primer." A "primer" is a short nucleic acid, usually a ssDNA oligonucleotide, which may be annealed to a target polynucleotide by complementary base-pairing. The primer may then be extended along the target DNA or RNA strand by a polymerase enzyme, such as a DNA polymerase enzyme. Primer pairs can be used for amplification (and identification) of a nucleic acid sequence (e.g., by the polymerase chain reaction (PCR)). An oligonucleotide may be designed to function as a "probe." A "probe" refers to an oligonucleotide, its complements, or fragments thereof, which are used to detect identical, allelic, or related nucleic acid sequences. Probes may include oligonucleotides that have been attached to a detectable label or reporter molecule. Typical labels include fluorescent dyes, quenchers, radioactive isotopes, ligands, scintillation agents, chemiluminescent agents, and enzymes.

An oligonucleotide may be designed to be specific for a target nucleic acid sequence in a sample. For example, an oligonucleotide may be designed to include "antisense" nucleic acid sequence of the target nucleic acid. As used herein, the term "antisense" refers to any composition capable of base-pairing with the "sense" (coding) strand of a specific target nucleic acid sequence. An antisense nucleic acid sequence may be "complementary" to a target nucleic acid sequence. As used herein, "complementarity" describes the relationship between two single-stranded nucleic acid sequences that anneal by base-pairing. For example, 5'-AGT-3' pairs with its complement, 3'-TCA-5'. In some embodiments, primers or probes may be designed to include mismatches at various positions. As used herein, a "mismatch" means a nucleotide pair that does not include the standard Watson-Crick base pairs, or nucleotide pairs that do not preferentially form hydrogen bonds. The mismatch may include a natural nucleotide or a non-natural or non-standard nucleotide substituted across from a particular base or bases in a target. For example, the probe or primer sequence 5'-AGT-3' has a single mismatch with the target sequence 3'-ACA-5'. The 5' "A" of the probe or primer is mismatched with the 3' "A" of the target. Similarly, the target sequence 5'-AGA-3' has a single mismatch with the probe or primer sequence 3'-(iC)CT-5'. Here an iso-C is substituted in place of the natural "T." However, the sequence 3'-(iC)CT-5' is not mismatched with the sequence 5'-(iG)GA-3'.

Oligonucleotides may also be designed as degenerate oligonucleotides. As used herein, "degenerate oligonucleotide" is meant to include a population, pool, or plurality of oligonucleotides comprising a mixture of different sequences where the sequence differences occur at a specified position in each oligonucleotide of the population. Various substitutions may include any natural or non-natural nucleotide, and may include any number of different possible nucleotides at any given position. For example, the above degenerate oligonucleotide may instead include R=iC or iG, or R=A or G or T or C or iC or iG.

Oligonucleotides, as described herein, typically are capable of forming hydrogen bonds with oligonucleotides having a complementary base sequence. These bases may include the natural bases, such as A, G, C, T, and U, as well as artificial, non-standard or non-natural nucleotides such as iso-cytosine and iso-guanine. As described herein, a first sequence of an oligonucleotide is described as being 100% complementary with a second sequence of an oligonucleotide when the consecutive bases of the first sequence (read 5'-to-3') follow the Watson-Crick rule of base pairing as compared to the consecutive bases of the second sequence (read 3'-to-5'). An oligonucleotide may include nucleotide substitutions. For example, an artificial base may be used in place of a natural base such that the artificial base exhibits a specific interaction that is similar to the natural base.

An oligonucleotide that is specific for a target nucleic acid also may be specific for a nucleic acid sequence that has "homology" to the target nucleic acid sequence. As used herein, "homology" refers to sequence similarity or, interchangeably, sequence identity, between two or more polynucleotide sequences or two or more polypeptide sequences. The terms "percent identity" and "% identity" as applied to polynucleotide sequences, refer to the percentage of residue matches between at least two polynucleotide sequences aligned using a standardized algorithm (e.g., BLAST).

An oligonucleotide that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Equations for calculating $T_m$, for example, nearest-neighbor parameters, and conditions for nucleic acid hybridization are known in the art.

As used herein, "target" or "target nucleic acid" refers to a nucleic acid molecule containing a sequence that has at least partial complementarity with an oligonucleotide, for example, a probe or a primer. A "target" sequence may include a part of a gene or genome.

As used herein, "nucleic acid," "nucleotide sequence," or "nucleic acid sequence" refer to a nucleotide, oligonucleotide, polynucleotide, or any fragment thereof and to naturally occurring or synthetic molecules. These terms also refer to DNA or RNA of genomic or synthetic origin, which may be single-stranded or double-stranded and may represent the sense or the antisense strand, or to any DNA-like or RNA-like material. An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose. RNA may be used in the methods described herein and/or may be converted to cDNA by reverse transcription for use in the methods described herein.

As used herein, "amplification" or "amplifying" refers to the production of additional copies of a nucleic acid sequence. Amplification is generally carried out using polymerase chain reaction (PCR) technologies known in the art. The term "amplification reaction system" refers to any in vitro means for multiplying the copies of a target sequence of nucleic acid. The term "amplification reaction mixture" refers to an aqueous solution comprising the various reagents used to amplify a target nucleic acid. These may include enzymes (e.g., a thermostable polymerase), aqueous buffers, salts, amplification primers, target nucleic acid, nucleoside triphosphates, and optionally, at least one labeled probe and/or optionally, at least one agent for determining the melting temperature of an amplified target nucleic acid (e.g., a fluorescent intercalating agent that exhibits a change in fluorescence in the presence of double-stranded nucleic acid).

The amplification methods described herein may include "real-time monitoring" or "continuous monitoring." These terms refer to monitoring multiple times during a cycle of PCR, preferably during temperature transitions, and more preferably obtaining at least one data point in each temperature transition. The term "homogeneous detection assay" is used to describe an assay that includes coupled amplification and detection, which may include "real-time monitoring" or "continuous monitoring."

Amplification of nucleic acids may include amplification of nucleic acids or subregions of these nucleic acids. For example, amplification may include amplifying portions of nucleic acids between 30 and 50, between 50 and 100, or between 100 and 300 bases long by selecting the proper primer sequences and using PCR. In further aspects, amplification can be achieved using an isothermal amplification technique (i.e., without the need for thermal cycling). For example, methods for isothermal nucleic acid amplification, such as loop mediated isothermal amplification (LAMP), are provided in U.S. Pat. No. 6,410,278, and US. Patent Publn. 20080182312 each of which is incorporated herein by reference in its entirety.

The disclosed methods may include amplifying at least one or more nucleic acids in the sample. In the disclosed methods, amplification may be monitored using real-time methods.

Amplification mixtures may include natural nucleotides (including A, C, G, T, and U) and non-natural or non-standard nucleotides (e.g., including iC and iG). DNA and RNA oligonucleotides include deoxyriboses or riboses, respectively, coupled by phosphodiester bonds. Each deoxyribose or ribose includes a base coupled to a sugar. The bases incorporated in naturally-occurring DNA and RNA are adenosine (A), guanosine (G), thymidine (T), cytosine (C), and uridine (U). These five bases are "natural bases." According to the rules of base pairing elaborated by Watson and Crick, the natural bases hybridize to form purine-pyrimidine base pairs, where G pairs with C and A pairs with T or U. These pairing rules facilitate specific hybridization of an oligonucleotide with a complementary oligonucleotide.

The formation of base pairs by natural bases is facilitated by the generation of two or three hydrogen bonds between the two bases of each base pair. Each of the bases includes two or three hydrogen bond donor(s) and hydrogen bond acceptor(s). The hydrogen bonds of the base pair are each formed by the interaction of at least one hydrogen bond donor on one base with a hydrogen bond acceptor on the other base. Hydrogen bond donors include, for example, heteroatoms (e.g., oxygen or nitrogen) that have at least one attached hydrogen. Hydrogen bond acceptors include, for example, heteroatoms (e.g., oxygen or nitrogen) that have a lone pair of electrons.

The natural or non-natural nucleotides used herein can be derivatized by substitution at non-hydrogen bonding sites to form modified natural or non-natural nucleotides. For example, a natural nucleotide can be derivatized for attachment to a support by coupling a reactive functional group (for example, thiol, hydrazine, alcohol, amine, and the like) to a non-hydrogen bonding atom of the nucleotide. Other possible substituents include, for example, biotin, digoxigenin, fluorescent groups, alkyl groups (e.g., methyl or ethyl), and the like.

The use of non-natural nucleotides according to the methods disclosed herein is extendable beyond the detection and quantification of nucleic acid sequences present in a sample. For example, non-natural nucleotides can be recognized by many enzymes that catalyze reactions associated with nucleic acids. While a polymerase requires a complementary nucleotide to continue polymerizing and extending an oligonucleotide chain, other enzymes do not require a complementary nucleotide. If a non-natural nucleotide is present in the template and its complementary non-natural nucleotide is not present in the reaction mix, a polymerase will typically stall (or, in some instances, misincorporate a base when given a sufficient amount of time) when attempting to extend an elongating primer past the non-natural nucleotide. However, other enzymes that catalyze reactions associated with nucleic acids, such as ligases, kinases, nucleases, polymerases, topoisomerases, helicases, and the like can catalyze reactions involving non-natural nucleotides. Such features of non-natural nucleotides can be taken advantage of, and are within the scope of the presently disclosed methods and kits.

The nucleotides disclosed herein, which may include non-natural nucleotides, may be coupled to a label (e.g., a quencher or a fluorophore). Coupling may be performed using methods known in the art.

The oligonucleotides of the present methods may function as primers. In some embodiments, the oligonucleotides are labeled. For example, the oligonucleotides may be labeled with a reporter that emits a detectable signal (e.g., a fluorophore). The oligonucleotides may include at least one non-natural nucleotide. For example, the oligonucleotides may include at least one nucleotide having a base that is not A, C, G, T, or U (e.g., iC or iG). Where the oligonucleotide is used as a primer, e.g., for PCR, the amplification mixture may include at least one nucleotide that is labeled with a quencher (e.g., Dabcyl). The labeled nucleotide may include at least one non-natural or non-standard nucleotide. For example, the labeled nucleotide may include at least one nucleotide having a base that is not A, C, G, T, or U (e.g., iC or iG).

In some embodiments, the oligonucleotide may be designed not to form an intramolecular structure, such as a hairpin. In other embodiments, the oligonucleotide may be designed to form an intramolecular structure, such as a hairpin. For example, the oligonucleotide may be designed to form a hairpin structure that is altered after the oligonucleotide hybridizes to a target nucleic acid, and optionally, after the target nucleic acid is amplified using the oligonucleotide as a primer.

The oligonucleotide may be labeled with a fluorophore that exhibits quenching when incorporated in an amplified product as a primer. In other embodiments, the oligonucleotide may emit a detectable signal after the oligonucleotide is incorporated in an amplified product as a primer (e.g., inherently, or by fluorescence induction or fluorescence dequenching). Such primers are known in the art (e.g., LightCycler primers, Amplifluor™ primers, Scorpion™ primers, and Lux™ primers). The fluorophore used to label the oligonucleotide may emit a signal when intercalated in double-stranded nucleic acid. As such, the fluorophore may emit a signal after the oligonucleotide is used as a primer for amplifying the nucleic acid.

The oligonucleotides that are used in the disclosed methods may be suitable as primers for amplifying at least one nucleic acid in the sample and as probes for detecting at least one nucleic acid in the sample. In some embodiments, the oligonucleotides are labeled with at least one fluorescent dye, which may produce a detectable signal. The fluorescent dye may function as a fluorescence donor for fluorescence resonance energy transfer (FRET). The detectable signal may be quenched when the oligonucleotide is used to amplify a target nucleic acid. For example, the amplification mixture may include nucleotides that are labeled with a quencher for the detectable signal emitted by the fluorophore. Optionally, the oligonucleotides may be labeled with a second fluorescent dye or a quencher dye that may function as a fluorescence acceptor (e.g., for FRET). Where the oligonucleotide is labeled with a first fluorescent dye and a second fluorescent dye, a signal may be detected from the first fluorescent dye, the second fluorescent dye, or both. Signals may be detected at a gradient of temperatures (e.g., in order to determine a melting temperature for an amplicon, a complex that includes a probe hybridized to a target nucleic acid, a hairpin, or a T probe complex).

The disclosed methods may be performed with any suitable number of oligonucleotides. Where a plurality of oligonucleotides are used (e.g., two or more oligonucleotides), different oligonucleotide may be labeled with different fluorescent dyes capable of producing a detectable signal. In some embodiments, oligonucleotides are labeled with at least one of two different fluorescent dyes. In further embodiments, oligonucleotides are labeled with at least one of three different fluorescent dyes.

In some embodiments, each different fluorescent dye emits a signal that can be distinguished from a signal emitted by any other of the different fluorescent dyes that are used to label the oligonucleotides. For example, the different fluorescent dyes may have wavelength emission maximums all of which differ from each other by at least about 5 nm (preferably by least about 10 nm). In some embodiments, each different fluorescent dye is excited by different wavelength energies. For example, the different fluorescent dyes may have wavelength absorption maximums all of which differ from each other by at least about 5 nm (preferably by at least about 10 nm).

Where a fluorescent dye is used to determine the melting temperature of a nucleic acid in the method, the fluorescent dye may emit a signal that can be distinguished from a signal emitted by any other of the different fluorescent dyes that are used to label the oligonucleotides. For example, the fluorescent dye for determining the melting temperature of a nucleic acid may have a wavelength emission maximum that differs from the wavelength emission maximum of any other fluorescent dye that is used for labeling an oligonucleotide by at least about 5 nm (preferably by least about 10 nm). In some embodiments, the fluorescent dye for determining the melting temperature of a nucleic acid may be excited by different wavelength energy than any other of the different fluorescent dyes that are used to label the oligonucleotides. For example, the fluorescent dye for determining the melting temperature of a nucleic acid may have a wavelength absorption maximum that differs from the wavelength absorption maximum of any fluorescent dye that is used for labeling an oligonucleotide by at least about 5 nm (preferably by at least about 10 nm).

The methods may include determining the melting temperature of at least one nucleic acid in a sample (e.g., an amplicon or a nucleic acid complex that includes a probe hybridized to a target nucleic acid), which may be used to identify the nucleic acid. Determining the melting temperature may include exposing an amplicon or a nucleic acid complex to a temperature gradient and observing a detectable signal from a fluorophore. Optionally, where the oligonucleotides of the method are labeled with a first fluorescent dye, determining the melting temperature of the detected nucleic acid may include observing a signal from a second fluorescent dye that is different from the first fluorescent dye. In some embodiments, the second fluorescent dye for determining the melting temperature of the detected nucleic acid is an intercalating agent. Suitable intercalating agents may include, but are not limited to SYBR™ Green 1 dye, SYBR dyes, Pico Green, SYTO dyes, SYTOX dyes, ethidium bromide, ethidium homodimer-1, ethidium homodimer-2, ethidium derivatives, acridine, acridine orange, acridine derivatives, ethidium-acridine heterodimer, ethidium monoazide, propidium iodide, cyanine monomers, 7-aminoactinomycin D, YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, and mixtures thereof. In suitable embodiments, the selected intercalating agent is SYBR™ Green 1 dye.

In the disclosed methods, each of the amplified target nucleic acids or reporter probe-template pairs may have different melting temperatures. For example, each of the amplified target nucleic acids or reporter probe-template pairs may have melting temperatures that differ by 1-10° C., for example, at least about 1° C., more preferably by at least about 2° C., or even more preferably by at least about 4° C. from the melting temperature of any of the other amplified target nucleic acids or reporter probe-template pairs.

As used herein, "labels" or "reporter molecules" are chemical or biochemical moieties useful for labeling a nucleic acid. "Labels" and "reporter molecules" include fluorescent agents, chemiluminescent agents, chromogenic agents, quenching agents, radionuclides, enzymes, substrates, cofactors, scintillation agents, inhibitors, magnetic particles, and other moieties known in the art. "Labels" or "reporter molecules" are capable of generating a measurable signal and may be covalently or noncovalently joined to an oligonucleotide.

As used herein, a "fluorescent dye" or a "fluorophore" is a chemical group that can be excited by light to emit fluorescence. Some suitable fluorophores may be excited by light to emit phosphorescence. Dyes may include acceptor dyes that are capable of quenching a fluorescent signal from a fluorescent donor dye. Dyes that may be used in the disclosed methods include, but are not limited to, fluorophores such as, a red fluorescent squarine dye such as 2,4-Bis[1,3,3-trimethyl-2-indolinylidenemethyl]cyclobutenediylium-1,3-dio-xolate, an infrared dye such as 2,4 Bis[3,3-dimethyl-2-(1H-benz[e]indolinylidenemethyl)]cyclobutenediylium-1,-3-dioxolate, or an orange fluorescent squarine dye such as 2,4-Bis[3,5-dimethyl-2-pyrrolyl]cyclobutenediylium-1,3-diololate. Additional non-limiting examples of fluorophores include quantum dots, Alexa Fluor™ dyes, AMCA, BODIPY™ 630/650, BODIPY™ 650/665, BODIPY™-FL, BODIPY™-R6G, BODIPY™-TMR, BODIPY™-TRX, Cascade Blue™, CyDye™, including but not limited to Cy2™, Cy3™, and Cy5™, a DNA intercalating dye, 6-FAM™, Fluorescein, HEX™, 6-JOE, Oregon Green™ 488, Oregon Green™ 500, Oregon Green™ 514, Pacific Blue™, REG, phycobilliproteins including, but not limited to, phycoerythrin and allophycocyanin, Rhodamine Green™, Rhodamine Red™, ROX™, TAMRA™, TET™, Tetramethylrhodamine, or Texas Red™.

Fluorescent dyes or fluorophores may include derivatives that have been modified to facilitate conjugation to another reactive molecule. As such, fluorescent dyes or fluorophores may include amine-reactive derivatives, such as isothiocyanate derivatives and/or succinimidyl ester derivatives of the fluorophore.

The oligonucleotides and nucleotides of the disclosed methods may be labeled with a quencher. Quenching may include dynamic quenching (e.g., by FRET), static quenching, or both. Suitable quenchers may include Dabcyl. Suitable quenchers may also include dark quenchers, which may include black hole quenchers sold under the trade name "BHQ" (e.g., BHQ-0, BHQ-1, BHQ-2, and BHQ-3, Biosearch Technologies, Novato, Calif.). Dark quenchers also may include quenchers sold under the trade name "QXL™" (Anaspec, San Jose, Calif.). Dark quenchers also may include DNP-type non-fluorophores that include a 2,4-dinitrophenyl group.

II. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Hairpin Probe Extension with Unique Melt Signatures

Figure 1B:

An extendable probe with a hairpin has been designed to provide unique melt peaks during a melt analysis to allow for greater discrimination of target identity in a melt assay, which can allow for greater multiplexing. This extendable probe can function as a probe when targeted to a sequence within an amplicon for a second level of discrimination, or it can be used as a primer in a primer set (FIGS. 1A-B).

Figure 1C:
Figure 1D:

The extendable probe comprises, in sequence from the 5' end to the 3' end, a reporter (star), for example, a fluorophore, a sequence capable of forming a hairpin, a modification designed to block extension (e.g., C3 spacer) during second strand synthesis, an isoG nucleotide, and a target specific sequence. During second strand synthesis using the extended probe as a template, a quencher-labeled isoC nucleotide will be incorporated opposite the isoG nucleotide (FIGS. 1C-D).

Figure 1E:
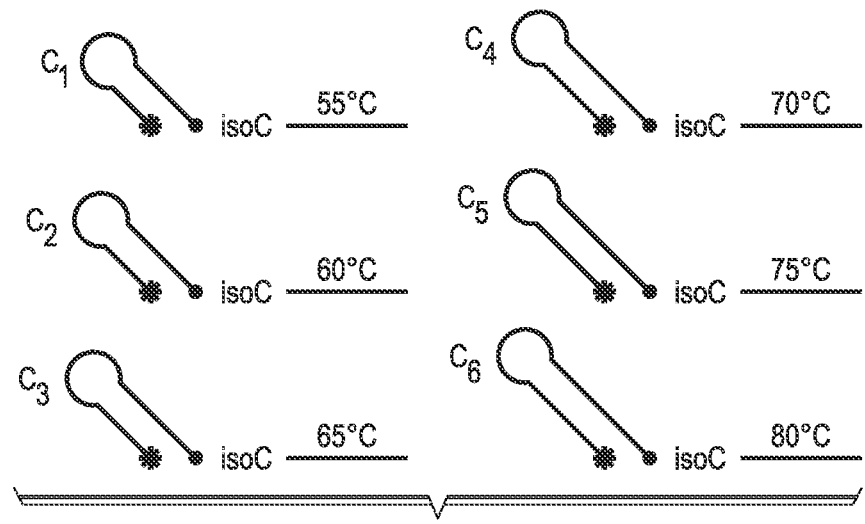

If hairpin probes are designed such that each hairpin has a unique $T_m$, then the probes can be distinguished by melt analysis. It is envisioned that hairpin melt temperatures ($T_m$) of 55, 60, 65, 70, 75, and 80° C. can be utilized in a single color channel (FIG. 1E). Therefore, the use of six color channels could create a 36-plex assay. In order to obtain distinguishable peaks when performing melt analysis of multiple hairpins, the hairpin the melt temperatures ($T_m$) must be designed so as to ensure that they are lower than the melt temperatures ($T_m$) of all amplicons present in the reaction.

Figure 1F:
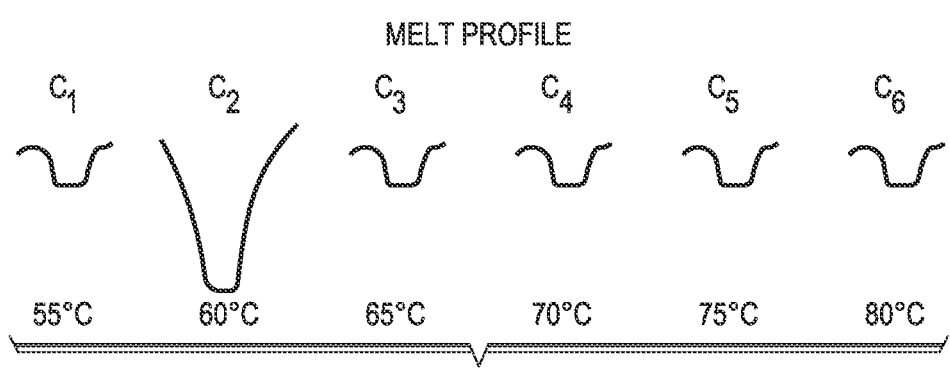

Presence of a target sequence, in this embodiment, will start a chain reaction leading to a decrease in signal in the detection channel due to quenching of the reporter on the hairpin extendable probe. Then, upon melt analysis, the probe for which the target sequence was present in the reaction will produce an increased melt peak height or area under the curve at its predesigned $T_m$ (e.g., 60° C.) due to the separation of the reporter from the quencher (e.g., FIG. 1F). Alternatively, upon anneal analysis, the probe for which the target sequence was present in the reaction will produce a decreased anneal peak height or area under the curve at its predesigned $T_m$ (e.g., 65° C.) due to quenching of the reporter upon annealing (see, e.g., FIG. 2F).

Additionally, a reporter-quencher pair can be used at the opposite end of the amplicon of the hairpin melt discriminator probe if the melt peak of the amplicon itself is desired. Hairpin sequences may also be used at both ends of the amplicon for greater proof that the target amplicon was created. The fluorophores used at opposite ends of an amplicon may have different emission spectra.

EXAMPLE 2

Figure 2A:
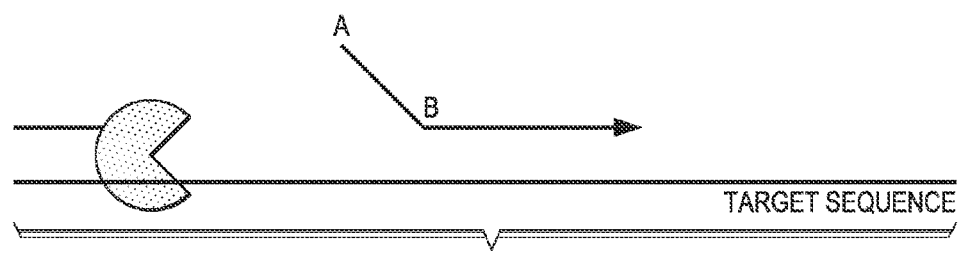
FIGS. 2A-F—A non-limiting exemplary schematic showing a hydrolysis functionalized assay probes.
Figure 2B:
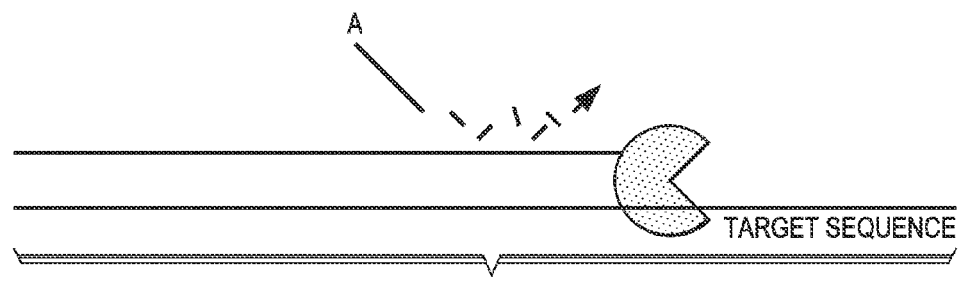
Figure 2C:
Figure 2D:

Endonuclease Reaction Followed by Extension and Exonuclease Cleavage of Melt-discrimination Probe-template Pairs An extendable probe is designed with a target-specific hybridization sequence at its 3' end (Sequence B, FIG. 2A) and a melt-discrimination template-specific hybridization sequence at its 5' end (Sequence A, FIG. 2A). In the presence of the target sequence, polymerase extension from an upstream primer during a PCR reaction cleaves the melt-discrimination template-specific hybridization sequence (FIG. 2B) and degradation of the target-specific hybridization sequence. The cleaved melt-discrimination template-specific hybridization sequence hybridizes to and extends on a melt-discrimination template (Sequence C, FIG. 2C) that has a predesigned melt-discrimination probe (Sequence D, FIG. 2C) hybridized downstream of the binding site for the melt-discrimination template-specific hybridization sequence (FIG. 2C). The 3' end of the melt-discrimination template comprises a reporter-labeled isoG nucleotide and the 5' end of the melt-discrimination probe comprises a quencher-labeled isoC nucleotide. Under conditions allowing for hybridization of the melt-discrimination probe to the melt-discrimination template, the reporter and quencher are in close enough proximity to allow quenching of the reporter. Extension of the melt-discrimination template-specific hybridization sequence by the polymerase during the course of the PCR reaction causes degradation of the melt-discrimination probe (FIG. 2D). Degradation of the melt-discrimination probe results in an increase in signal from the reporter during the course of the PCR reaction.

Figure 2E:
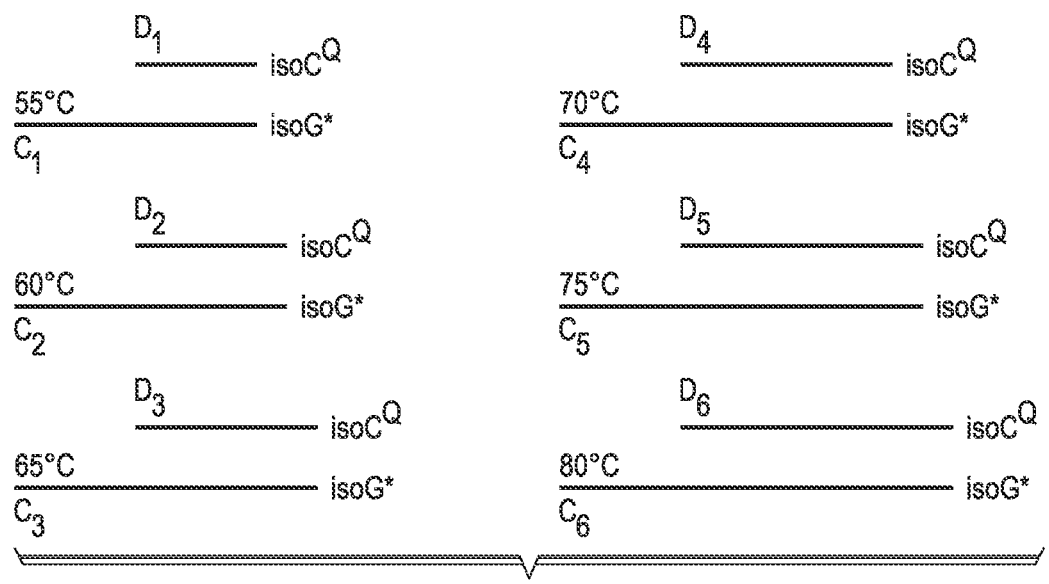
Figure 2F:
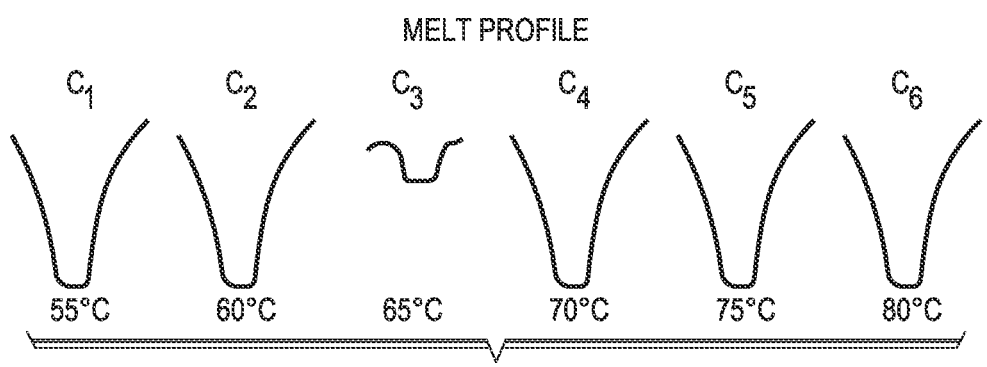

To multiplex the reaction, melt-discrimination probe-melt-discrimination template pairs are designed such that each pair has a unique $T_m$. Six pairs of probes can be designed, with each of the six having a $T_m$ of 55, 60, 65, 70, 75, or 80° C., thereby allowing a 6-plex reaction using only one color detection channel (FIG. 2E). Using multiple reporter-quencher pairs that are each detected on a unique color channel allows the performance of a 36-plex reaction with the use of six reporter-quencher pairs on six color channels. In this case, degradation of the melt-discrimination probe results in a decrease in the area under the curve at the specific temperature of the melt-discrimination probe-melt-discrimination template complex during melt analysis following the PCR reaction (e.g., FIG. 2F).

EXAMPLE 3

Figure 3A:
FIGS. 3A-D—A non-limiting exemplary schematic showing a hydrolysis functionalized probe and a melt-discrimination template with an extension blocker.
Figure 3B:

Endonuclease Reaction Followed by Extension and Exonuclease Cleavage of Melt-discrimination Probe-template Pairs that Comprise an Extension Blocker An alternative embodiment of the melt-discrimination probe-melt-discrimination template pairs described in Example 2 is presented here. In this embodiment, the melt-discrimination template (Sequence C) comprises a modification designed to block extension (e.g., C3 spacer) with the portion of the template that hybridizes to the melt-discrimination probe (Sequence D) (FIG. 3A). When Sequence A from the hydrolyzed target-specific probe hybridizes to and extends on a melt-discrimination template (Sequence C, FIG. 3A) that has a predesigned melt-discrimination probe (Sequence D, FIG. 3A) hybridized downstream of the binding site for the melt-discrimination template-specific hybridization sequence. The 3' end of the melt-discrimination template comprises a reporter-labeled isoG nucleotide and the 5' end of the melt-discrimination probe comprises a quencher-labeled isoC nucleotide. Under conditions allowing for hybridization of the melt-discrimination probe to the melt-discrimination template, the reporter and quencher are in close enough proximity to allow quenching of the reporter. Extension of the melt-discrimination template-specific hybridization sequence by the polymerase will cease at the extension blocking modification during the course of the PCR reaction resulting in partial degradation of the melt-discrimination probe (FIG. 3B). Partial degradation of the melt-discrimination probe will not affect the signal from the reporter during the course of the PCR reaction. The signal will only be realized upon melt analysis.

Figure 3C:
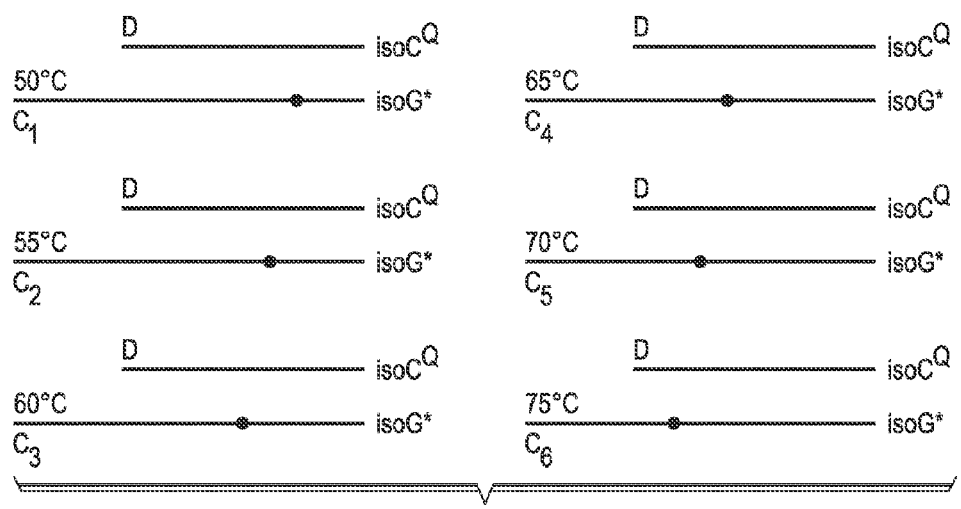
Figure 3D:
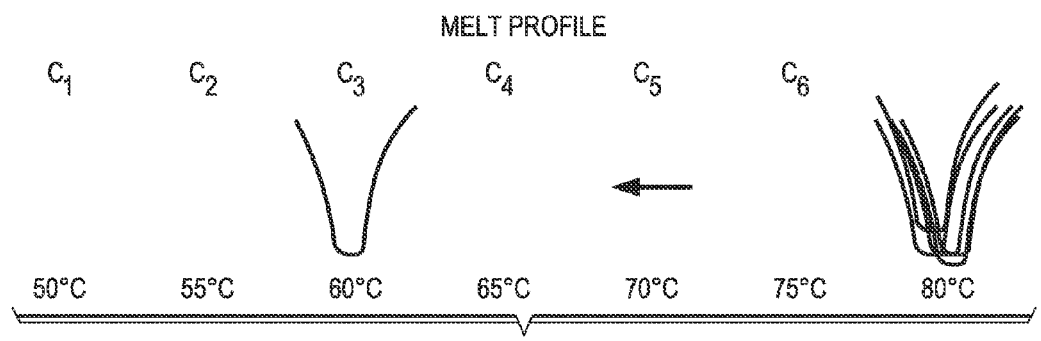

Melt-discrimination probe-melt-discrimination template pairs are designed such that each intact pair has an identical $T_m$, such as, for example, 80° C. However, each pair is designed such that the portion of the probe that remains bound to the template after degradation has a unique $T_m$, such as, for example, 50, 55, 60, 65, 70, or 75° C., thereby allowing a 6-plex reaction using only one color detection channel (FIG. 3C). Using multiple reporter-quencher pairs that are each detected on a unique color channel allows the performance of a 36-plex reaction with the use of six reporter-quencher pairs on six color channels. In this embodiment, partial degradation of the melt-discrimination probe results in a shift in the melt profile of the melt-discrimination probe-melt-discrimination template pair that corresponds to the target sequence present in the reaction (e.g., FIG. 3D).

EXAMPLE 4

T-junction Probe Extension with Unique Melt Signatures

Figure 4A:
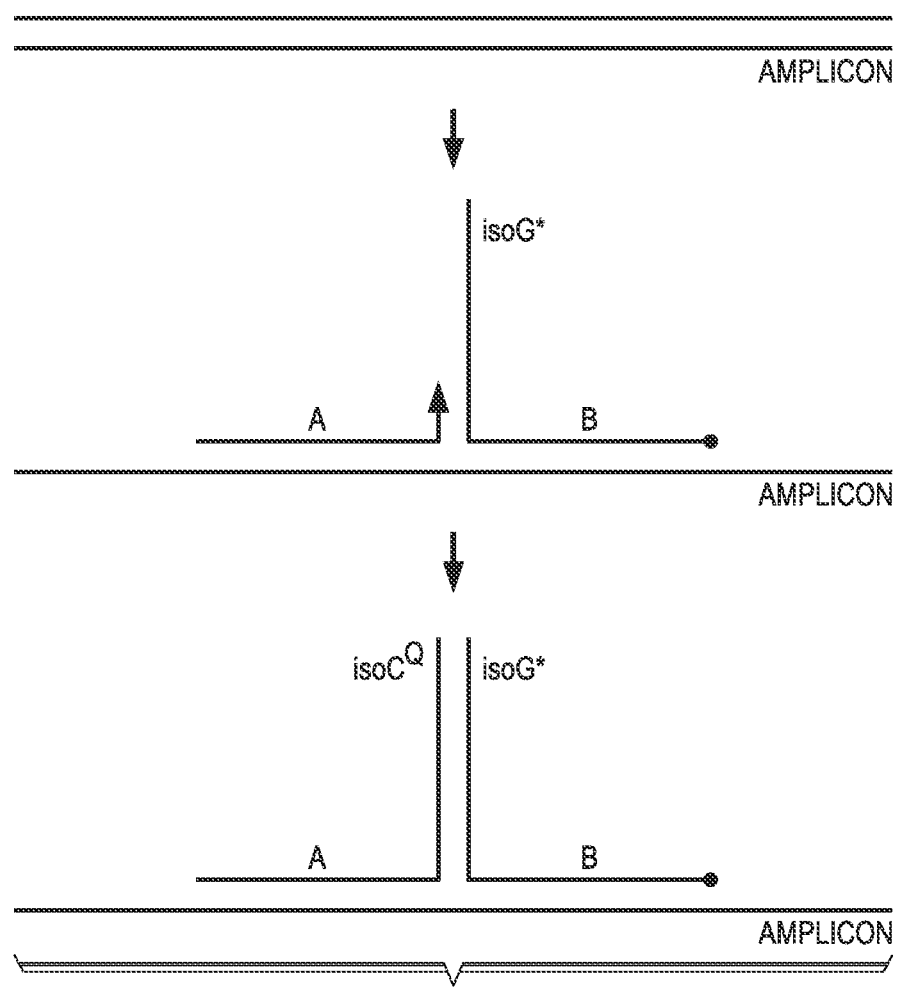
FIGS. 4A-B—A non-limiting exemplary schematic showing T-junction probes.

Two probes that form a T-junction on a strand of an amplicon are designed to extend only when hybridized to the target strand (see FIGS. 4-5). In the design shown in FIG. 4A, the longer, downstream probe comprises a reporter-labeled isoG nucleotide at its 5' end and, optionally, a modification to block extension at its 3' end. When both probes hybridize to the target strand, the shorter, upstream probe can extend and incorporate a quencher-labeled isoC nucleotide at its 3' end, which will quench the reporter and decrease the signal in the reaction.

Figure 4B:
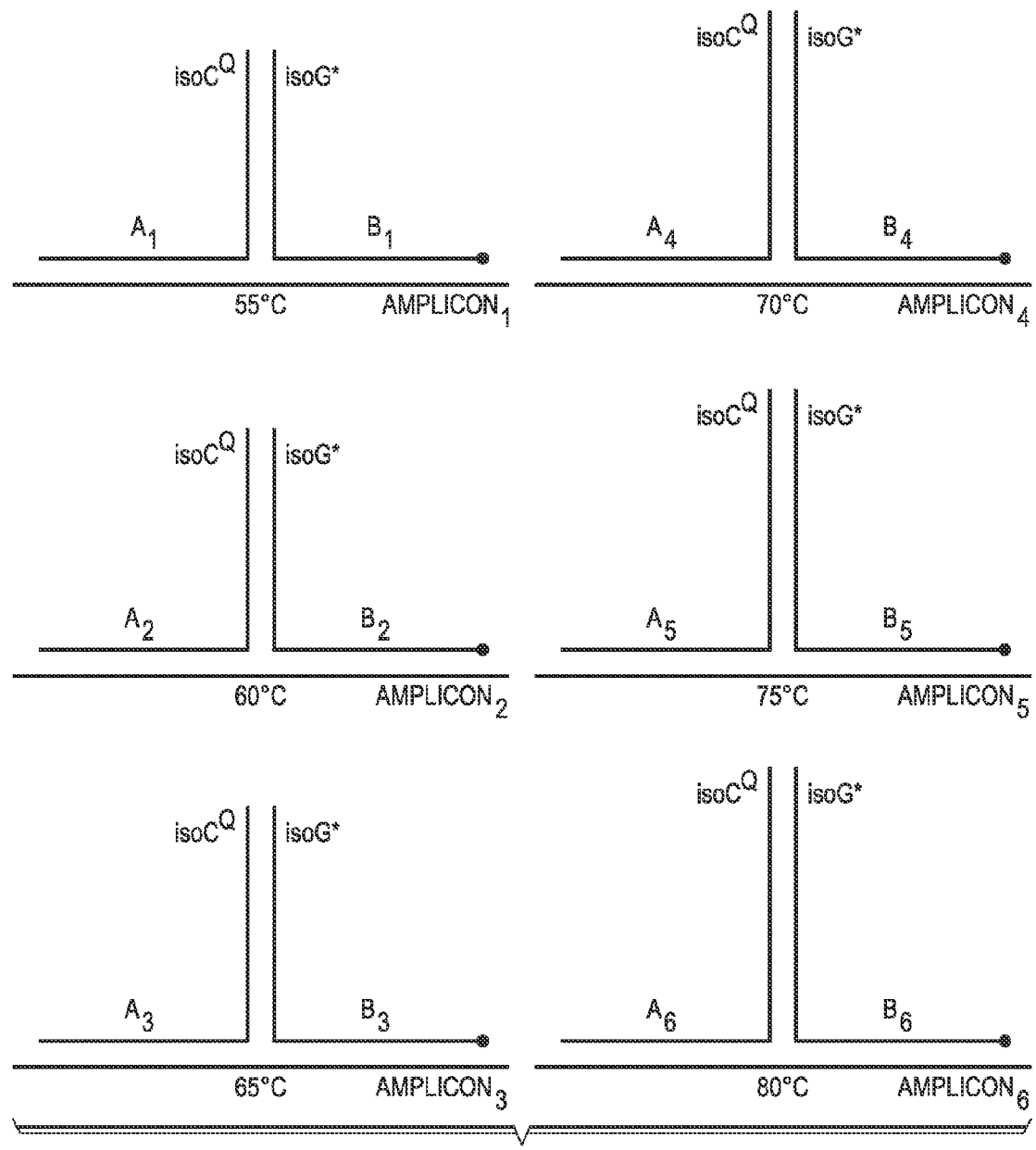

To multiplex the reaction, extendable probes are designed such that each pair has a unique $T_m$, thereby allowing for the use of melt analysis to determine the presence of the target sequence. Six pairs of probes can be designed, with each of the six having a $T_m$ of 55, 60, 65, 70, 75, or 80° C., thereby allowing a 6-plex reaction using only one color detection channel (FIG. 4B). Using multiple reporter-quencher pairs that are each detected on a unique color channel allows the performance of a 36-plex reaction with the use of six reporter-quencher pairs on six color channels.

Presence of a target sequence, in this embodiment, will start a chain reaction leading to a decrease in signal in the detection channel due to quenching of the reporter on the hairpin extendable probe. Then, upon melt analysis, the probe for which the target sequence was present in the reaction will produce an increased melt peak height or area under the curve at its predesigned $T_m$ (e.g., 60° C.) due to the separation of the reporter from the quencher (see, e.g., FIG. 1F). Alternatively, upon anneal analysis, the probe for which the target sequence was present in the reaction will produce a decreased anneal peak height or area under the curve at its predesigned $T_m$ (e.g., 65° C.) due to quenching of the reporter upon annealing (see, e.g., FIG. 2F).

Figure 5A:
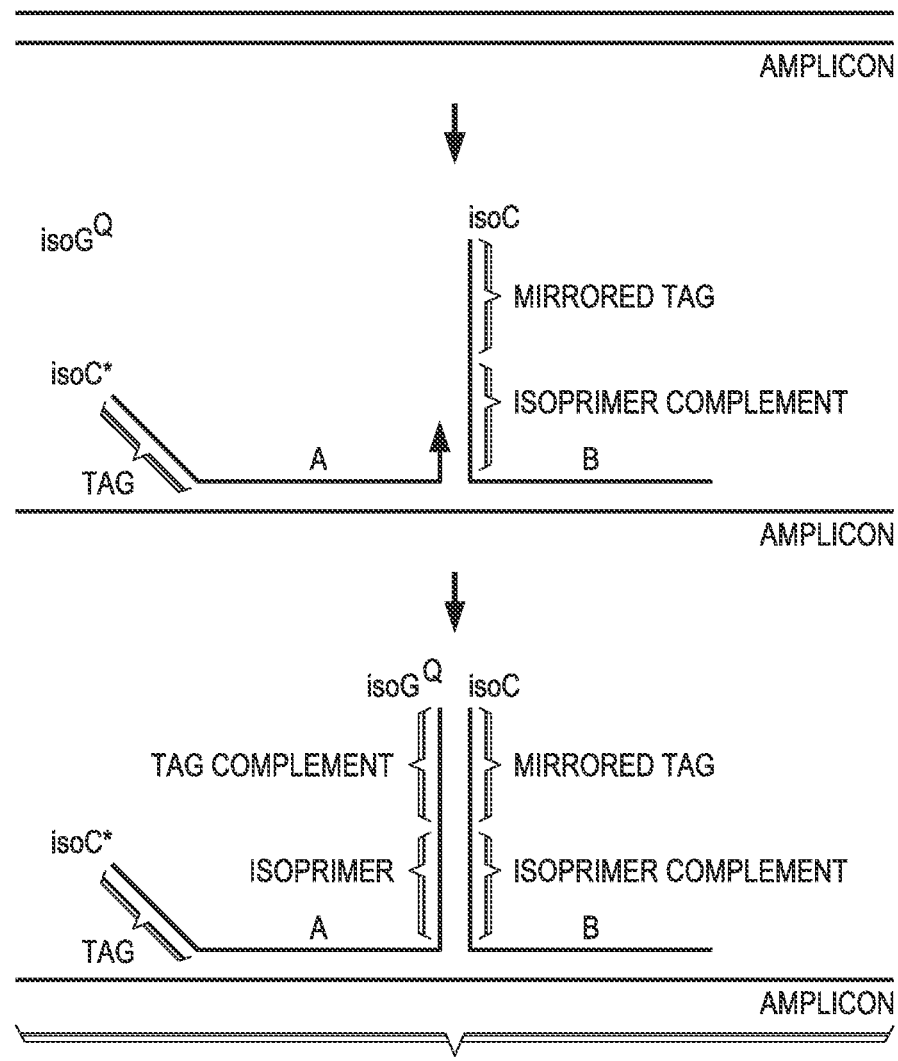
FIGS. 5A-C—A non-limiting exemplary schematic showing further T-junction probes.

A further modified T-junction extension probe system is shown in FIG. 5A. In this case, the downstream probe comprises an un-labeled isoC nucleotide at its 5' end, a "mirrored tag" sequence, optionally, a sequence including iso-base position (the "isoprimer complement"), a sequence complementary to the target sequence and, optionally, a modification block extension at its 3' end. The upstream sequence, on the other hand, comprises a fluorescently labeled isoC nucleotide, a "tag" sequence, optionally, an extension blocking modification, a sequence complementary to the target sequence and, optionally, a sequence that is complementary to one or more of the nucleotides of the "isoprimer complement" sequence of the downstream probe. When both probes hybridize to the target strand, the upstream probe can extend to incorporate sequence complementary to the isoprimer complement, the mirrored tag and to incorporate a quencher-labeled isoG nucleotide at its 3' end. Following extension the upstream probe is able to self-hybridize into a hairpin structure with the labeled 5' and 3' iso-based located adjacent to one another (see, e.g., FIG. 5C). Accordingly, the quencher labeled iso-G will quench the fluorescence of the labeled iso-C, which will quench the reporter and decrease the signal in the reaction.

Figure 5B:
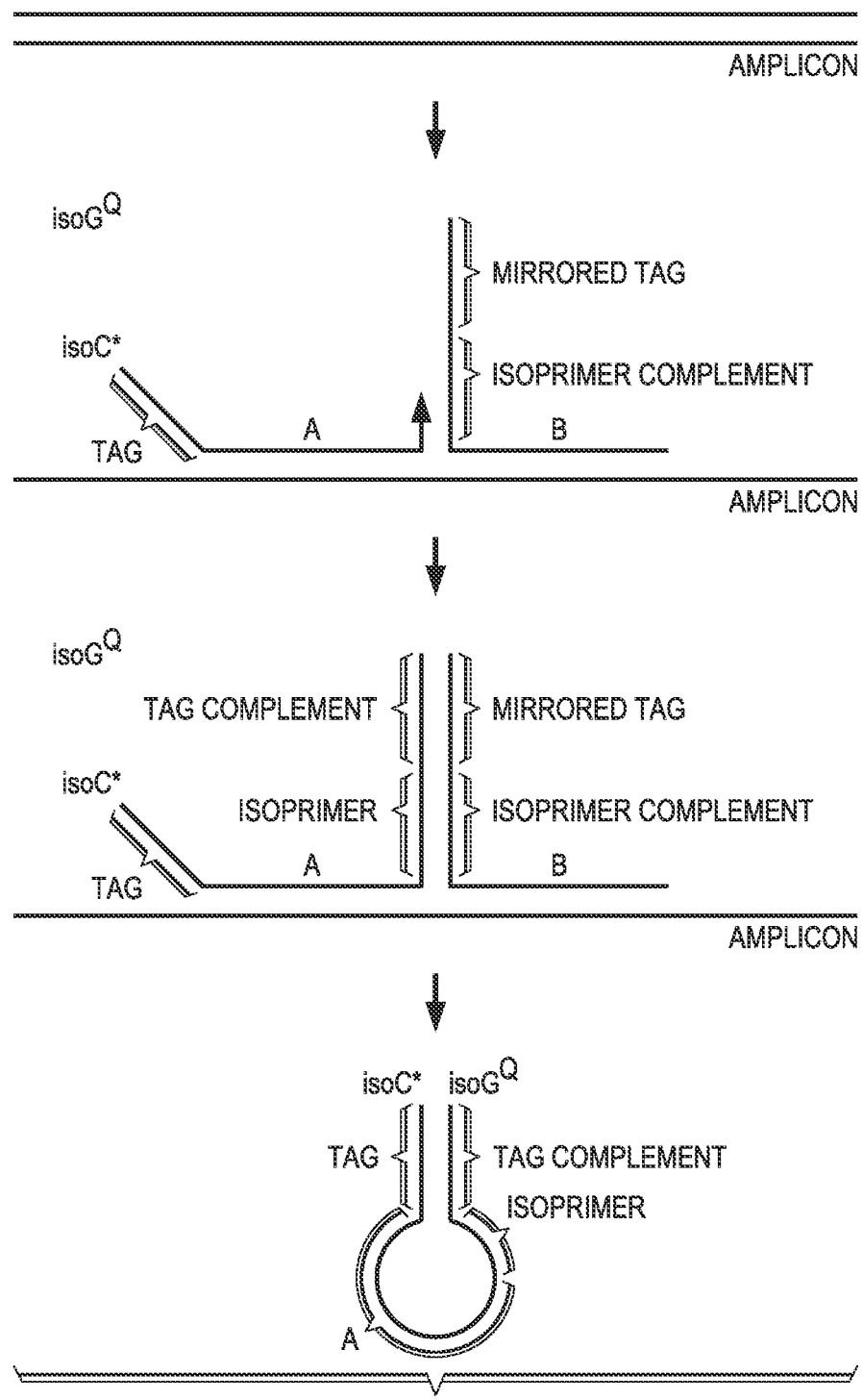

Still a further modified T-junction extension probe system is shown in FIG. 5B. In this case, the downstream probe comprises from 5' to 3', a "mirrored tag" sequence (or a portion of such a sequence), optionally, a sequence including iso-base position (the "isoprimer complement"), a sequence complementary to the target sequence and, optionally, a modification to block extension at its 3' end. The upstream sequence, on the other hand, comprises a fluorescently labeled isoC nucleotide, a "tag" sequence, optionally, an extension blocking modification, a sequence complementary to the target sequence and, optionally, a sequence that is complementary to one or more of the nucleotides of the "isoprimer complement" sequence of the downstream probe. When both probes hybridize to the target strand, the upstream probe can extend to incorporate sequence complementary to the isoprimer complement and the mirrored tag sequence (or a portion of this sequence). Following extension the upstream probe is able to self-hybridize into a hairpin structure and the 3' sequence can be further extended to incorporate a quencher-labeled isoG nucleotide at its 3' end. The resulting hairpin probe molecule includes labeled 5' and 3' iso-bases located adjacent to one another (see, e.g., FIG. 5C). Accordingly, the quencher labeled iso-G will quench the fluorescence of the labeled iso-C, which will quench the reporter and decrease the signal in the reaction.

Figure 5C:
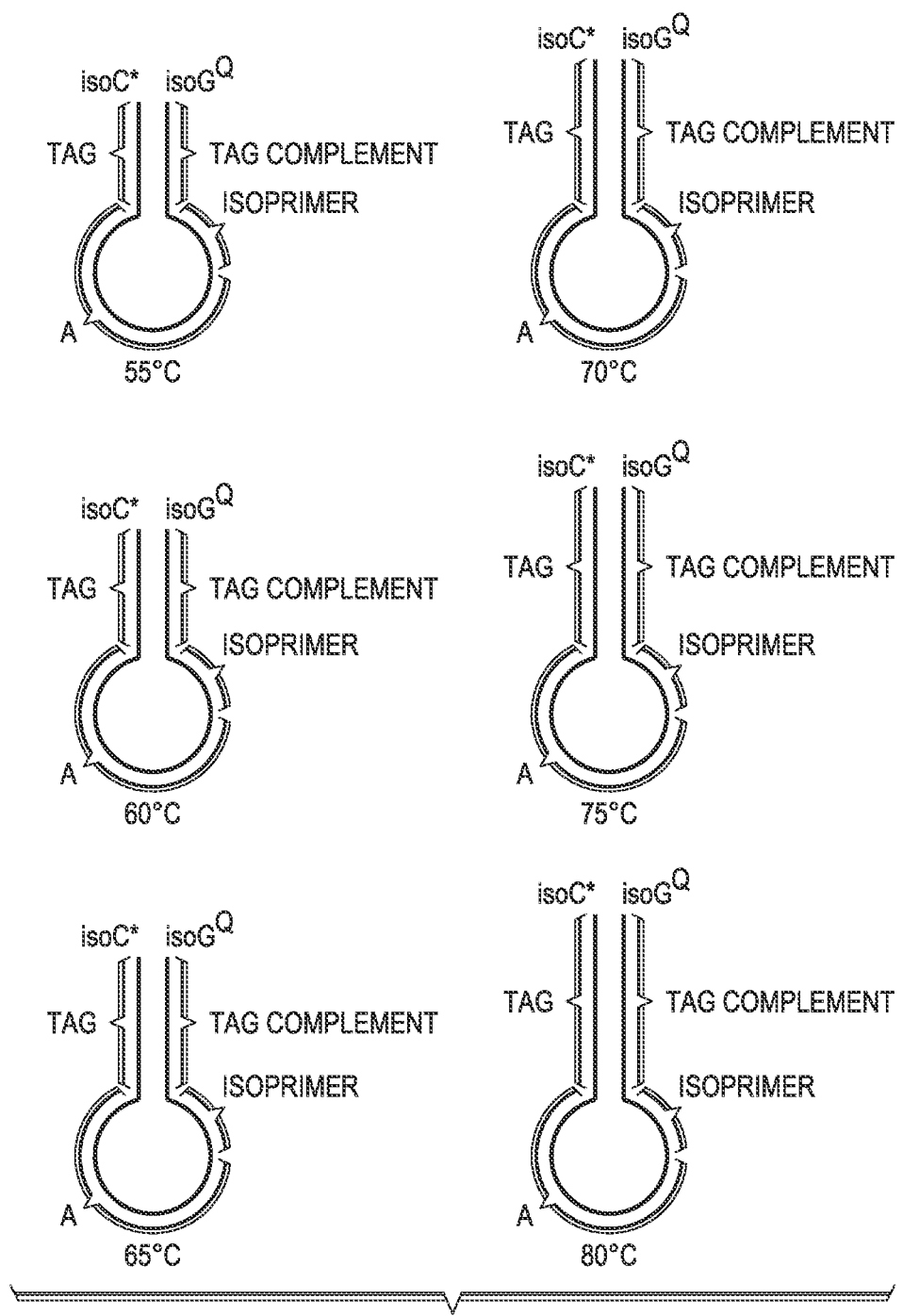

To multiplex a reaction with a hairpin type upstream probe described above, probes are designed such that each hairpins formed by the upstream probes have a unique $T_m$, thereby allowing for the use of melt analysis to determine the presence of the target sequence. In particular, the length and composition of the tag sequence can be changed to provide unique melt temperatures for each probe. For example, six different probes can be designed, with each of the six having a $T_m$ of 55, 60, 65, 70, 75, or 80° C., thereby allowing a 6-plex reaction using only one color detection channel (FIG. 5C). Using multiple reporter-quencher pairs that are each detected on a unique color channel allows the performance of a 36-plex reaction with the use of six reporter-quencher pairs on six color channels.

EXAMPLE 5

T-SNAP Probes for Single Nucleotide Polymorphism (SNP) Detection

Two probes that form a T-junction on a strand of an amplicon are designed as in the arrangement shown in Example 4 and FIG. 4A. The longer, downstream probe 2 (indicated as "B" in FIG. 5A) comprises an unlabeled isoG nucleotide at its 5' end. The shorter, upstream probe 1

(indicated as "A" in FIG. 4A) comprises an isoG-FAM nucleotide at its 5' end (optionally, a tag sequence and/or a modification to block extension) and sequence complementary to the target. When both probes hybridize to the target strand, SNP detection was based on the 3' extension of probe 1 (in this case without an isoprimer portion) with sequence complementary to the 5' portion of probe 2. Extension of Probe 1 terminates in after the incorporation of an isoG-dabcyl nucleotide against the isoC-FAM (FIGS. 4A and 4B).

TABLE 1

Exemplar T-SNAP Probes used in Phase 1 and Phase 2 (as described below)

| Probes | Sequence | SEQ ID NO: |
|---|---|---|
| T-Snap probe-1_3 | GACCACCGCCATTATTACGAACCAT | 1 |
| T-Snap probe-1_4 | GACCACCGCCATTATTACGAACCATC | 2 |
| T-Snap probe-1_5 | GACCACCGCCATTATTACGAACCATCA | 3 |
| T-Snap probe-1_6 | GACCACCGCCATTATTACGAACCATCAC | 4 |
| T-Snap probe-1_7 | GACCACCGCCATTATTACGAACCATCACG | 5 |
| T-Snap probe-1_8 | GACCACCGCCATTATTACGAACCATCACGA | 6 |
| T-Snap probe-1_9 | GACCACCGCCATTATTACGAACCATCACGAC | 7 |
| T-Snap probe-2 | /56-FAM/T/5Me-isodC/TCACTCGAGTCGTCGTGATGAGCTGTTTGAATATTAGATGGCACAC/3SpC3/ | 8 |

TABLE 2

Staphylococcus epidermidis PCR primers

| Primer | Sequence | SEQ ID NO: |
|---|---|---|
| Sepi-Fwd | TCAGCAGTTGAAGGGACAGAT | 9 |
| Sepi-Rev | CCAGAACAATGAATGGTTAAGG | 10 |

Figure 9:
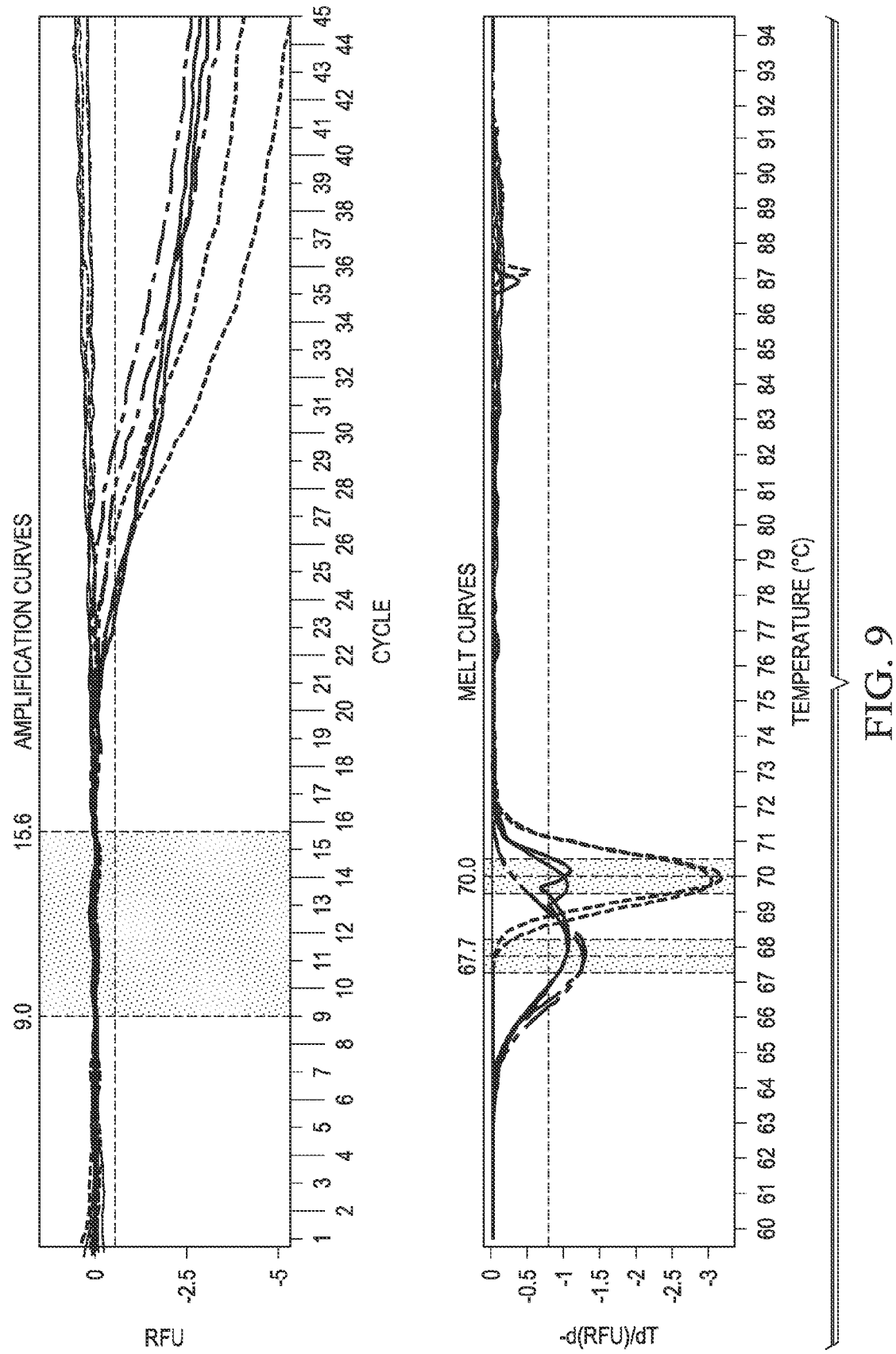
FIGS. 9-10—Results of asymmetric PCR. Graphs show amplification (upper panel) and melt (lower panel) curves for the tested probe using different concentrations of PCR primers. PCR primers were used at three difference concentrations: [FWD]/[REV]=80/40 nM (dashed lines); [FWD]/[REV]=40/40 nM (broken lines); and [FWD]/[REV]=40/80 nM (solid lines).
Figure 10:
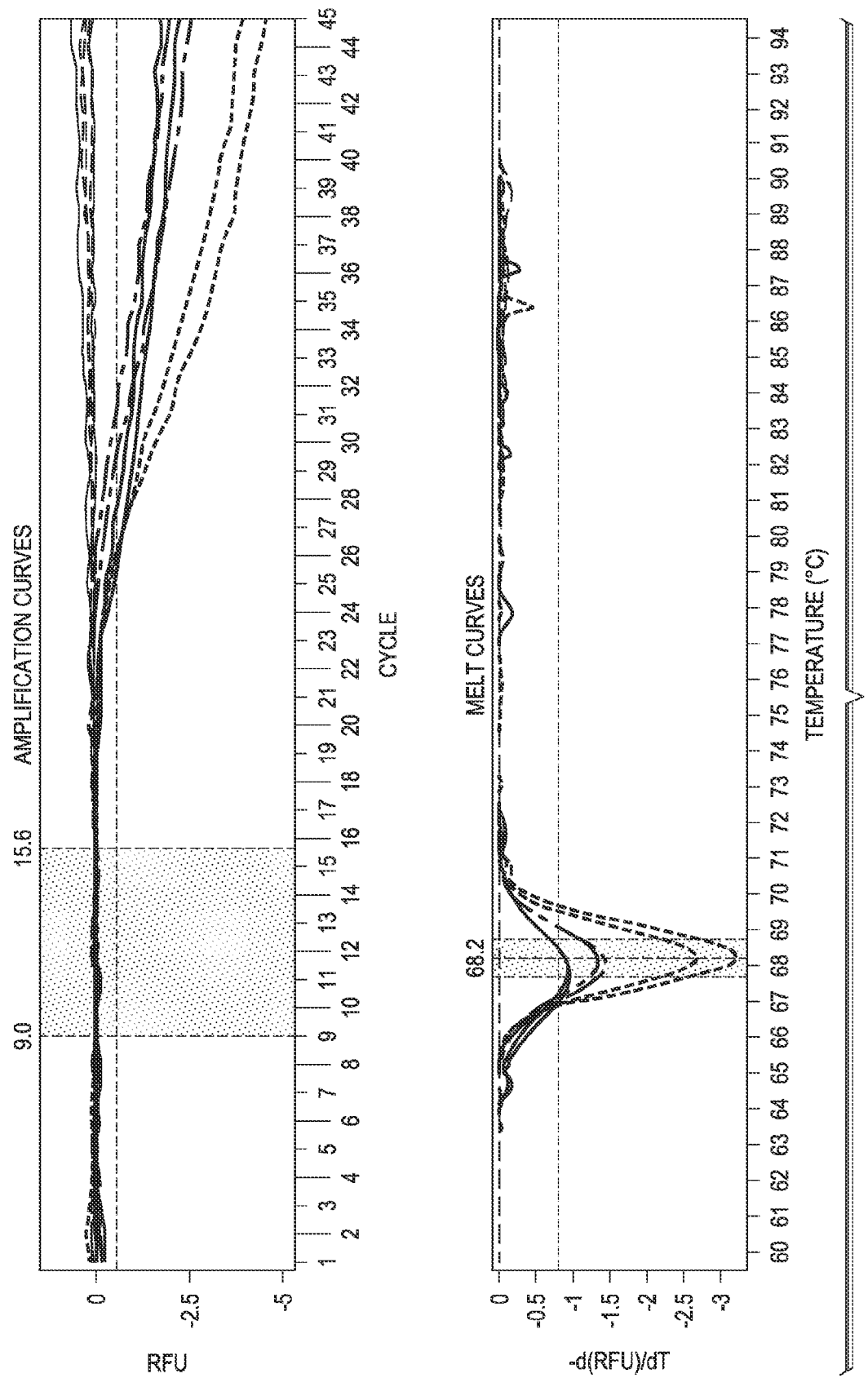

Phase 1
Formation of T-junction in Extension Reaction
Extension assay was used to evaluate probe 1 designs with variable arm lengths (6-9 nucleotides). Briefly, 10 nM of probe 1 and 20 nM of probe 2 were added to a reaction mixture containing BTP-KCl pH 9.1 buffer, 2.5 mM dNTPs, 2.5 mM MgCl$_2$, 1 mM dabcyl-isoG, Titanium Taq enzyme (Clontech). Multiple replicates were used with template and without template. The template used was synthetic amplicon sequence, ultramer from IDT. The extension reaction was carried out for 33 minutes incubation at 58° C. followed by a melt analysis protocol: 60° C. 20 sec and 95° C. 1 sec followed with a cooling step at 40° C. The results showed that, at these concentrations, T-junction forms with all probes only in the presence of template (FIG. 9).
Formation of T-junction in Asymmetric PCR
Probe 1 with arm length of 7 nucleotides was further evaluated for T-junction formation in asymmetric PCR. The sequence specific segments of both probes 1 and 2 were shortened for better specificity and the new sequences are shown in Table 3. A primer titration was also included to determine specificity of the probes to the targeted template. Briefly, 80 nM of Probe 1 and 40 nM of probe 2 were added to a reaction mixture containing BTP-KCl pH 9.1 buffer, 2.5 mM dNTPs, 2.5 mM MgCl$_2$, 1 mM Dabcyl-isoG, Titanium Taq enzyme (Clontech). Multiple replicates were used with template and without template. The template used was synthetic amplicon sequence from, ultramer from IDT (100 fM) and PCR primers were used at three different concentrations (Fwd/Rev of 80/40 nM, 40/40 nM and 40/80 mM). A specific product was detected with all conditions. The results of these studies showed that asymmetric PCR favoring the creation of the targeted template produced distinct and sharp melt curves (FIGS. 9-10).

TABLE 3

Probes used to asymmetric PCR assay detailed above.

| Probe name | Sequence | SED ID NO: |
|---|---|---|
| Probe 2-2 | /56-FAM/T/iMe-isodC/TCACTCG AGT CGT CGT GATG AGCTGTTTGAATATTAGATGGCAC/3SpC3/ | 11 |
| Probe 1_7-2 | CCACCGCCATTATTACGAAC<u>CATCACG</u> | 12 |

The underlined nucleotides represent the probe "arm".

Figure 11:
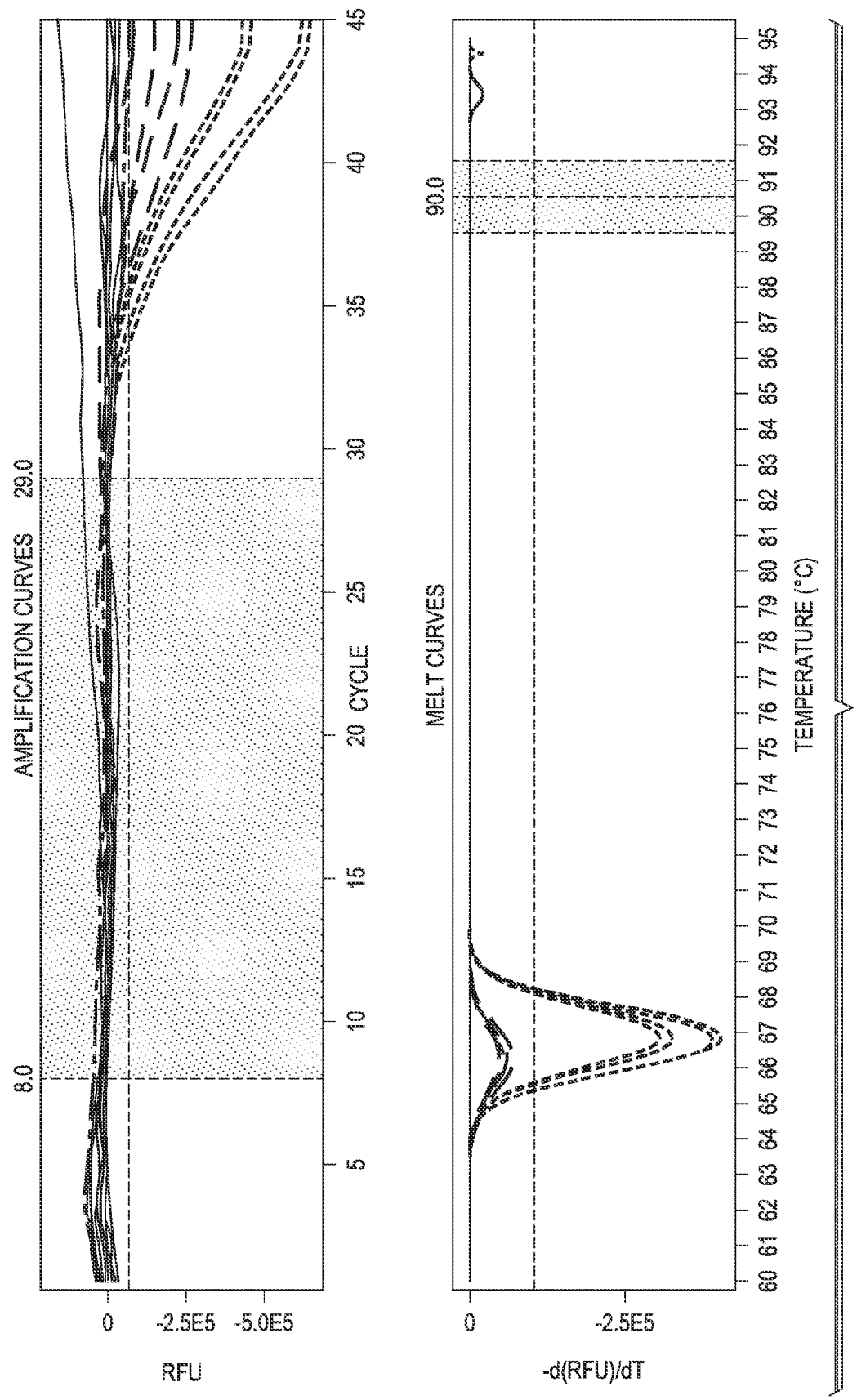
FIG. 11—SNP detection. Graphs show amplification (upper panel) and melt (lower panel) curves for the SNP detection probes. In the amplification curve results: probe SNP1_7-2,10 (solid lines); probe SNP1_7-2,6 (broken lines); probe SNP1_7-2,3 (long dashed line; Avg. Ct. 38.4); and control (short dashed lines; Avg. Ct. 34.2). In the melt curve results, the control (short dashed lines) Tm was 66.7° C. and the Tm for probe SNP1_7-2,3 (long dashed lines) was 66.1° C. The probe sequences are shown in Table 4.

Phase 2—SNP Detection
Multiple designs were created to test the ability of detecting SNPs with T-SNAP approach. Probes used for the studies are listed in Table 4 below. The SNP was placed at 3 different locations on sequence specific segment of probe 2, 6 nucleotides from the junction, 10 nucleotides from the junction and 3 nucleotides from the junction. The results showed SNP Probes 1_7-2, 6 and 1_7-2, 10 exhibited no extension, signifying good SNP identification, while SNP Probe 1_7-2, 3 exhibited minimal extension, signifying non-optimal SNP identification (FIG. 11).

TABLE 4

SNP probes.

| Probe name | Sequence | SEQ ID NO: |
|---|---|---|
| Probe 2-2 | /56-FAM/T/iMe-isodC/TCACTCG AGT CGT CGT GATG AGCTGTTTGAATATTAGATGGCAC/3SpC3/ | 13 |
| Probe 1_7-2 (control) | CCACCGCCATTATTACGAAC<u>CATCACG</u> | 14 |
| SNP 1_7-2,6 | CCACCGCCATTATT<u>T</u>CGAAC<u>CATCACG</u> | 15 |
| SNP 1_7-2,10 | CCACCGCCAT<u>A</u>ATTACGAAC<u>CATCACG</u> | 16 |
| SNP 1_7-2,3 | CCACCGCCATTATTACG<u>T</u>AC<u>CATCACG</u> | 17 |

The underlined nucleotides represent the probe "arm". The double-underlined nucleotide represents the SNP placement.

Phase 3—T-SNAP in Single-plex PCR-full Length Probes
Probes were designed according to the diagram in FIG. 5A, without the optional "isoprimer" and "isoprimer complement" elements. The designed probe sequences are shown below in Table 5, Probe 1 and Probe 2 sequences correspond to the "A" and "B" probes of FIG. 5A, respectively. For the studies asymmetric PCR reaction was carried out as described above. The primers were used at Fwd/Rev=80/40 nM, and the 500 fM of the template. Preliminary PCR data showed that the amplitude of the melt curve was greater when the arm is part of the hairpin stem as in probe FL-probe1_8_04 (FIG. 12).

TABLE 5

Full length probe sequences.

| Probe name | Sequence | SEQ ID NO: |
|---|---|---|
| FL-probe1_8_01 | /56FAM/T/iMe-isodC/TCT TTC TCA ATT GACCACCGCCATTATTACGAAC<u>CATCACGA</u> | 18 |
| FL-probe1_8_04 | /56FAM/T/iMe-isodC/TCT TTC TCA TCG GACCACCGCCATTATTACGAAC<u>CATCACGA</u> | 19 |
| FL-probe2_01 | /5Me-isodC/TCTTTCTCAATT<u>TCGTGATG</u>AGCTG TTTGAATATTAGATGGCACAC/3SpC3/ | 20 |
| FL-probe2_07 | /5Me-isodC/TCTTTCTCA<u>TCGTGATG</u>AGCTG TTTGAATATTAGATGGCACAC/3SpC3/ | 21 |

The underlined nucleotides represent the probe "arm".

EXAMPLE 5

Additional Hairpin Probe Detection Systems

Figure 6:
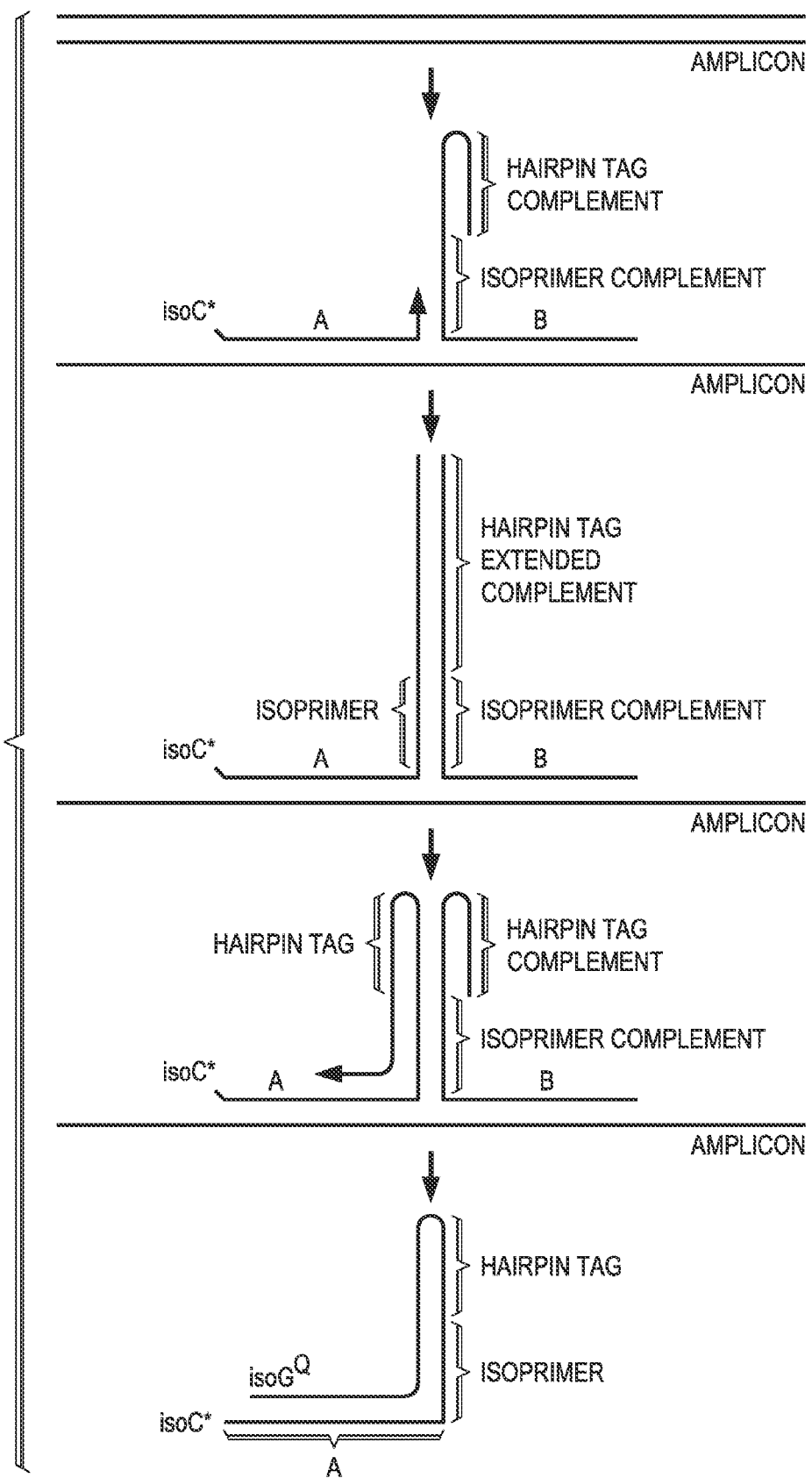
FIG. 6—A further non-limiting exemplary schematic showing T-junction probes. Two probes are designed to form a T-junction on a strand of an amplicon. The upstream probe comprises a reporter-labeled isoG nucleotide ("isoG*") at its 5' end, a sequence complementary to the amplicon (indicated as "A") and, optionally, one or more nucleotides that can base-pair with the "isoprimer complement" of the downstream probe. The downstream probe comprises a sequence that base pairs with itself to form a hair pin ("hairpin tag complement"); optionally, a sequence that includes isoG and/or isoC positions (the "isoprimer complement") and a sequence that complementary to the amplicon (marked as "B"). Extension of the upstream probe will synthesize sequences complementary to the "isoprimer complement" and the "hairpin tag complement" on the downstream probe. The extended upstream probe now includes a hairpin sequence, which allows the probe to be further extended and synthesize sequences complementary to the "isoprimer" and the "A" sequences and to incorporate a quencher-labeled isoC nucleotide (isoC$^Q$). The probes can be designed to have unique melt temperatures ($T_m$), such as by adjusting the sequence and length of the hairpin tag, the "A" sequence or the isoprimer sequence. A melt analysis can be performed to differentiation probes having different melt temperatures (and thus unquenching at different temperatures).

Further hairpin probe detection systems are detailed in FIG. 6. In this system, two probes are designed to form a T-junction on a strand of an amplicon. The upstream probe comprises a reporter-labeled isoG nucleotide ("isoG*") at its 5' end, a sequence complementary to the amplicon (indicated as "A") and, optionally, one or more nucleotides that can base-pair with the "isoprimer complement" of the downstream probe. The downstream probe comprises a sequence that base pairs with itself to form a hair pin ("hairpin tag complement"); a sequence that includes isoG and/or isoC positions (the "isoprimer complement") and a sequence that complementary to the amplicon (marked as "B"). Extension of the upstream probe will synthesize sequences complementary to the "isoprimer complement" and the "hairpin tag complement" on the downstream probe. The extended upstream probe now includes a hairpin sequence, which allows the probe to be further extended and synthesize sequences complementary to the (optional) "isoprimer" and the "A" sequences and to incorporate a quencher-labeled isoC nucleotide. The probes can be designed to have unique melt temperatures ($T_m$), such as by adjusting the sequence and length of the hairpin tag, the "A" sequence or the isoprimer sequence. A melt analysis can be performed to differentiation probes having different melt temperatures (and thus unquenching at different temperatures).

Figure 7:
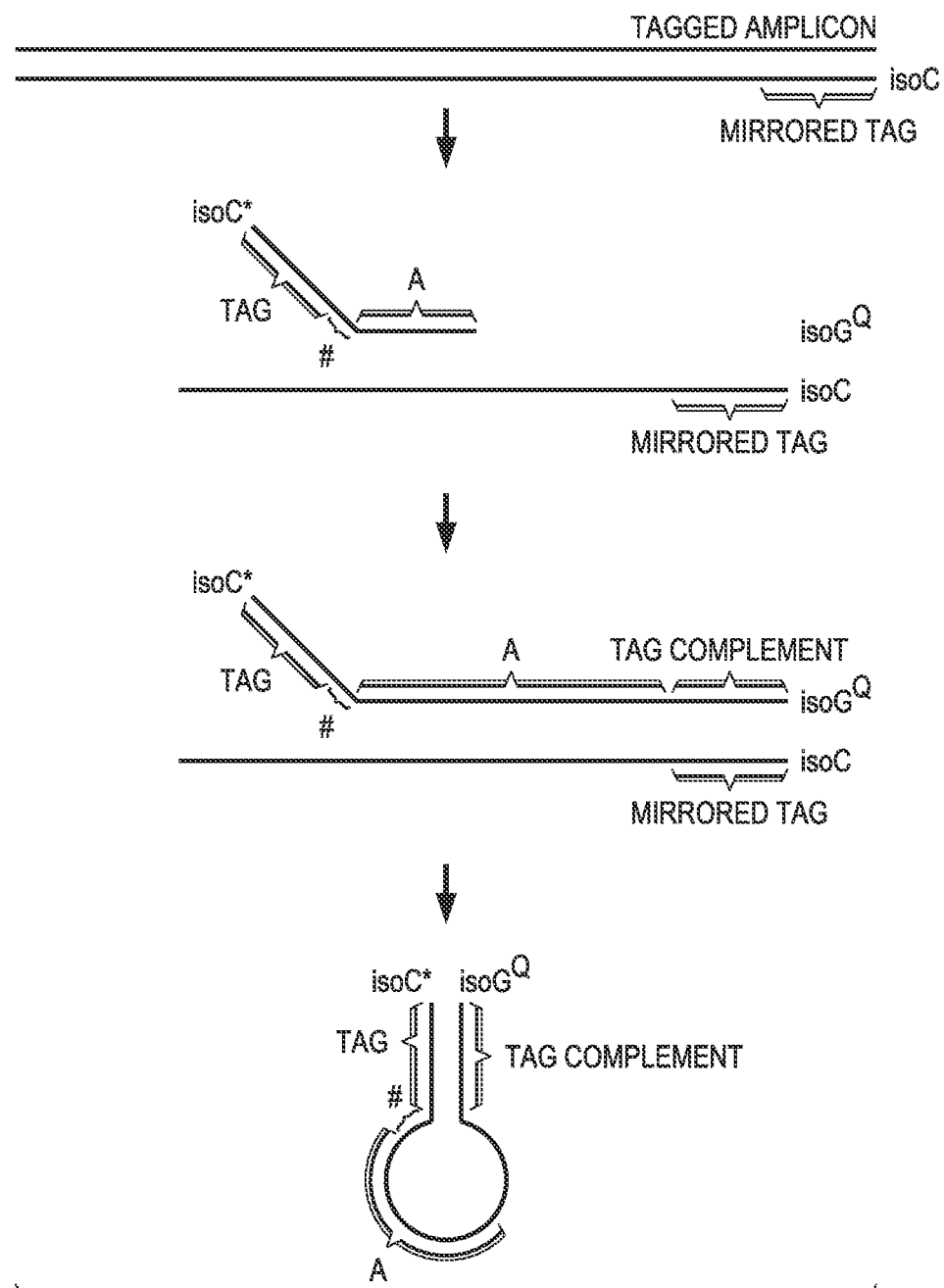
FIG. 7—A non-limiting exemplary schematic showing a probe system of the embodiments. In this embodiment, the target sequence is amplified using at least a first tagged primer. Specifically, the tagged primer comprises a 5' isoC followed by a "mirrored tag" sequence. The reporter probe comprises a reporter-labeled isoC nucleotide ("isoC*") at its 5' end, a tag sequence ("tag"), optionally and extension blocking modification; and a sequence complementary to the amplicon (indicated as "A"). In the presence of a target amplicon the reporter probe hybridizes to the tagged strand of the amplicon and is extended to end of the amplicon to incorporate sequences of the "tag complement" and a 3' quencher-labeled isoG ("isoG$^Q$"). The extended reporter probe now includes a tag and tag complement sequence, which allows the probe to form a hairpin and thereby quench the fluorescence of the labeled isoC. The probes can be designed to have unique melt temperatures ($T_m$), such as by adjusting the sequence and length of the tag sequence. Thus, a melt analysis can be performed to differentiation probes having different melt temperatures (and thus unquenching at different temperatures).
Figure 8:
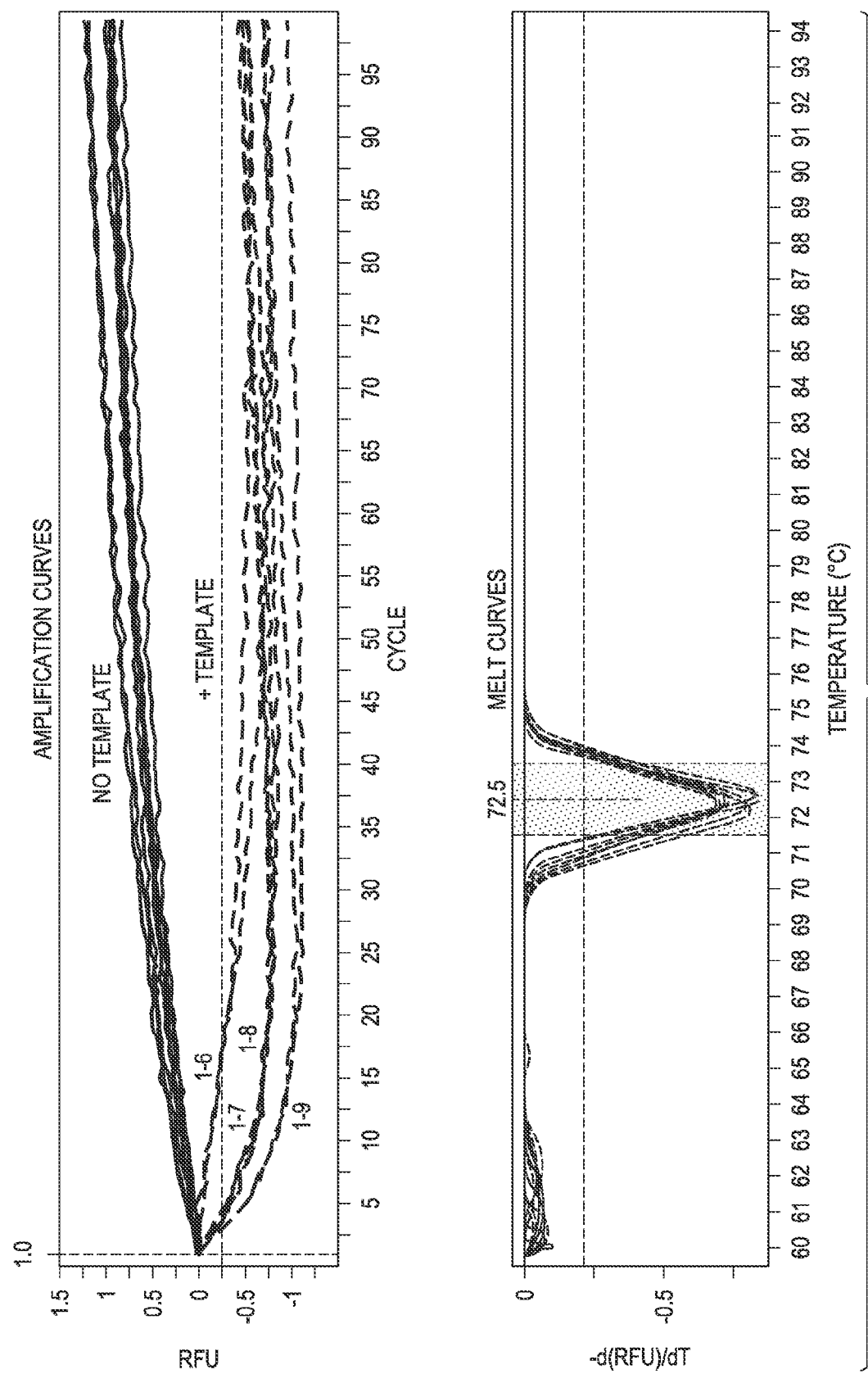
FIG. 8—Extension reaction variable probe 1 and probe 2. Graphs show amplification (upper panel) and melt (lower panel) curves for the tested probes. Probe 1 with arm lengths of 6 (1-6), 7 (1-7), 8 (1-8), or 9 (1-9) nucleotides produced quenching at 5'FAM of probe 2 only when template was present. All products have similar $T_m$s.

Yet a further example of a hairpin probe detection system is shown in FIG. 7. In this system, the target sequence is amplified using at least a first tagged primer. Specifically, the tagged primer comprises a 5' isoC followed by a "mirrored tag" sequence (and a target-specific sequence). The reporter probe comprises a reporter-labeled isoC nucleotide ("isoC*") at its 5' end, a tag sequence ("tag"), optionally and extension blocking modification; and a sequence complementary to the amplicon (indicated as "A"). In the presence of a target amplicon, the reporter probe hybridizes to the amplicon and is extended to end of the amplicon to incorporate sequences of the "tag complement" and a 3' quencher-labeled isoG ("isoG$^Q$"). The extended reporter probe now includes a tag and tag complement sequence, which allows the probe to form a hairpin and thereby quench the fluorescence of the labeled isoC. The probes can be designed to have unique melt temperatures ($T_m$), such as by adjusting the sequence and length of the tag sequence. Thus, a melt analysis can be performed to differentiation probes having different melt temperatures (and thus unquenching at different temperatures).

* * *

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.
U.S. Pat. Nos. 4,942,124; 4,284,412; 4,989,977; 4,498,766; 5,478,722; 4,857,451; 4,774,189; 4,767,206; 4,714,682; 5,160,974; 4,661,913; 5,654,413; 5,656,493; 5,716,784; 5,736,330; 5,837,832; 5,837,860; 5,981,180; 5,994,056; 5,736,330; 5,981,180; 6,057,107; 6,030,787; 6,046,807; 6,057,107; 6,103,463; 6,139,800; 6,174,670; 6,268,222; 6,322,971; 6,366,354; 6,410,278; 6,411,904; 6,449,562; 6,514,295; 6,524,793; 6,528,165; 6,592,822; 6,939,720; 6,977,161; 7,226,737; 7,645,868; and 7,955,802.
U.S. Published Publication Nos. 2005/0191625; 2008/0182312; and 2009/0148849.
International (PCT) Publication No. WO/2011/050278.
McMinn et al., *J. Am. Chem. Soc.* 1999, 121:11585.
Ren, et al., *J. Am. Chem. Soc.* 1996, 118:1671.

What is claimed is:

1. An in vitro method for detecting the presence of a target nucleic acid comprising:
 (a) contacting the sample with a first set of probes, said set of probes comprising an upstream probe comprising, from 5' to 3', (i) at least one non-natural nucleotide labeled with a first member of a reporter-quencher pair; (ii) a tag sequence; and (iii) a sequence complementary to a first region on a first strand of the target nucleic acid; and a downstream probe comprising, from 5' to 3', (i) a mirrored tag sequence having the same sequence as the tag sequence of the upstream probe; and (ii) a sequence complementary to a second region on a first strand of the target nucleic acid downstream of the first region, wherein the upstream probe comprises a 3' sequence of 3 or more bases complementary to the downstream probe such that when hybridized to the target nucleic acid the set of probes form a T-junction;
 (b) extending the upstream probe to synthesize sequences complementary to the mirrored tag sequence on the downstream probe to form an extended upstream probe;
 (c) allowing the extended upstream probe to hybridize to itself to form a hairpin probe;
 (d) extending the hairpin probe in the presence of a non-natural nucleotide labeled with a second member of a reporter-quencher pair that is capable of base-pairing with the at least one non-natural nucleotide in the upstream probe; and
 (e) detecting the target nucleic acid by detecting a change in signal from the label on the upstream probe and the hairpin probe.

2. The method of claim 1, wherein the upstream probe comprises a 3' sequence of 3 to 10 bases complementary to the tag sequence of the downstream probe.

3. The method of claim 1, wherein the downstream probe further comprises (iii) a isoprimer complement sequence including one or more non-natural bases between the mirrored tag sequence having the same sequence as the tag sequence of the upstream probe and the sequence complementary to a second region on a first strand of the target nucleic acid downstream of the first region.

4. The method of claim 1, wherein before being extended the upstream and downstream probes have a melt point of less than 55° C. in the absence of the target nucleic acid.

5. The method of claim 1, wherein detecting a change in signal from the label comprises detecting a change in signal from the reporter as the temperature of the sample is changed.

6. The method of claim 1, wherein the downstream probe is attached a solid support.

7. The method of claim 1, wherein the at least one non-natural nucleotide or the quencher-labeled non-natural nucleotide is isoG and the other is isoC.

8. The method of claim 1, further comprising:
 (a) contacting the sample with a second, third, fourth, fifth or sixth set of probes, each set of probes comprising an upstream probe comprising, from 5' to 3', (i) at least one non-natural nucleotide labeled with a first member of a reporter-quencher pair; (ii) a tag sequence; and (iii) a sequence complementary to a first region on a first strand of a second, third, fourth, fifth or sixth target nucleic acid; and a downstream probe comprising, from 5' to 3', (i) a mirrored tag sequence having the same sequence as the tag sequence of the upstream probe; and (ii) a sequence complementary to a second region on a first strand of the second, third, fourth, fifth or sixth target nucleic acid downstream of the first region, wherein the upstream probe comprises a 3' sequence of 3 or more bases complementary to the downstream probe such that when hybridized to the target nucleic acid the set of probes form a T-junction;
 (b) extending the upstream probe to synthesize sequences complementary to the mirrored tag sequence on the downstream probe to form an extended upstream probe;
 (c) allowing the extended upstream probe to hybridize to itself to form a hairpin probe;
 (d) extending the hairpin probe in the presence of a non-natural nucleotide labeled with a second member of a reporter-quencher pair that is capable of base-pairing with the at least one non-natural nucleotide in the upstream probe; and
 (e) detecting the second, third, fourth, fifth or sixth target nucleic acid by detecting a change in signal from the label on the upstream probe and the hairpin probe.

9. The method of claim 1, wherein the hairpin probes formed by the first and second set of probes comprise distinguishable melt points.

10. The method of claim 8, wherein the hairpin probes formed by the first, second, third, fourth, fifth and sixth set of probes each comprise a distinguishable labels or distinguishable melt points.

11. An in vitro method for detecting the presence of one or both of a first and second target nucleic acid molecule in a sample comprising:
 (a) contacting the sample with at least a first and second set of primers, each set of primers comprising a first primer comprising, from 5' to 3', (i) a reporter, (ii) a hairpin with a known melt point, (iii) a polymerase extension-blocking modification, (iv) at least one non-natural nucleotide, and (v) a target-specific sequence, complementary to a first region on the first strand of a target nucleic acid; and a second primer comprising a sequence complementary to a region on a second strand of the target nucleic acid, wherein the reporters from the first and second set of primer are the same and wherein the first and second set of primers comprise hairpins with distinguishable melt points;
 (b) amplifying the target nucleic acids with the first and second set of primers, wherein said amplifying is performed in the presence of a quencher-labeled non-natural nucleotide that base-pairs with the non-natural nucleotide of the first primer of the first and second primer sets;

(c) detecting the presence of a target nucleic acid molecule by detecting a quenching of signal from the reporter; and (d) determining whether the quenching of signal from the reporter resulted from the presence of the first target nucleic acid molecule, the second target nucleic acid molecule, or both by changing the temperature of the sample and determining the melt point or melt peaks corresponding to unquenching of the reporter, thereby detecting the presence of one or both of the first and second target nucleic acid molecules.

12. The method of claim 11, wherein the reporter is a fluorophore.

13. The method of claim 12, wherein the quenching of the signal is a decrease in a fluorescent signal.

14. The method of claim 11, wherein one of the at least one non-natural nucleotide and the quencher-labeled non-natural nucleotide is isoG and the other is isoC.

15. The method of claim 11, wherein the first and second set of primers comprise a first primer having hairpins with melt points that differ by between 2° C. and 10° C.

16. The method of claim 11, further comprising:
(a) contacting the sample with at least a third, fourth, fifth or sixth set of primers, each set of primers comprising a first primer comprising, from 5' to 3', (i) a reporter, (ii) a hairpin with a known melt point, (iii) a polymerase extension-blocking modification, (iv) at least one non-natural nucleotide, and (v) a target-specific sequence, complementary to a first region on the first strand of a third, fourth, fifth or sixth target nucleic acid; and a second primer comprising a sequence complementary to a region on a second strand of the third, fourth, fifth or sixth target nucleic acid;
(b) amplifying a third, fourth, fifth or sixth target nucleic acid with the third, fourth, fifth or sixth set of primers, wherein said amplifying is performed in the presence of a quencher-labeled non-natural nucleotide that base-pairs with the non-natural nucleotide of the first primer; and
(c) detecting the presence of the third, fourth, fifth or sixth target nucleic acid by detecting a quenching of signal from a distinguishable reporter and/or by determining the melt point or melt peaks corresponding to unquenching of the reporter as the temperature of the sample is changed.

17. A method for detecting the presence of none or both of a first and second target nucleic acid comprising:

(a) contacting the a sample with at least a first and second target-specific primer-probe set, each primer-probe set comprising:
(i) a primer complementary to a first region on a first strand of the target nucleic acid;
(ii) a target-specific probe complementary to a second region on the first strand of the target nucleic acid downstream of the first region and comprising a 5' tag sequence that is not complementary to the target nucleic acid;
(iii) a first assay probe comprising a first region which is complementary to the tag sequence from the target-specific probe and second region, downstream of the first region comprising a polymerase extension-blocking modification; and
(iv) a second assay probe complementary to the second region of the first assay probe,
wherein one of the first and second assay probes is labeled with a reporter and the other is labeled with a quencher;

(b) incubating the sample under conditions suitable for hybridization of the target nucleic acid with the target-specific primer and the target-specific probe of the primer-probe sets;

(c) cleaving the hybridized target-specific probe with a nucleic acid polymerase having exonuclease activity to release the tag sequence from the target-specific probe;

(d) hybridizing the released tag sequence with the first assay probe;

(e) extending the hybridized tag sequence along the first assay probe to the extension blocking sequence thereby cleaving a portion of the second assay probe hybridized to the first assay probe, wherein the first and second assay probes have a known melt point after said cleaving and wherein the melt point of the first and second assay probes of the first primer-probe set is distinguishable from the melt point of the first and second assay probes of the second primer-probe after said cleaving;

(f) detecting a target nucleic acid by determining whether the second assay probe of the first target-specific primer-probe set, the second target-specific primer-probe set, or both, was cleaved by performing melt curve analysis on the first and second assay probes, wherein a temperature shift of a melt peak corresponding to a particular first and second assay probe set indicates that the second assay probe was cleaved and the indicates the presence of the first or second target nucleic acid.

* * * * *

UNITED STATES PATENT AND TRADEMARK OFFICE
CERTIFICATE OF CORRECTION

PATENT NO. : 9,657,332 B2
APPLICATION NO. : 14/456239
DATED : May 23, 2017
INVENTOR(S) : Doug Whitman et al.

Page 1 of 1

It is certified that error appears in the above-identified patent and that said Letters Patent is hereby corrected as shown below:

In the Claims

In Claim 17, Column 58, Line 1, delete the word "the".

Signed and Sealed this
Twenty-fifth Day of July, 2017

Joseph Matal
*Performing the Functions and Duties of the
Under Secretary of Commerce for Intellectual Property and
Director of the United States Patent and Trademark Office*

SEQUENCE LISTING

<160> NUMBER OF SEQ ID NOS: 21

<210> SEQ ID NO 1
<211> LENGTH: 25

```
<212> TYPE: DNA
<213> ORGANISM: Artificial sequence
<220> FEATURE:
<223> OTHER INFORMATION: Synthetic probe

<400> SEQUENCE: 1
gaccaccgcc attattacga accat                                         25

<210> SEQ ID NO 2
<211> LENGTH: 26
<212> TYPE: DNA
<213> ORGANISM: Artificial sequence
<220> FEATURE:
<223> OTHER INFORMATION: Synthetic probe

<400> SEQUENCE: 2
gaccaccgcc attattacga accatc                                        26

<210> SEQ ID NO 3
<211> LENGTH: 27
<212> TYPE: DNA
<213> ORGANISM: Artificial sequence
<220> FEATURE:
<223> OTHER INFORMATION: Synthetic probe

<400> SEQUENCE: 3
gaccaccgcc attattacga accatca                                       27

<210> SEQ ID NO 4
<211> LENGTH: 28
<212> TYPE: DNA
<213> ORGANISM: Artificial sequence
<220> FEATURE:
<223> OTHER INFORMATION: Synthetic probe

<400> SEQUENCE: 4
gaccaccgcc attattacga accatcac                                      28

<210> SEQ ID NO 5
<211> LENGTH: 29
<212> TYPE: DNA
<213> ORGANISM: Artificial sequence
<220> FEATURE:
<223> OTHER INFORMATION: Synthetic probe

<400> SEQUENCE: 5
gaccaccgcc attattacga accatcacg                                     29

<210> SEQ ID NO 6
<211> LENGTH: 30
<212> TYPE: DNA
<213> ORGANISM: Artificial sequence
<220> FEATURE:
<223> OTHER INFORMATION: Synthetic probe

<400> SEQUENCE: 6
gaccaccgcc attattacga accatcacga                                    30

<210> SEQ ID NO 7
<211> LENGTH: 31
<212> TYPE: DNA
<213> ORGANISM: Artificial sequence
<220> FEATURE:
<223> OTHER INFORMATION: Synthetic probe

<400> SEQUENCE: 7
```

-continued gaccaccgcc attattacga accatcacga c                31

<210> SEQ ID NO 8
<211> LENGTH: 46
<212> TYPE: DNA
<213> ORGANISM: Artificial sequence
<220> FEATURE:
<223> OTHER INFORMATION: Synthetic probe

<400> SEQUENCE: 8
tcactcgagt cgtcgtgatg agctgtttga atattagatg gcacac                46

<210> SEQ ID NO 9
<211> LENGTH: 21
<212> TYPE: DNA
<213> ORGANISM: Staphylococcus epidermidis

<400> SEQUENCE: 9
tcagcagttg aagggacaga t                21

<210> SEQ ID NO 10
<211> LENGTH: 22
<212> TYPE: DNA
<213> ORGANISM: Staphylococcus epidermidis

<400> SEQUENCE: 10
ccagaacaat gaatggttaa gg                22

<210> SEQ ID NO 11
<211> LENGTH: 44
<212> TYPE: DNA
<213> ORGANISM: Artificial sequence
<220> FEATURE:
<223> OTHER INFORMATION: Synthetic probe

<400> SEQUENCE: 11
tcactcgagt cgtcgtgatg agctgtttga atattagatg gcac                44

<210> SEQ ID NO 12
<211> LENGTH: 27
<212> TYPE: DNA
<213> ORGANISM: Artificial sequence
<220> FEATURE:
<223> OTHER INFORMATION: Synthetic probe

<400> SEQUENCE: 12
ccaccgccat tattacgaac catcacg                27

<210> SEQ ID NO 13
<211> LENGTH: 44
<212> TYPE: DNA
<213> ORGANISM: Artificial sequence
<220> FEATURE:
<223> OTHER INFORMATION: Synthetic probe

<400> SEQUENCE: 13
tcactcgagt cgtcgtgatg agctgtttga atattagatg gcac                44

<210> SEQ ID NO 14
<211> LENGTH: 27
<212> TYPE: DNA
<213> ORGANISM: Artificial sequence
<220> FEATURE:
<223> OTHER INFORMATION: Synthetic probe

<400> SEQUENCE: 14

```
ccaccgccat tattacgaac catcacg                                              27

<210> SEQ ID NO 15
<211> LENGTH: 27
<212> TYPE: DNA
<213> ORGANISM: Artificial sequence
<220> FEATURE:
<223> OTHER INFORMATION: Synthetic probe

<400> SEQUENCE: 15
ccaccgccat tatttcgaac catcacg                                              27

<210> SEQ ID NO 16
<211> LENGTH: 27
<212> TYPE: DNA
<213> ORGANISM: Artificial sequence
<220> FEATURE:
<223> OTHER INFORMATION: Synthetic probe

<400> SEQUENCE: 16
ccaccgccat aattacgaac catcacg                                              27

<210> SEQ ID NO 17
<211> LENGTH: 27
<212> TYPE: DNA
<213> ORGANISM: Artificial sequence
<220> FEATURE:
<223> OTHER INFORMATION: Synthetic probe

<400> SEQUENCE: 17
ccaccgccat tattcgtac catcacg                                               27

<210> SEQ ID NO 18
<211> LENGTH: 42
<212> TYPE: DNA
<213> ORGANISM: Artificial sequence
<220> FEATURE:
<223> OTHER INFORMATION: Synthetic probe

<400> SEQUENCE: 18
tctttctcaa ttgaccaccg ccattattac gaaccatcac ga                             42

<210> SEQ ID NO 19
<211> LENGTH: 42
<212> TYPE: DNA
<213> ORGANISM: Artificial sequence
<220> FEATURE:
<223> OTHER INFORMATION: Synthetic probe

<400> SEQUENCE: 19
tctttctcat cggaccaccg ccattattac gaaccatcac ga                             42

<210> SEQ ID NO 20
<211> LENGTH: 46
<212> TYPE: DNA
<213> ORGANISM: Artificial sequence
<220> FEATURE:
<223> OTHER INFORMATION: Synthetic probe

<400> SEQUENCE: 20
tctttctcaa tttcgtgatg agctgtttga atattagatg gcacac                         46

<210> SEQ ID NO 21
<211> LENGTH: 43
<212> TYPE: DNA
```

```
<213> ORGANISM: Artificial sequence
<220> FEATURE:
<223> OTHER INFORMATION: Synthetic probe

<400> SEQUENCE: 21
tctttctcat cgtgatgagc tgtttgaata ttagatggca cac          43
```